(12) United States Patent
Yee et al.

(10) Patent No.: US 12,319,740 B2
(45) Date of Patent: Jun. 3, 2025

(54) METHODS FOR PRODUCTION OF TISSUE RESIDENT MEMORY-LIKE T CELLS AND USE THEREOF

(71) Applicant: Board of Regents, The University of Texas System, Austin, TX (US)

(72) Inventors: Cassian Yee, Houston, TX (US); Farah Hasan, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 1081 days.

(21) Appl. No.: 17/286,086

(22) PCT Filed: Oct. 18, 2019

(86) PCT No.: PCT/US2019/057016
§ 371 (c)(1),
(2) Date: Apr. 16, 2021

(87) PCT Pub. No.: WO2020/081987
PCT Pub. Date: Apr. 23, 2020

(65) Prior Publication Data
US 2021/0355443 A1    Nov. 18, 2021

Related U.S. Application Data

(60) Provisional application No. 62/846,270, filed on May 10, 2019, provisional application No. 62/747,523, filed on Oct. 18, 2018.

(51) Int. Cl.
| | |
|---|---|
| *C07K 16/28* | (2006.01) |
| *A61K 39/395* | (2006.01) |
| *A61K 40/11* | (2025.01) |
| *A61K 40/32* | (2025.01) |
| *A61K 40/42* | (2025.01) |
| *C12N 5/0783* | (2010.01) |

(52) U.S. Cl.
CPC ...... *C07K 16/2878* (2013.01); *A61K 39/3955* (2013.01); *A61K 40/11* (2025.01); *A61K 40/32* (2025.01); *A61K 40/4272* (2025.01); *A61K 40/4273* (2025.01); *C12N 5/0636* (2013.01); *C12N 2501/15* (2013.01); *C12N 2501/2315* (2013.01); *C12N 2501/73* (2013.01); *C12N 2502/1121* (2013.01)

(58) Field of Classification Search
None
See application file for complete search history.

(56) References Cited

U.S. PATENT DOCUMENTS

| | | |
|---|---|---|
| 5,962,318 A | 10/1999 | Rooney et al. |
| 2008/0131415 A1 | 6/2008 | Riddell et al. |
| 2015/0299656 A1 | 10/2015 | Gattinoni et al. |
| 2018/0117021 A1 | 5/2018 | Zhou et al. |
| 2018/0228839 A1 | 8/2018 | Shrikant |
| 2024/0197782 A1* | 6/2024 | Yee .................. A61P 37/02 |

FOREIGN PATENT DOCUMENTS

| | | |
|---|---|---|
| WO | WO 2017/079113 | 5/2017 |
| WO | WO 2018/106972 | 6/2018 |

OTHER PUBLICATIONS

Atkuri, K. R. et al., "Culturing at atmospheric oxygen levels impacts lymphocyte function." *PNAS*, 102.10 (2005): 3756-3759.
Caldwell, C. C. et al., "Differential effects of physiologically relevant hypoxic conditions on T lymphocyte development and effector functions," *Journal of Immunology*, 167.11 (2001): 6140-6149.
Extended European Search Report issued in European Patent Application No. 19872505.3, dated Jun. 23, 2022.
Dijkgraaf, F. E. et al., "Formation of Tissue-Resident CD8+ T-Cell Memory," *Cold Spring Harbor Perspectives in Biology*, 13 (2021): 1-20.
Ganesan, A-P. et al., "Tissue-resident memory features are linked to the magnitude of cytotoxic T cell responses in human lung cancer," *Nat Immunol*, 18.8 (2017): 940-950.
Hasan, F. et al., "Abstract A64: In vitro induction of human tissue resident memory phenotype T-cells for use in adoptive cellular therapy," *Poster Presentations Proffered Abstracts*, (2020): A64-A64.
Hombrink, P. et al., "Programs for the persistence, vigilance and control of human CD8+ lung-resident memory T cells," *Nature Immunology*, 17.12 (2016): 1467-1478.
Koprak, S. et al., "Down-regulation of cell surface CXCR6 expression during T cell activation is predominantly mediated by calcineurin," *Cellular Immunology*, 223 (2003): 1-12.
Kumar, B. V. et al., "Human Tissue-Resident Memory T Cells Are Defined by Core Transcriptional and Functional Signatures in Lymphoid and Mucosal Sites," *Cell Reports*, 20 (2017): 2921-2934.
Liikanen, I. et al., "Hypoxia-inducible factor activity promotes antitumor effector function and tissue residency by CD8+ T cells," *The Journal of Clinical Investigation*, 131.7 (2021): 1-17.
Ma, C. et al., "TGF-β Controls the Formation of Kidney-Resident T Cells via Promoting Effector T Cell Extravasation," *The Journal of Immunology*, 198 (2017): 749-756.
Mackay, L. K. et al., "The developmental pathway for CD103(+)CD8+ tissue-resident memory T cells of skin," *Nat Immunol*, 14.12 (2013): 1294-1301.
Mackay, L. K. et al., "Transcriptional Regulation of Tissue-Resident Lymphocytes," *Trends in Immunology*, 38.2 (2017): 94-103.
Mackay. L. K. et al., "T-box Transcription Factors Combine with the Cytokines TGF-beta and IL-15 to Control Tissue-Resident Memory T Cell Fate," *Immunity* 43 (2015): 1101-1111.

(Continued)

*Primary Examiner* — Ilia I Ouspenski
(74) *Attorney, Agent, or Firm* — Parker Highlander PLLC

(57) ABSTRACT

Provided herein are methods for the production of tissue resident memory-like T cells by the combination of hypoxia and TGFβ. Further provided herein are methods of using the tissue resident memory T cells as adoptive cell therapy.

18 Claims, 29 Drawing Sheets
Specification includes a Sequence Listing.

(56) References Cited

OTHER PUBLICATIONS

Mackay, L. K. et al., "Hobit and Blimp1 instruct a universal transcriptional program of tissue residency in lymphocytes," *Science* 352.6284 (2016): 459-463.

Mami-Chouaib, F. et al., "Editorial: Tissue Resident Memory T Cells," *Frontiers in Immunology*, 10 (2019): 1-3.

Milner, J. J. et al., "Runx3 programs CD8(+) T cell residency in non-lymphoid tissues and tumors," *Nature*, 552 (2017): 253-257.

Nizard, M. et al., "Induction of resident memory T cells enhances the efficacy of cancer vaccine," *Nature Communications*, 8.1, (2017): 1-11.

PCT International Preliminary Report on Patentability issued in International Patent Application No. PCT/US2019/057016, dated Apr. 29, 2021.

PCT International Search Report and Written Opinion issued in International Patent Application No. PCT/US2019/057016, dated Feb. 28, 2020.

Skon, C. N. et al., "Transcriptional downregulation of S1pr1 is required for the establishment of resident memory CD8+ T cells," *Nat Immunol*, 14.12 (2013): 1285-1293.

Wein, A. N. et al., "CXCR6 regulates localization of tissue-resident memory CD8 T cells to the airways," *Journal of Experimental Medicine*, 216.12. (2019): 2748-2762.

English translation of Office Action issued in Japanese Patent Application No. 2021-521143, dated Sep. 12, 2023.

Zaid, A. et al., "Chemokine Receptor-Dependent Control of Skin Tissue-Resident Memory T Cell Formation," *The Journal of Immunology*, 199.7 (2017): 2451-2459.

\* cited by examiner

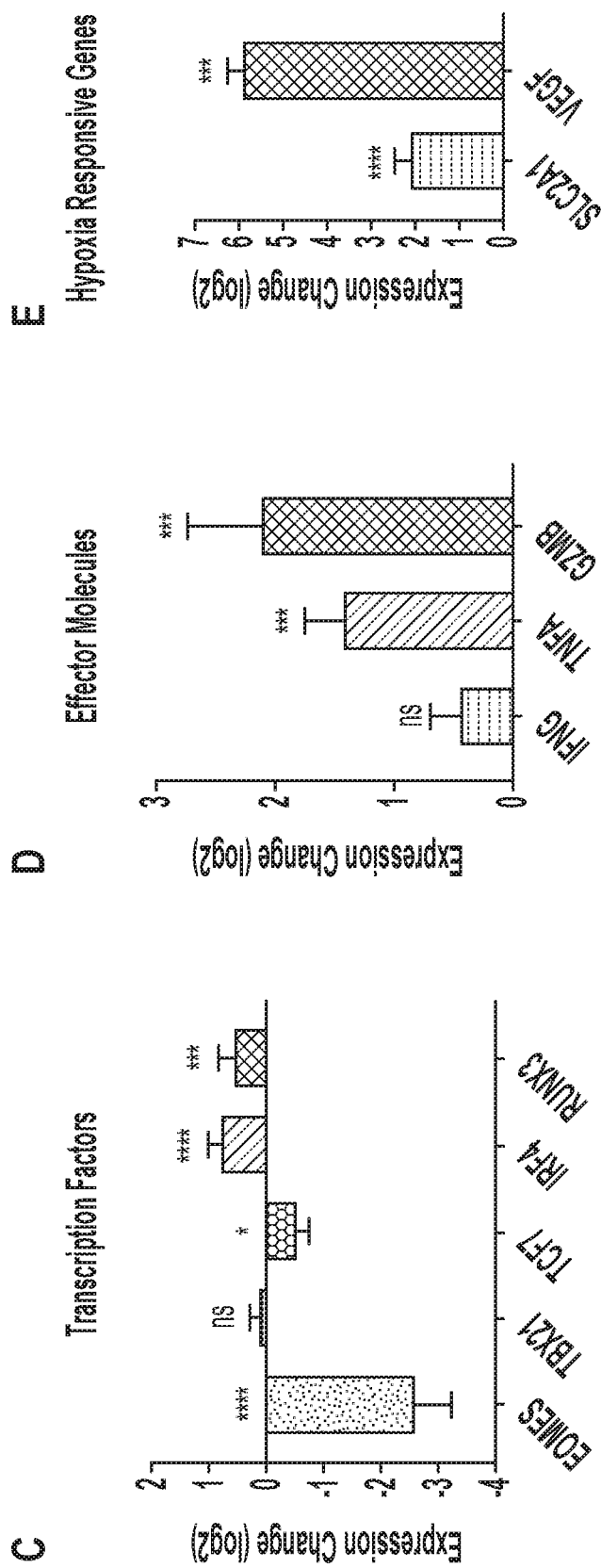
FIGS. 2C-E

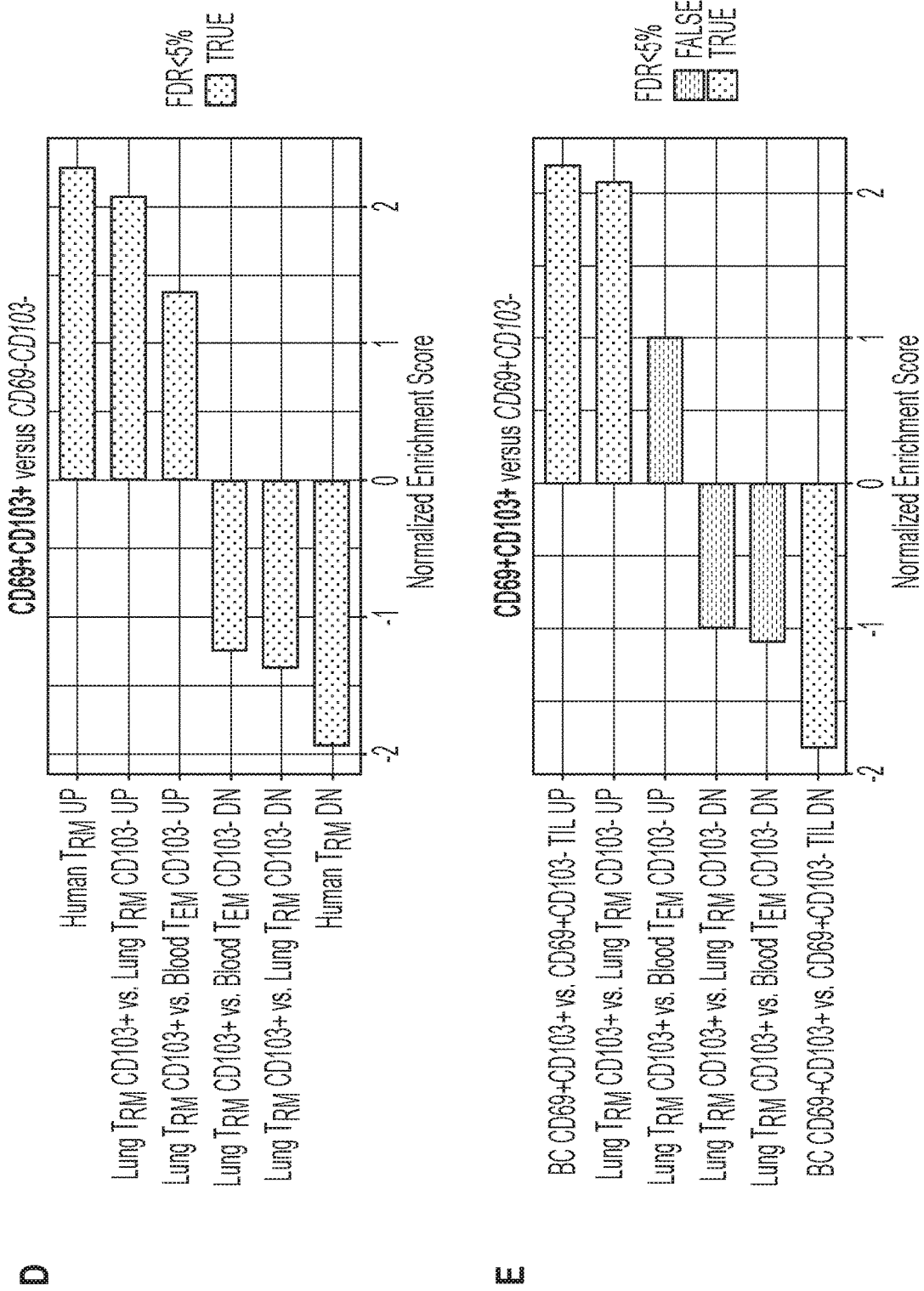
FIG. 5D-E

| | Ingenuity Canonical Pathway | -log(P-value) | | Kumar et al. Lung CD8+CD69+ vs CD8+CD69- |
|---|---|---|---|---|
| | | CD69+CD103+ vs CD69-CD103- | CD69+CD103+ vs CD69+CD103- | |
| Cellular Migration | Axonal Guidance Signaling | 4.21 | 7.74 | 3.55 |
| | Ephrin A Signaling | 2.11 | 3.57 | 1.51 |
| | Leukocyte Extravasation Signaling | 3.32 | 5.27 | N/A |
| | Granulocyte Adhesion and Diapedesis | 2.7 | 5.95 | 2.62 |
| Focal Adhesion | Epithelial Adherens Junction Signaling | 3.26 | 1.75 | N/A |
| | Integrin Signaling | 2.23 | 4.29 | N/A |
| | Paxillin Signaling | 2.06 | 5.87 | 1.5 |
| Inositol Phosphate Signaling | 3-phosphoinositide Biosynthesis | 3.23 | 1.91 | 2.2 |
| | Superpathway of Inositol Phosphate Compounds | 3.14 | 2.01 | 1.76 |
| | D-myo-inositol (1,4,5,6)-Tetrakisphosphate Biosynthesis | 2.11 | 0.633 | N/A |
| | D-myo-inositol (3,4,5,6)-tetrakisphosphate Biosynthesis | 2.11 | 0.633 | N/A |
| T-cell Activation and Differentiation | Th1 and Th2 Activation Pathway | 3.13 | 10.9 | 3.58 |
| | Th2 Pathway | 2.91 | 9.28 | 3.15 |
| | Notch Signaling | 2.5 | 1.38 | 1.45 |

FIG. 6B

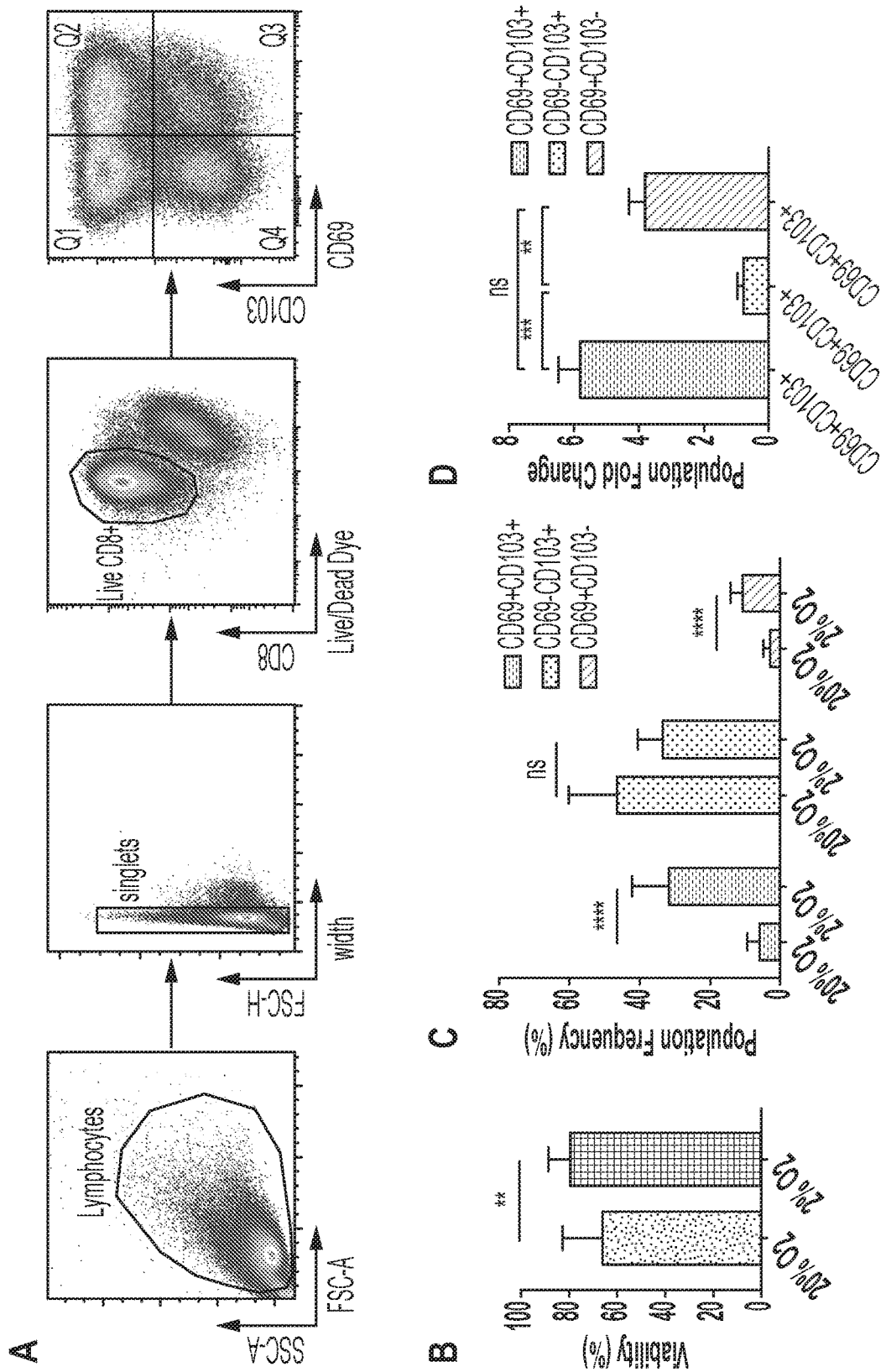
FIG. 7A-D

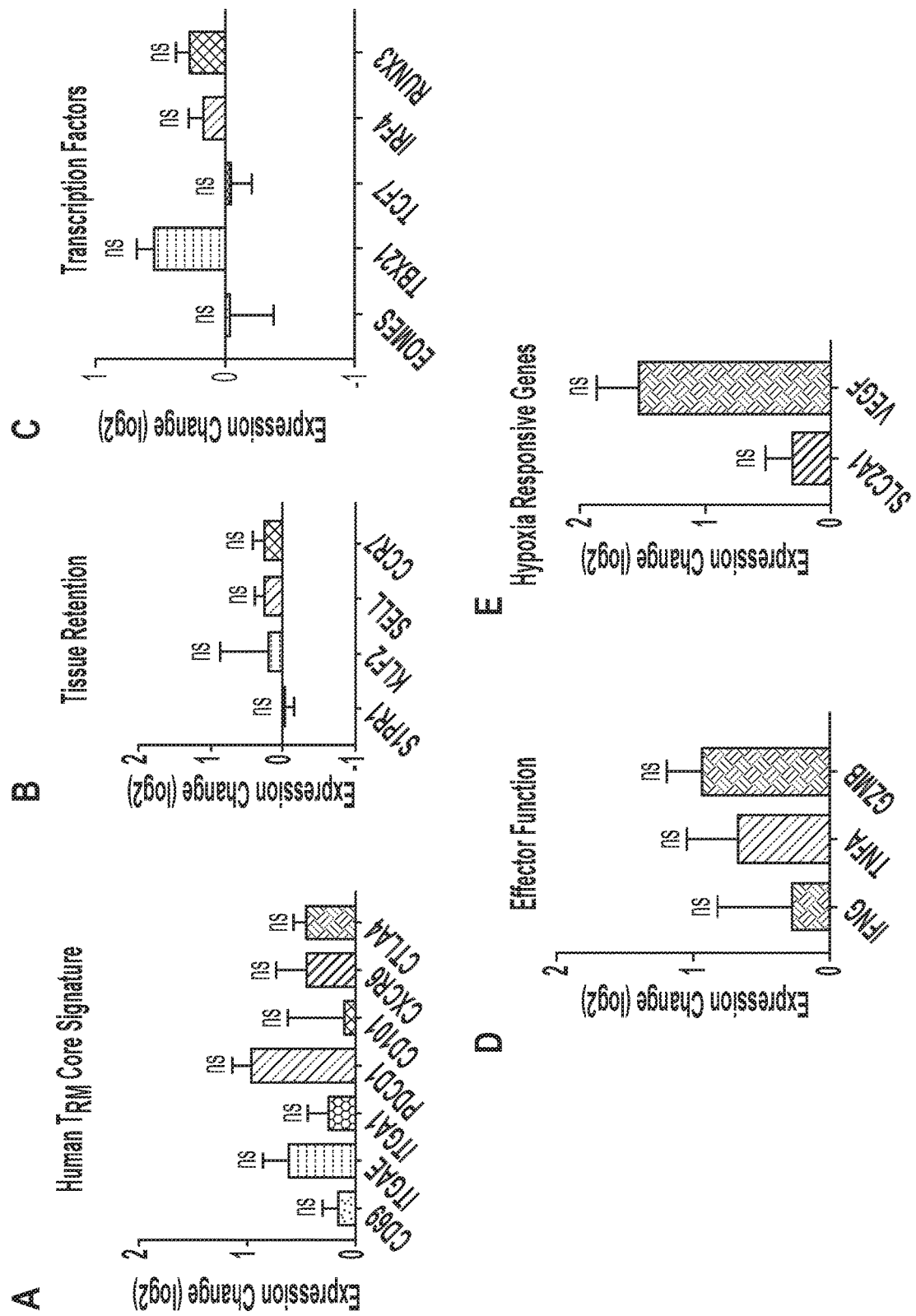
FIG. 8A-E

METHODS FOR PRODUCTION OF TISSUE RESIDENT MEMORY-LIKE T CELLS AND USE THEREOF

This application is a national phase application under 35 U.S.C. § 371 of International Application No. PCT/US2019/057016, filed Oct. 18, 2019, which claims the benefit of U.S. Provisional Patent Application Nos. 62/747,523, filed Oct. 18, 2018 and 62/846,270, filed May 10, 2019, the entirety of each of which are incorporated herein by reference.

INCORPORATION OF SEQUENCE LISTING

The sequence listing that is contained in the file named "UTFCP1408WO_ST25.txt", which is 8 KB (as measured in Microsoft Windows®) and was created on Oct. 17, 2019, is filed herewith by electronic submission and is incorporated by reference herein.

BACKGROUND

1. Field

The present invention relates generally to the fields of medicine and immunology. More particularly, it concerns methods for the production of tissue resident memory-like T cells and uses thereof.

2. Description of Related Art

Tissue resident memory cells ($T_{RM}$) are a recently identified subset of memory T cells that are important in local frontline defense against viral diseases. Recent reports have also suggested that cells with this phenotype play an important role in anti-tumor immunity. Relatively little is known regarding $T_{RM}$ differentiation and endogenous tissue resident memory cells are difficult to isolate, impeding their study in basic research and their application in adoptive cellular therapies. Thus, there is an unmet need for methods to produce tissue resident memory cells.

SUMMARY

In one embodiment, the present disclosure provides an in vitro method for producing tissue resident memory-like T cells ($T_{RM}$-like T cells) comprising: (a) obtaining a starting population of T cells; (b) culturing the starting population of T cells in hypoxic conditions or in the presence of a hypoxia-inducing agent to generate early effector cells; and (c) further culturing the early effector cells in the presence of transforming growth factor beta 1 (TGF-β1) to produce $T_{RM}$-like T cells.

In another embodiment, the present disclosure provides an in vitro method for producing tissue resident memory-like T cells ($T_{RM}$-like T cells) comprising: (a) obtaining a starting population of T cells; (b) culturing the starting population of T cells in hypoxic conditions or in the presence of a hypoxia-inducing agent to generate early effector cells; and (c) further culturing the early effector cells in the presence of transforming growth factor beta 1 (TGF-β1), transforming growth factor beta 2 (TGF-β2) transforming growth factor beta 3 (TGF-β3) or transforming growth factor beta 4 (TGF-β4) to produce $T_{RM}$-like T cells. In some embodiments, culturing comprises activating the starting population of T cells to generate early effector cells.

In yet another embodiment, the present disclosure provides an in vitro method for producing $T_{RM}$-like T cells comprising: (a) obtaining a starting population of T cells; (b) culturing the starting population of T cells in hypoxic conditions or in the presence of a hypoxia-inducing agent; and (c) further culturing the starting population of T cells in the presence of TGF-β1 to produce $T_{RM}$-like T cells.

In some aspects, the starting population of T cells are $CD8^+$ peripheral blood T cells. In specific aspects, the $CD8^+$ peripheral blood T cells are human $CD8^+$ peripheral blood T cells. In certain aspects, obtaining the human $CD8^+$ peripheral blood T cells comprises selecting for $CD45RA^+CCR7^+$ $CD8^+$ naive T cells from a peripheral blood sample. In some aspects, the peripheral blood sample is obtained from a healthy subject. In some aspects, the peripheral blood sample is obtained from a subject diagnosed with cancer or suspected of having cancer. In some aspects, the peripheral blood sample is obtained from a subject diagnosed with a viral disease or is suspected of having a viral disease. In certain aspects, the starting population of T cells were generated by stimulation of naive T cells by antigen presenting cells pulsed with peptide, full length antigen or cell lysate. In particular aspects, the T cells are obtained from a tumor site or are tumor infiltrating lymphocytes. In some aspects, T cells are naive T cells. For example, the cell lysate is a tumor lysate. In specific aspects, the antigen is a cancer antigen. In some aspects, the peptide is a peptide from a protein that is differentially expressed in or highly expressed by cancer cells. In some aspects, the peptide is a peptide from a neoantigen or from a protein comprising a mutation. In certain aspects, the starting population of T cells is enriched for T cells specific for an antigen of interest. In certain aspects, the starting population of T cells are purified to enrich for CD8-positive peptide MHC tetramer-positive cells. In some aspects, the starting population of T cells are purified by fluorescence activated cell sorting. In certain aspects, the starting population of T cells are engineered T cells. In some aspects, the engineered T cells are generated by introduction of a cloned T cell receptor (TCR) into a population of host cells. In certain aspects, the population of host cells are peripheral blood mononuclear cells. In some aspects, the cloned TCR is introduced into the population of host cells by non-viral methods, such as an episomal vector or transposon-transposase system. In particular aspects, the cloned TCR is introduced into the population of host cells by transduction. In some aspects, the population of host cells are transduced by a viral vector comprising TCR alpha and TCR beta chains. In certain aspects, the viral vector is a lentiviral vector. In some aspects, the transduced population of host cells are purified to enrich for CD8-positive peptide MHC tetramer-positive cells. In particular aspects, the engineered T cells expressed a chimeric antigen receptor. In specific aspects, the chimeric antigen receptor comprises a cloned TCR. In some aspects, the starting population of T cells are tumor infiltrating lymphocytes obtained from a subject.

In certain aspects, hypoxic conditions are further defined as less than 5% oxygen, such as 4%, 3%, 2%, 1%, or less oxygen. In some aspects, the hypoxia-inducing agent is a hypoxia mimetic. In particular aspects, the hypoxia-inducing agent or hypoxia mimetic is cobalt chloride ($CoCl_2$), deferoxamine mesylate (DFOM), dimethyloxalyglycine (DMOG), or a prolyl hydroxylase inhibitor, such as a 2-OG analog. In some aspects, the prolyl hydroxylase inhibitor is Roxadustat (FG-4592).

In some aspects, the culturing of step (b) is in the presence of TCR stimulation and co-stimulation. In certain aspects, the TCR stimulation and co-stimulation comprises anti-CD3 and anti-CD28 antibodies, anti-CD3 and anti-CD28 beads, feeder cells, antigen presenting cells, artificial antigen presenting cells, peptide and/or protein antigens, or a combination thereof. In some aspects, the TCR stimulation and co-stimulation comprises anti-CD3 and anti-CD28 beads. In particular aspects, the culturing of step (b) is for 3-5 days, such as for 4 days. In certain aspects, the culturing of step (b) is performed at normoxia, such as 20% oxygen. In certain aspects, the step of culturing of step (b) is performed in the presence of IL-2, such as 25-100 IU/mL, such as 25, 50, or 75 IU/mL. In some aspects, the culturing of step (b) is performed in hypoxic conditions, such as 2% oxygen. In particular aspects, the culturing is in the presence of IL-15. In some aspects, the IL-15 is present at a concentration of 5-20 ng/mL, such as 7-12 ng/mL, specifically 7, 8, 9, 10, 11, or 12 ng/mL.

In certain aspects, TGF-β1 is further defined as recombinant human TGF-β1 (rhTGF-β1). In some aspects, the rhTGF-β1 is present at a concentration of 0.1 to 5 ng/mL, such as 1 to 1.5 ng/mL, specifically 1.1, 1.15, 1.2, 1.25, 1.3, 1.35, 1.4, 1.45, or 1.5 ng/mL. In some embodiments, rhTGF-β1 is present at a concentration of about 2, 3, 4, 5, 6, 7, 8, 9, 10 ng/mL. In still other embodiments rhTGF-β1 is present at a concentration of about 15, 20, 25, 30, 35, 40, 45 or 50 ng/mL. In some aspects, the culturing of step (c) is in hypoxic conditions or in the presence of a hypoxia-inducing agent. In particular aspects, the culturing of step (c) is for 1-3 days, such as for 2 days.

In some aspects, the T %-like T cells are CD69+CD103. In particular aspects, at least 30%, such as 40%, 45%, 50%, 55%, 60% or higher, of the cells produced in step (c) are CD69$^+$CD103$^+$ cells. In some aspects, the $T_{RM}$-like T cells express PD-1, CD101, and/or CD49a. In particular aspects, the $T_{RM}$-like T cell expression PD-1, CD101, and/or CD49a is measured as cell surface expression (e.g., via flow cytometry). In certain aspects, the $T_{RM}$-like T cells have higher expression of CD69, ITGAE, PDCD1, and/or CD101, as compared to cells cultured in atmospheric oxygen conditions. In certain aspects, higher expression of CD69, ITGAE, PDCD1, and/or CD101 is higher expression of CD69, ITGAE, PDCD1, and/or CD101 protein as compared to cells cultured in atmospheric oxygen conditions. In other aspects, higher expression of CD69, ITGAE, PDCD1, and/or CD101 is higher expression of CD69, ITGAE, PDCD1, and/or CD101 mRNA transcripts as compared to cells cultured in atmospheric oxygen conditions.

In certain aspects, the $T_{RM}$-like T cells have higher expression of TNFA, GZMB, SLC2A, and/or VEGF as compared to cells cultured in atmospheric oxygen conditions. In certain aspects, higher expression of TNFA, GZMB, SLC2A1, and/or VEGF is higher expression of TNFα, GZMB, GLUT1, and/or VEGF protein as compared to cells cultured in atmospheric oxygen conditions. In other aspects, higher expression of TNFA, GZMB, SLC2A1, and/or VEGF is higher expression of TNFA, GZMB, SLC2A, and/or VEGF mRNA transcripts as compared to cells cultured in atmospheric oxygen conditions.

In some aspects, the $T_{RM}$-like T cells have decreased expression of S1PR1, KLF2, and/or SELL as compared to cells cultured in atmospheric oxygen conditions. In some aspects, the $T_{RM}$-like T cells have decreased expression of S1PR1, KLF2, and/or CD62L protein as compared to cells cultured in atmospheric oxygen conditions. In some aspects, the $T_{RM}$-like T cells have decreased expression of S1PR1, KLF2, and/or SELL mRNA transcripts as compared to cells cultured in atmospheric oxygen conditions.

In specific aspects, the $T_{RM}$-like T cells have essentially no expression of CXCR6 protein. In particular aspects, the Twi-like T cells have essentially no detectable cell surface expression of CXCR6 protein.

In some aspects, the Ti-like T cells have higher expression of GNLY, MYO7A, ITGAE, EGR2, CCL20, ATPIB1, NR4A3, PERP, RASGEF1B, NR4A1, BMF, EGR1, CXCL13, PDCD1, ITGA1, CCL22, CA10, RGS1, ITGA1, CD101, TNFRSF9 (4-1BB), CCL4, CCL5, NOTCH1, RBPJ, STRIP2, ARHGEF40, DBH, SRGAP3, CSGALNACT1, GPR25, RGS16, DAPK2, NCS1, COL6A3, GDPD4, SLC1A4, CDK14, LMCD1, ILDR2, and/or ADCY3 as compared to cells cultured in atmospheric oxygen conditions. In certain aspects, higher expression of GNLY, MYO7A, ITGAE, EGR2, CCL20, ATPIB1, NR4A3, PERP, RASGEF1B, NR4A1, BMF, EGR1, CXCL13, PDCD1, ITGA1, CCL22, CA10, RGS1, ITGA1, CD101, TNFRSF9 (4-1BB), CCL4, CCL5, NOTCH1, RBPJ, STRIP2, ARHGEF40, DBH, SRGAP3, CSGALNACT1, GPR25, RGS16, DAPK2, NCS1, COL6A3, GDPD4, SLC1A4, CDK14, LMCD1, ILDR2, and/or ADCY3 protein. In certain aspects, higher expression of GNLY, MYO7A, ITGAE, EGR2, CCL20, ATPIB1, NR4A3, PERP, RASGEF1B, NR4A1, BMF, EGR1, CXCL13, PDCD1, ITGA1, CCL22, CA10, RGS1, ITGA1, CD101, TNFRSF9 (4-1BB), CCL4, CCL5, NOTCH1, RBPJ, STRIP2, ARHGEF40, DBH, SRGAP3, CSGALNACT1, GPR25, RGS16, DAPK2, NCS1, COL6A3, GDPD4, SLC1A4, CDK14, LMCD1, ILDR2, and/or ADCY3 mRNA transcripts.

In some aspects, the $T_{RM}$-like T cells have higher expression of GNLY, MYO7A, ITGAE, EGR2, CCL20, ATPIB1, NR4A3, PERP, RASGEF1B, NR4A1, BMF, EGR1, CXCL13, PDCD1, ITGA1, CCL22, CA10, and/or RGS1 as compared to cells cultured in atmospheric oxygen conditions. In certain aspects, higher expression of GNLY. MYO7A, ITGAE, EGR2, CCL20. ATPIB1, NR4A3, PERP, RASGEF1B, NR4A1, BMF, EGR1, CXCL13, PDCD1, ITGA1, CCL22, CA10, and/or RGS1 is higher expression of GNLY, MYO7A, ITGAE, EGR2, CCL20, ATPIB1, NR4A3, PERP, RASGEF1B, NR4A1, BMF, EGR1, CXCLI3, PDCD1, ITGA1, CCL22, CA10, and/or RGS1 protein. In certain aspects, higher expression of GNLY, MYO7A, ITGAE, EGR2, CCL20, ATPIB1, NR4A3, PERP, RASGEF1B, NR4A1, BMF, EGR1, CXCL13, PDCD1, ITGA1, CCL22, CA10, and/or RGS1 is higher expression of GNLY. MYO7A, ITGAE, EGR2, CCL20, ATP1B1, NR4A3, PERP, RASGEF1B, NR4A1, BMF, EGR1, CXCL13, PDCD1, ITGA1, CCL22, CA10, and/or RGS1 mRNA transcripts.

In some aspects, the $T_{RM}$-like T cells have higher expression of ITGAE, ITGA1, PDC1, CD101, TNFRSF9 (4-1BB), CXCL13, CCL20, NOTCH1, RBPJ, NR4A1, EGR2, and/or RGS1 as compared to cells cultured in atmospheric oxygen conditions. In certain aspects, higher expression ITGAE, ITGA1, PDCD1, CD101, TNFRSF9 (4-1BB), CXCL13, CCL20, NOTCH1, RBPJ, NR4A1, EGR2, and/or RGS1 is higher expression of ITGAE, ITGA1, PDCD1, CD101, TNFRSF9 (4-1BB), CXCL13, CCL20, NOTCH1, RBPJ, NR4A1, EGR2, and/or RGS1 protein. In certain aspects, higher expression of ITGAE, ITGA1, PDCD1, CD101, TNFRSF9 (4-1BB), CXCL13, CCL20, NOTCH1, RBPJ, NR4A1, EGR2, and/or RGS1 is higher expression of ITGAE, ITGA1, PDCD1, CD101, TNFRSF9 (4-1BB), CXCL13, CCL20, NOTCH1, RBPJ, NR4A1, EGR2, and/or RGS1 mRNA transcripts.

In some aspects, the $T_{RM}$-like T cells have higher expression of MYO7A, STRIP2, ARHGEF40, ITGAE, DBH, SRGAP3, CSGALNACT1, GPR25, RGS16, DAPK2, NCS1, COL6A3, GDPD4, SLC1A4, CXCL13, CDK14, LMCD1, ILDR2, and/or ADCY3 as compared to cells cultured in atmospheric oxygen conditions. In certain aspects, higher expression MYO7A, STRIP2, ARHGEF40, ITGAE, DBH, SRGAP3, CSGALNACT1, GPR25, RGS16, DAPK2, NCS1, COL6A3, GDPD4, SLC1A4, CXCL13, CDK14, LMCD1, ILDR2, and/or ADCY3 is higher expression of MYO7A, STRIP2, ARHGEF40, ITGAE, DBH, SRGAP3, CSGALNACT1, GPR25, RGS16, DAPK2, NCS1, COL6A3, GDPD4, SLC1A4, CXCL13, CDK14, LMCD1, ILDR2, and/or ADCY3 protein. In certain aspects, higher expression of MYO7A, STRIP2, ARHGEF40, ITGAE, DBH, SRGAP3, CSGALNACT1, GPR25, RGS16, DAPK2, NCS1, COL6A3, GDPD4, SLC1A4, CXCL13, CDK14, LMCD1, ILDR2, and/or ADCY3 is higher expression of MYO7A, STRIP2, ARHGEF40, ITGAE, DBH, SRGAP3, CSGALNACT1, GPR25, RGS16, DAPK2, NCS1, COL6A3, GDPD4, SLC1A4, CXCL13, CDK14, LMCD1, ILDR2, and/or ADCY3 mRNA transcripts.

In some aspects, the $T_{RM}$-like T cells have lower expression of CD58, NR3C1, RAP1GAP2, SELP, CXCR2, TBX21, ITGAL, SELL, KLF3, KLF2, RASGRP2, FAM65B, SERPINE2, ITGAM, KLRB1, TGFBR3, SMAD3, TNFSF8, DUSP2, PLEK, GOLGA2P7, FOSB, PLCG2, SLAMF7, SLC6A8, SOCS3, and/or PTGER2 as compared to cells cultured in atmospheric oxygen conditions. In certain aspects, lower expression of CD58, NR3C1, RAP1GAP2, SELP, CXCR2, TBX21, ITGAL, SELL, KLF3, KLF2, RASGRP2, FAM65B, SERPINE2, ITGAM, KLRB1, TGFBR3, SMAD3 TNFSF8, DUSP2, PLEK, GOLGA2P7, FOSB, PLCG2, SLAMF7, SLC6A8, SOCS3, and/or PTGER2 is lower expression of CD58, NR3C1, RAP1GAP2, SELP, CXCR2, TBX21, ITGAL, SELL, KLF3, KLF2, RASGRP2, FAM65B, SERPINE2, ITGAM, KLRB1, TGFBR3, SMAD3, TNFSF8, DUSP2, PLEK, GOLGA2P7, FOSB, PLCG2, SLAMF7, SLC6A8, SOCS3, and/or PTGER2 protein. In certain aspects, lower expression of CD58, NR3C1, RAP1GAP2, SELP, CXCR2, TBX21, ITGAL, SELL, KLF3, KLF2, RASGRP2, FAM65B, SERPINE2, ITGAM, KLRB1, TGFBR3, SMAD3, TNFSF8, DUSP2, PLEK, GOLGA2P7, FOSB, PLCG2, SLAMF7, SLC6A8, SOCS3, and/or PTGER2 is lower expression of CD58, NR3C1, RAP1GAP2, SELP, CXCR2, TBX21, ITGAL, SELL, KLF3, KLF2, RASGRP2, FAM65B, SERPINE2, ITGAM, KLRB1, TGFBR3, SMAD3, TNFSF8, DUSP2, PLEK, GOLGA2P7, FOSB, PLCG2, SLAMF7, SLC6A8, SOCS3, and/or PTGER2 mRNA transcripts.

In some aspects, the Tan-like T cells have lower expression of CD58, NR3C1, RAP1GAP2, SELP, CXCR2, TBX21, ITGAL, SELL, KLF3, RASGRP2, ITGAM, KLRB1, TGFBR3, SMAD3, and/or TNFSF8 as compared to cells cultured in atmospheric oxygen conditions. In certain aspects, lower expression of CD58, NR3C1, RAP1GAP2, SELP, CXCR2, TBX21, ITGAL, SELL, KLF3, RASGRP2, ITGAM, KLRB1, TGFBR3, SMAD3, and/or TNFSF8 is lower expression of CD58, NR3C1, RAP1GAP2, SELP, CXCR2, TBX21, ITGAL, SELL, KLF3, RASGRP2, ITGAM, KLRB1, TGFBR3, SMAD3, and/or TNFSF8 protein. In certain aspects, lower expression of CD58, NR3C1, RAP1GAP2, SELP, CXCR2, TBX21, ITGAL, SELL, KLF3, RASGRP2, ITGAM, KLRB1, TGFBR3, SMAD3, and/or TNFSF8 is lower expression of CD58, NR3C1, RAP1GAP2, SELP, CXCR2, TBX21, ITGAL, SELL, KLF3, RASGRP2, ITGAM. KLRB1, TGFBR3, SMAD3, and/or TNFSF8 mRNA transcripts.

In some aspects, the $T_{RM}$-like T cells have higher expression of GNLY, MYO7A, ITGAE, EGR2, CCL20, ATP1B1, NR4A3, PERP, RASGEF1B, NR4A1, BMF, EGR1, CXCL13, PDCD1, ITGA1, CCL22, CA10, and/or RGS1 as compared to cells cultured in atmospheric oxygen conditions. In certain aspects, higher expression of GNLY, MYO7A, ITGAE, EGR2, CCL20, ATPIB1, NR4A3, PERP, RASGEF1B, NR4A1, BMF, EGR1, CXCL13, PDCD1, ITGA1, CCL22, CA10, and/or RGS1 is higher expression of GNLY, MYO7A, ITGAE, EGR2, CCL20, ATPIB1, NR4A3, PERP, RASGEF1B, NR4A1, BMF, EGR1, CXCL13, PDCD1, ITGA1, CCL22, CA10, and/or RGS1 protein. In certain aspects, higher expression of GNLY, MYO7A, ITGAE, EGR2, CCL20, ATPIB1, NR4A3, PERP, RASGEF1B, NR4A1, BMF, EGR1, CXCL13, PDCD1, ITGA1, CCL22, CA10, and/or RGS1 is higher expression of GNLY, MYO7A, ITGAE, EGR2, CCL20, ATP1B1, NR4A3, PERP, RASGEF1B, NR4A1, BMF, EGR1, CXCL13, PDCD1, ITGA1, CCL22, CA10, and/or RGS1 mRNA transcripts.

In some aspects, the $T_{RM}$-like T cells have higher expression of MYO7A, STRIP2, ARHGEF40, ITGAE, DBH, SRGAP3, CSGALNACT1, GPR25, RGS16, DAPK2, NCS1, COL6A3, GDPD4, SLC1A4, CXCL13, CDK14, LMCD1, ILDR2, and/or ADCY3 as compared to cells cultured in atmospheric oxygen conditions. In certain aspects, higher expression of MYO7A, STRIP2, ARHGEF40, ITGAE, DBH, SRGAP3, CSGALNACT1, GPR25, RGS16, DAPK2, NCS1, COL6A3, GDPD4, SLC1A4, CXCL13, CDK14, LMCD1, ILDR2, and/or ADCY3 is higher expression of MYO7A, STRIP2, ARHGEF40, ITGAE, DBH, SRGAP3, CSGALNACT1, GPR25, RGS16, DAPK2, NCS1, COL6A3, GDPD4, SLC1A4, CXCL13, CDK14, LMCD1, ILDR2, and/or ADCY3 protein. In certain aspects, higher expression of MYO7A, STRIP2, ARHGEF40, ITGAE, DBH, SRGAP3, CSGALNACT1, GPR25, RGS16, DAPK2, NCS1, COL6A3, GDPD4, SLC1A4, CXCL13, CDK14, LMCD1, ILDR2, and/or ADCY3 is higher expression of MYO7A, STRIP2, ARHGEF40, ITGAE, DBH, SRGAP3, CSGAL-NACT1, GPR25, RGS16, DAPK2, NCS1, COL6A3, GDPD4, SLC1A4, CXCL13, CDK14, LMCD1, ILDR2, and/or ADCY3 mRNA transcripts.

In additional aspects, the method further comprises producing $T_{RM}$-like T cells with specificity for an antigen of interest. In some aspects, the $T_{RM}$-like T cells with specificity for an antigen of interest are engineered to by transducing the $T_{RM}$-like T cells with a T cell receptor (TCR) specific for the antigen of interest. In other aspects, the $T_{RM}$-like T cells with specificity for an antigen of interest are produced by using a starting population of T cells with specificity for an antigen of interest. In some aspects, $T_{RM}$-like T cells are activated by culturing the starting population of T cells with peptide-pulsed antigen presenting cells (APCs), such as artificial APCs (aAPCs), during step (b). In some aspects, the APCs are mature dendritic cells. In specific aspects, steps (b) and (c) are repeated at least once. In some aspects, the Tart-like T cells are cultured in the presence of a histone deacetylase (HDAC) inhibitor during step (b) and/or step (c). In particular aspects, the HDAC inhibitor is selected from the group consisting of trichostatin A, trapoxin B, phenylbutyrate, valproic acid, vorinostat (suberanilohydroxamic acid or SAHA, marketed as Zolinza®), belinostat (PXD101, marketed as Beleodaqk), panobinostat (marketed as Farydaq®), dacinostat (LAQ824), entinostat (SNDX-275 or MS-275), tacedinaline (C1994), and mocetinostat (MGCD0103).

In some aspects, the antigen of interest is for targeting or treating lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, or melanoma.

Further provided herein is a $T_{RM}$-like T cell with no expression, substantially no expression, or essentially no expression of CXCR6 protein. In some aspects, the no expression of CXCR6 protein is no cell surface expression of CXCR6 protein. In other aspects, the $T_{RM}$-like T cell expresses CXCR6 mRNA transcript but does not express CXCR6 protein or express CXCR6 protein on the cell surface. In some aspects, the $T_{RM}$-like T cells are specific for an antigen of interest. In another embodiment, there is provided a pharmaceutical composition comprising a population of $T_{RM}$-like T cells as provided above. In another embodiment, there is provided a pharmaceutical composition comprising a population of $T_{RM}$-like T cells with essentially no expression of CXCR6 protein and a pharmaceutically acceptable carrier. In some aspects, the $T_{RM}$-like T cells are produced by the methods of the present embodiments. In some aspects, the $T_{RM}$-like T cell(s) express PD-1, CD101, and/or CD49a. In particular aspects, at least 40%, at least 45%, at least 50%, at least 55%, at least 60% or more, of the cells are CD69$^+$CD103$^+$ cells. In certain aspects, $T_{RM}$-like T cell(s) are CD69$^+$CD103$^+$ cells. In some aspects, the $T_{RM}$-like T cells have higher expression of GNLY, MYO7A, ITGAE, EGR2, CCL20, ATP1B1, NR4A3, PERP, RASGEF1B, NR4A1, BMF, EGR1, CXCL13, PDCD1, ITGA1, CCL22, CA10, RGS1, ITGA1, CD101, TNFRSF9 (4-11BB), CCL4, CCL5, NOTCH1, RBPJ, STRIP2, ARHGEF40, DBH, SRGAP3, CSGALNACT1, GPR25, RGS16, DAPK2, NCS1, COL6A3, GDPD4, SLC1A4, CDK14, LMCD1, ILDR2, and/or ADCY3 as compared to cells cultured in atmospheric oxygen conditions. In some aspects, the $T_{RM}$-like T cells have higher expression of GNLY, MYO7A, ITGAE, EGR2, CCL20, ATP1B1, NR4A3, PERP, RASGEF1B, NR4A1, BMF, EGR1, CXCL13, PDCD1, ITGA1, CCL22, CA10, and/or RGS1 as compared to cells cultured in atmospheric oxygen conditions. In some aspects, the $T_{RM}$-like T cells have higher expression of ITGAE, ITGA1, PDC1, CD101, TNFRSF9 (4-1BB), CXCL13, CCL20, NOTCH1, RBPJ, NR4A1, EGR2, and/or RGS1 as compared to cells cultured in atmospheric oxygen conditions. In some aspects, the $T_{RM}$-like T cells have higher expression of MYO7A, STRIP2, ARHGEF40, ITGAE, DBH, SRGAP3, CSGALNACT1, GPR25, RGS16, DAPK2, NCS1, COL6A3, GDPD4, SLC1A4, CXCL13, CDK14, LMCD1, ILDR2, and/or ADCY3 as compared to cells cultured in atmospheric oxygen conditions. In some aspects, the $T_{RM}$-like T cells have lower expression of CD58, NR3C1, RAP1GAP2, SELP, CXCR2, TBX21, ITGAL, SELL, KLF3, KLF2, RASGRP2, FAM65B, SERPINE2, ITGAM, KLRB1, TGFBR3, SMAD3, and/or TNFSF8, DUSP2, PLEK, GOLGA2P7, FOSB, PLCG2, SLAMF7, SLC6A8, SOCS3, and/or PTGER2 as compared to cells cultured in atmospheric oxygen conditions. In some aspects, the $T_{RM}$-like T cells have lower expression of CD58, NR3C1, RAP1GAP2, SELP, CXCR2, TBX21, ITGAL, SELL, KLF3, RASGRP2, ITGAM, KLRB1, TGFBR3, SMAD3, and/or TNFSF8 as compared to cells cultured in atmospheric oxygen conditions. In some aspects, the $T_{RM}$-like T cells have lower expression of KLF2, KLF3, SELL, FAM65B, and/or SERPINE2 as compared to cells cultured in atmospheric oxygen conditions. In some aspects, the $T_{RM}$-like T cells have lower expression of DUSP2, PLEK, GOLGA2P7, FOSB, PLCG2, ITGAM, FOS, KLF3, SLAMF7, TNFSF8, SLC6A8, KLF2, SOCS3, and/or PTGER2 as compared to cells cultured in atmospheric oxygen conditions.

In another embodiment, there is provided a composition comprising an effective amount of $T_{RM}$-like T cells with essentially no expression of CXCR6 protein, such as $T_{RM}$-like T cells produced by the methods of the present embodiments, for the treatment an immune-related disorder in a subject. In particular aspects, the $T_{RM}$-like T cells have specificity for an antigen of interest.

Further provided herein is the use of an effective amount of $T_{RM}$-like T cells with essentially no expression of CXCR6 protein, such as $T_{RM}$-like T cells produced by the methods of the present embodiments, for the treatment of an immune-related disorder in a subject. In particular aspects, the $T_{RM}$-like T cells have specificity for an antigen of interest.

In some aspects, the antigen of interest is for targeting or treating lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, or melanoma.

In a further embodiment, there is provided a method of treating an immune-related disorder in a subject comprising administering an effective amount of $T_{RM}$-like T cells with essentially no expression of CXCR6 protein, such as $T_{RM}$-like T cells produced by the methods of the present embodiments, to the subject. In some aspects, the subject is human.

In some aspects, the immune-related disorder is a cancer, autoimmune disorder, graft versus host disease, allograft rejection, or inflammatory condition. In certain aspects, the subject has received a tissue or organ transplant.

In additional aspects, the method further comprises administering at least one therapeutic agent. In some aspects, the at least one second therapeutic agent comprises chemotherapy, immunotherapy, surgery, radiotherapy, or biotherapy. In some aspects, the $T_{RM}$-like T cells and/or the at least one second therapeutic agent are administered intravenously, intraperitoneally, intratracheally, intratumorally, intramuscularly, endoscopically, intralesionally, percutaneously, subcutaneously, regionally, or by direct injection or perfusion. In certain aspects, the $T_{RM}$-like T cells are administered prior to the second therapeutic agent. In some aspects, the $T_{RM}$-like T cells are administered after the second therapeutic agent. In particular aspects, the $T_{RM}$-like T cells are administered concurrently with the second therapeutic agent. In specific aspects, the immunotherapy is a 4-1BB agonist. In particular aspects, the 4-1BB agonist is a 4-1BB antibody. In other aspects, the second therapeutic agent is an immune checkpoint inhibitor. In particular aspect, the immune checkpoint inhibitor is anti-CTLA-4, anti-PD1 or anti-PD-L1 inhibitor.

In another embodiment, there is provided a method of treating a viral infection in a subject comprising administering an effective amount of $T_{RM}$-like T cells with essentially no CXCR6 expression, such as $T_{RM}$-like T cells produced by the present methods, such as $T_{RM}$-like T cells with specificity for one or more viral antigens.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure. The present disclosure may be better understood by reference to one or more of these drawings in combination with the detailed description of specific embodiments presented herein.

FIGS. 2A-2E: Human CD8$^+$ T-cells exposed to hypoxia and TGF-β1 have a $T_{RM}$-like transcriptional profile. Naïve CD8$^+$ T-cells isolated from peripheral blood were activated in 20% or 2% O2 (hypoxia) for 4 days and then for an additional 2 days with the addition of rhTGF-β1. Expression levels of genes associated with T % were analyzed via quantitative real-time PCR. (A-E) Fold change of gene transcript levels in hypoxia (2% $O_2$)+TGF-β1 over AtmosO$_2$ (~20% $O_2$)+TGF-β1. Canonical hypoxia responsive genes are shown in (E) as a control to indicate activation of cellular hypoxia response. CX3CR1 expression was not detectable, n=6, 3 independent experiments; Paired t-test with Benjamini, Krieger and Yekutieli correction for multiple comparisons; *P<0.05, P<0.01, *P<0.001; FLDR<0.05, data are mean+/−SEM.

FIGS. 5A-5F: Hypoxia and TGF-β1 induced Tαr-phenotype cells show transcriptional differences similar to those reported for endogenous $T_{RM}$. CD69$^-$CD103$^-$, CD69$^+$ CD103$^-$, and CD69$^+$CD103$^+$CD8$^+$ T-cells were generated as described earlier and sorted before isolation of RNA for transcriptome analysis via RNA-sequencing (n=3). (A) Principal-component analysis (PCA) of paired CD69$^-$CD103$^-$, CD69$^+$CD103$^-$, and CD69$^+$CD103$^+$ CD8$^+$T-cells based on the global transcriptome. (B) Unsupervised clustering of the top 150 differentially expressed genes for CD69$^-$ CD103$^-$ (left), CD69$^+$CD103$^-$ (middle), and CD69$^+$CD103$^+$ (right) cells generated in 20% O$_2$, 2% O$_2$, and 2% O$_2$+TGF-β1, respectively. Differential expression determined by |log 2FC|≥1 and FDR<0.05. (C) Expression levels of selected differentially expressed $T_{RM}$-associated genes. GSEA of gene signatures derived from endogenous Tαi and TIL$_{RM}$ in the transcriptome of (D) CD69$^+$CD103$^+$ vs. CD69$^-$CD103$^-$ and (E) CD69$^+$CD103$^+$ vs. CD69$^+$CD103$^-$ cells, presented as normalized enrichment score (NES). (F) Top 34 differentially expressed genes from TIL$_{RM}$GSEA shown in (E).

FIGS. 6A-6B: Pathways involved in metabolism, migration, and $T_{RM}$ generation and maintenance are differentially regulated in hypoxia and TGF-β1 induced $T_{RM}$. (A) Top 30 canonical pathways from the Ingenuity Pathway Analysis (IPA) database that are enriched in CD69$^+$CD103$^+$ in vitro induced $T_{RM}$, shown as the frequency of differentially expressed genes encoding components of each pathway that are upregulated or downregulated in CD69$^+$CD103$^+$ cells relative to their expression in CD69$^-$CD103$^-$ cells, and negative-log-transformed P values (right vertical axis; Fisher's exact test): numbers above bars represent total genes in each pathway, bars are presented in the order of significance. (B) Differentially regulated IPA canonical pathways in hypoxia+TGF-β1 in vitro induced $T_{RM}$ and endogenous human $T_{RM}$.

FIGS. 7A-7D: Differentiation of human CD8$^+$ T-cells in hypoxia and TGF-β1 results in induction of a CD69$^+$ CD103$^+$ population. (A) Gating strategy used in flow cytometry analysis. (B) Cell viability determined by fixable viability dye (Invitrogen) in flow cytometry analysis. (C and D) Changes in population frequencies comparing 20% O$_2$+TGF-β1 and 2% O$_2$+TGF-β1 conditions determined by flow cytometry. n=7, 3 independent experiments; paired t-test (B), ratio paired t-test (C), or ANOVA (D); *P<0.05, P<0.01, *P<0.001, ****p<0.0001.

FIGS. 8A-8F: Human CD8$^+$ T-cells differentiated in 10% O$_2$ and TGF-β1 do not have a $T_{RM}$-like transcriptional profile. Naïve CD8$^+$ T-cells isolated from peripheral blood were activated in 20% O$_2$ (AtmosO$_2$) or 10% O$_2$ (circulationO$_2$) for 4 days and then for an additional 2 days with the addition of rhTGF-β1. Expression levels of $T_{RM}$-associated genes were analyzed via quantitative real-time PCR. (A-E) Fold change of gene transcript levels in 10% O$_2$+TGF-β1 over 20% O$_2$+TGF-β31. (F) The frequency of the CD69$^+$ CD103$^+$ $T_{RM}$-like population was then assessed by flow cytometry. Representative results from 1 donor are shown in (F). n=3, 2 independent experiments; (A-E) Paired t-test with Benjamini. Krieger and Yekutieli correction for multiple comparisons; FDR<0.05, data are mean+/−SEM; (F) unpaired t-test, *P<0.05.

DESCRIPTION OF ILLUSTRATIVE EMBODIMENTS

Figure 1:
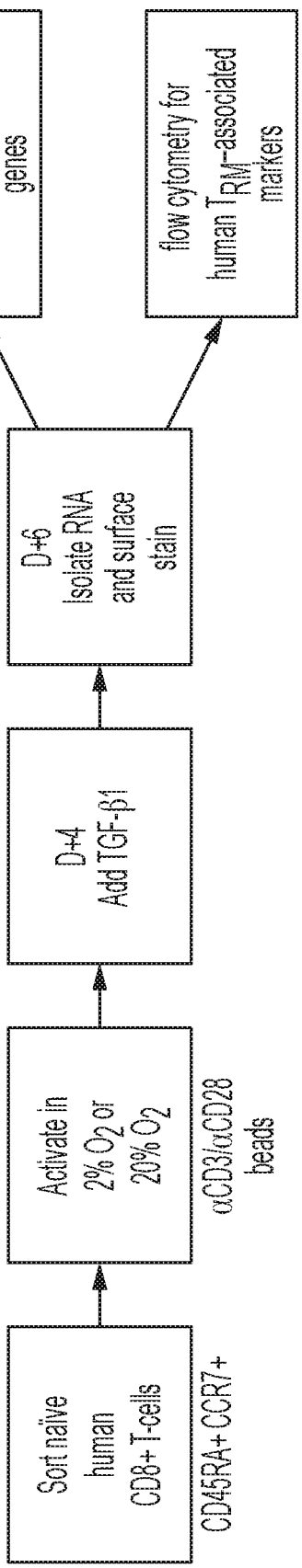
FIG. 1: Schematic depicting method for producing tissue resident memory cells.

Tissue resident memory cells (Tam) are non-recirculating memory T cells that reside in tissues, lack the molecules enabling egress from tissues and migration to lymph nodes, and act as frontline responders (Mami-Chouaib and Tartour, 2019). Relatively little is known about $T_{RM}$ differentiation. Effector T cells that enter tissue can become $T_{RM}$ by up- or downregulating genes allowing tissue retention. In the present studies, it was found that hypoxia and TGF-β1 can induce a $T_{RM}$-like phenotype in human peripheral blood CD8⁺ T-cells. The present studies showed that when human peripheral blood T cells, such as CD8⁺ T cells or CD4⁺ T cells, are differentiated in hypoxia and TGF-β1 in vitro they develop a $T_{RM}$ phenotype and express protein markers and genes commonly associated with tissue resident memory cells (Table 1). These findings identify a previously unreported cue for $T_{RM}$ differentiation and enable a facile means of generating $T_{RM}$-phenotype cells for basic studies and translational applications such as adoptive cellular therapies.

Accordingly, certain embodiments of the present disclosure provide methods for the production of Tin-phenotype cells. The terms "$T_{RM}$phenotype cells" and "$T_{RM}$-like cells" are used interchangeably herein to refer to the cells provided by the present methods. The method can comprise culturing peripheral blood T cells in hypoxic conditions or in the presence of agents which induce or mimic hypoxia, exemplary hypoxia mimetics include but are not limited to cobalt chloride ($CoCl_2$), deferoxamine mesylate (DFOM), dimethyloxalyglycine (DMOG), or a prolyl hydroxylase inhibitor, such as Roxadustat. During this period, the cells can be polyclonally activated, such as by anti-CD3 and anti-CD28 beads, to produce early effector cells. The term "early effector cell" refers to cells that are within one week of activation from the naïve state. The activation may comprise culturing in the presence of TCR stimulation and co-stimulation, including but not limited to anti-CD3/anti-CD28 antibodies, anti-CD3/anti-CD28 beads, feeder cells, antigen presenting cells, artificial antigen presenting cells, peptide and/or protein antigens, or combinations of these. After the activation to produce early effector cells, the cells are further cultured in the presence of TGF-β1 to produce the Ta i-phenotype cells. Thus, hypoxia and TGF-β1 can be used to induce a CD8⁺CD69⁺CD103⁺ cell population that expresses human $T_{RM}$-associated markers. Human CD8⁺ T-cells differentiated in hypoxia and TGF-β1 have a $T_{RM}$-like transcriptional profile.

The $T_{RM}$-like cells may be rendered antigen-specific. One method may comprise polyclonal activation of naïve T cells under the conditions described herein to generate $T_{RM}$-like cells followed by transduction to express an antigen-specific TCR. In a modified version of ETC stimulation method, the naïve T cells may be activated via peptide-pulsed antigen presenting cells (or artificial antigen presenting cells) in hypoxia followed by further culture in the presence of rh TGF-β1. This activation may be performed for 2 rounds to generate the antigen-specific cells. In another method, the antigen-specific $T_{RM}$-like cells may be produced by combination of hypoxia and TGF-β1 with epigenetic modifying agents such as HDAC inhibitors to differentiate already expanded antigen-specific cells to the $T_{RM}$ phenotype.

The present T cells, such as the starting population of T cells, may be engineered T cells. In certain embodiments, the engineered T cells comprise T cells expressing a chimeric antigen receptor (CAR T cells). In certain embodiments, the engineered T cells comprise T cells expressing a recombinant T cell receptor capable of binding tumor-specific epitopes or neoepitopes. In some embodiments, the engineered T cells are constructed using any of the many well-established gene transfer methods known to those skilled in the art. In certain embodiments, the engineered cells are constructed using viral vector-based gene transfer methods to introduce nucleic acids encoding a chimeric antigen receptor specific for a desired target tumor antigen or encoding a recombinant TCR specific for a desired tumor-specific epitope or neoepitope. In certain embodiments, the engineered cells are constructed using non-viral vector-based gene transfer methods to introduce nucleic acids encoding a chimeric antigen receptor specific for a desired target tumor antigen or encoding a recombinant TCR specific for a desired tumor-specific epitope or neoepitope. In certain embodiments, the viral vector-based gene transfer method comprises a lentiviral vector. In certain embodiments, the viral vector-based gene transfer method comprises a retroviral vector. In certain embodiments, the viral vector-based gene transfer method comprises an adenoviral or an adeno-associated viral vector. The non-viral vector-based gene transfer method may comprise an episomal vector or a transposon-transposase system. For example, the transposon-transposase system could be the well-known Sleeping Beauty, the Frog Prince transposon-transposase system, or the TTAA-specific transposon PiggyBac system. In certain embodiments, the non-viral vector-based gene transfer method comprises a gene-editing method selected from the group consisting of a zinc-finger nuclease (ZFN), a transcription activator-like effector nuclease (TALENs), and a clustered regularly interspaced short palindromic repeats (CRISPR)/CRISPR-associated protein 9 (Cas9) nuclease. In certain embodiments, the non-viral vector-based gene editing method comprises a transfection or transformation method selected from the group consisting of lipofection, nucleofection, biolistics, virosomes, liposomes, polycation or lipid:nucleic acid conjugates, naked DNA, artificial virions, and agent-enhanced uptake of DNA.

In certain embodiments, the CAR T cell expresses a CAR construct comprising an extracellular antigen-binding domain, an optional spacer sequence, a transmembrane domain, one or more intracellular signaling domains, and one or more optional regulatory sequences for activating or inactivating the CAR T cell.

In certain embodiments, the extracellular antigen-binding domain comprises a moiety capable of specifically binding a desired target. In certain embodiments, the moiety capable of specifically binding a desired target comprises a monoclonal antibody or antigen-binding fragment thereof. In certain embodiments, the antigen-binding fragment thereof comprises a single-chain variable fragment (scFv) of a monoclonal antibody capable of specifically binding a desired target. In certain embodiments, the desired target is a tumor-specific antigen. In certain embodiments, the tumor-specific antigen is selected from the group consisting of CD19, CD20, CD22, carcinoembryonic antigen, alphafetoprotein, CA-125, MUC-1, epithelial tumor antigen, melanoma-associated antigen (MAGE) (e.g., MAGE-1, MAGE-11, or MAGE-A), mutated p53, mutated ras, HER2/Neu, ERBB2, folate binding protein, HIV-1 envelope glycoprotein gp120, HIV-1 envelope glycoprotein gp41, GD2, CD123, CD23, CD30, CD56, c-Met, mesothelin, GD3, HERV-K, IL-11Ralpha, kappa chain, lambda chain, CSPG4, ERBB2, EGFRvIII, VEGFR2, and human papilloma virus (HPV). In certain embodiments, the desired target is a tumor-specific neoepitope. In certain embodiments, the tumor-specific neoepitope is identified by in silico analysis. In certain embodiments, the tumor-specific neoepitope is identified and purified from a population of autologous TILs derived from a human subject.

In certain embodiments, the transmembrane domain comprises any synthetic or natural amino acid sequence capable of forming a structure able to span a cell membrane. In certain embodiments, the structure able to span a cell membrane comprises an alpha helix. In certain embodiments, the transmembrane region is derived from a naturally occurring transmembrane protein selected from the group consisting of CD3ζ, CD3ε, CD4, CD5, CD8, CD9, CD16, CD22, CD28, CD33, CD37, CD45, CD64, CD80, CD86, CD134, 4-1BB/CD137. CD154, inducible T cell costimulator (ICOS)/CD278, glucocorticoid-induced TNFR-related protein (GITR)/CD357, NKG2D, TCRα and TCRβ. In certain embodiments, the transmembrane region derived from a naturally occurring transmembrane protein comprises one or more amino acid substitutions in sequences known to be involved in interactions with other signaling proteins.

In certain embodiments, the one or more intracellular signaling domains comprise one or more intracellular tyrosine-based activation motifs ("ITAMs"). In certain embodiments, the one or more ITAMs are present on a CD3-zeta (CD3ζ) molecule. In certain embodiments, the one or more intracellular signaling domains further comprise a costimulatory signaling domain selected from the group consisting of CD28, 4-1BB/CD137, ICOS, OX40, CD2, CD40L, CD27, Light-R, GITR, or combinations thereof.

In certain embodiments, the T cells comprise a recombinant T cell receptor capable of binding tumor-specific epitopes or neoepitopes. In certain embodiments, the recombinant T cell receptor comprises a naturally occurring TCR cloned from a T cell isolated from a subject. In certain embodiments, the recombinant TCR comprises a heterodimer comprising a TCR alpha (TCRα) polypeptide and a TCR beta (TCRβ) polypeptide (i.e., a TCRαβ). In certain embodiments, the recombinant TCR comprises a heterodimer comprising a TCR gamma (TCRγ) polypeptide and a TCR delta (TCRδ) polypeptide (i.e., a TCRγδ).

In certain embodiments, the recombinant TCRαβ comprises a cloned TCRαβ isolated from a subject and specific for a peptide antigen derived from a desired target. In certain embodiments, the subject is a mammal. In certain embodiments, the mammal is a human. In certain embodiments, the desired target is a tumor-specific antigen selected from the group consisting of CD19, CD20, CD22, carcinoembryonic antigen, alphafetoprotein, CA-125, MUC-1, epithelial tumor antigen, melanoma-associated antigen, mutated p53, mutated ras, HER2/Neu, ERBB2, folate binding protein, HIV-1 envelope glycoprotein gp120, HIV-1 envelope glycoprotein gp41, GD2, CD123, CD23, CD30, CD56, c-Met, mesothelin, GD3, HERV-K, IL-11Ralpha, kappa chain, lambda chain, CSPG4, ERBB2, EGFRvIII, and VEGFR2. In certain embodiments, the recombinant TCRγδ comprises a cloned TCRγδ isolated from a subject and specific for a peptide antigen derived from a desired target. In certain embodiments, the subject is a mammal. In certain embodiments, the mammal is a human. In certain embodiments, the desired target is a tumor-specific antigen selected from the group consisting of CD19, CD20, CD22, carcinoembryonic antigen, alphafetoprotein, CA-125, MUC-1, epithelial tumor antigen, melanoma-associated antigen, mutated p53, mutated ras, HER2/Neu, ERBB2, folate binding protein, HIV-1 envelope glycoprotein gp120, HIV-1 envelope glycoprotein gp41, GD2, CD123, CD23, CD30, CD56, c-Met, mesothelin, GD3, HERV-K, IL-11Ralpha, kappa chain, lambda chain, CSPG4, ERBB2, EGFRvIII, and VEGFR2.

Further provided herein are methods for the use of the $T_{RM}$-like cells provided herein for adoptive cellular therapies, such as for treating cancer or viral disease. The cells may be used for immunosuppression, such as for subjects with graft versus host disease (GVHD), tissue or organ rejection, or an autoimmune condition.

TABLE 1

Tissue resident memory cell-associated genes assessed in transcriptional analysis.

| | Gene | Expression in $T_{RM}$ | Significance/ Proposed Function | References |
|---|---|---|---|---|
| Human $T_{RM}$ Core Signature | CD69 | upregulated | Constitutively expressed by $T_{RM}$; may promote tissue retention via S1PR1 antagonism | [3, 4, 5] |
| | ITGAE (CD103) | upregulated | Constitutively expressed by $T_{RM}$; induced by TGF-β; may promote tissue retention via interaction with e-cadherin | [3, 4, 5] |
| | ITGA1 (CD49a) | upregulated | May promote tissue retention via interaction with collagen IV | [3, 4, 5] |
| | PDCD1 (PD-1) | upregulated | High expression could dampen response to prevent tissue damage | [3, 4, 5] |

TABLE 1-continued

Tissue resident memory cell-associated genes assessed in transcriptional analysis.

| | Gene | Expression in $T_{RM}$ | Significance/ Proposed Function | References |
|---|---|---|---|---|
| | CD101 | upregulated | High expression could dampen response to prevent tissue damage | [3] |
| | CXCR6 | upregulated | Unclear | [3, 4, 5] |
| | CX3CR1 | downregulated | Unclear | [3, 4, 5] |
| | CTLA4 | upregulated | High expression could dampen response to prevent tissue damage | [4] |
| Tissue Retention | S1PR1 | downregulated | Downregulation inhibits recirculation | [3, 4, 6] |
| | KLF2 | downregulated | Downregulation suppressed S1PR1 and SELL | [3, 6] |
| | SELL (CD62L) | downregulated | Downregulation inhibits recirculation | [3] |
| | CCR7 | downregulated | Downregulation inhibits recirculation | [7] |
| Transcription Factors | EOMES | downregulated | Downregulation required for TGF-β responsiveness | [4, 7, 8] |
| | TBX21 (T-bet) | downregulated | Downregulation required for TGF-β responsiveness | [7, 8] |
| | TCF7 (TCF1) | downregulated | Downregulation may prevent development of circulating memory T-cells | [7, 9] |
| | IRF4 | upregulated | Undefined | [3] |
| | RUNX3 | upregulated? | Key regulator of TRM differentiation | [10] |
| Effector Molecules | IFNG | upregulated | Constitutive expression could enable more rapid effector response | [3, 5] |
| | TNFA | upregulated | | [5] |
| | GZMB | upregulated | | [5] |

I. DEFINITIONS

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification. "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more. The terms "about", "substantially" and "approximately" mean, in general, the stated value plus or minus 5%.

An "autoimmune disease" refers to a disease in which the immune system produces an immune response (for example, a B-cell or a T-cell response) against an antigen that is part of the normal host (that is, an autoantigen), with consequent injury to tissues. An autoantigen may be derived from a host cell, or may be derived from a commensal organism such as the micro-organisms (known as commensal organisms) that normally colonize mucosal surfaces.

The term "Graft-Versus-Host Disease (GVHD)" refers to a common and serious complication of bone marrow or other tissue transplantation wherein there is a reaction of donated immunologically competent lymphocytes against a transplant recipient's own tissue. GVHD is a possible complication of any transplant that uses or contains stem cells from either a related or an unrelated donor. In some embodiments, the GVHD is chronic GVHD (cGVHD).

As used herein, the terms "chimeric antigen receptor", "CAR", "chimeric T cell receptor", "artificial T cell receptor" or "chimeric immunoreceptor" refer to an engineered chimeric receptor construct grafting a desired non-MHC-restricted antigen-binding specificity onto an immune effector cell, e.g., an effector T cell. CARs may comprise, for example, an extracellular antigen-binding domain (e.g., an antibody or an antibody fragment such as, for example, a single-chain variable fragment (scFv) having the desired antigen specificity), a spacer sequence, a transmembrane domain, and one or more intracellular signaling domains. Exemplary intracellular signaling domains may comprise one or more intracellular tyrosine-based activation motifs ("ITAMs"), such as CD3-zeta (CD3ζ), and/or one or more costimulatory signaling domains, such as, for example, CD28, 4-1BB/CD137, ICOS, OX40, or combinations thereof.

As used herein, the terms "treat", "treatment", "treating", and the like refer to the process of ameliorating, lessening, or otherwise mitigating the symptoms of a disease or condition in a subject by, for example, administering a therapeutic agent to the subject, or by performing a surgical, clinical, or other medical procedure on the subject.

As used herein, the terms "subject" or "patient" are used interchangeably herein to refer to an individual, e.g., a human or a non-human organism, such as a primate, a mammal, or a vertebrate.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds disclosed herein which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2] oct-2-ene-1carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, lauryl sulfuric acid, maleic acid, malic acid, malonic acid, mandelic acid, methanesulfonic acid, muconic-acid, o-(4-hydroxybenzoyl)benzoic acid, oxalic acid, p-chlorobenzenesulfonic-acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic-acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine- and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts, Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

The term "culturing" refers to the in vitro maintenance, differentiation, and/or propagation of cells in suitable media. By "enriched" is meant a composition comprising cells present in a greater percentage of total cells than is found in the tissues where they are present in an organism An "isolated" biological component (such as a portion of hematological material, such as blood components) refers to a component that has been substantially separated or purified away from other biological components of the organism in which the component naturally occurs. An isolated cell is one which has been substantially separated or purified away from other biological components of the organism in which the cell naturally occurs.

II. METHODS OF USE

In some embodiments, the present disclosure provides methods for adoptive cell therapy comprising administering an effective amount of the $T_{RM}$ cells of the present disclosure. In certain embodiments of the present disclosure, cancer or viral disease is treated by adoptive transfer of a $T_{RM}$ cell population that elicits an immune response. In some embodiments, $T_{RM}$ cell population itself will mediate an immune response. Once activate in vivo the TRP cells may produce various pro-inflammatory factors, such as chemokines and cytokines, that would elicit an immune response, the Provided herein are methods for treating or delaying progression of cancer in an individual comprising administering to the individual an effective amount a $T_{RM}$ cell population. The present methods may be applied for the treatment of immune disorders, solid cancers, hematologic cancers, and viral infections. For example, a viral infection for treatment according to the embodiments may be an HIV, HBV or Herpes virus infection.

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow. T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma, adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchioloalveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma, endometroid carcinoma; skin appendage carcinoma; apocrine adenocarcinoma; sebaceous adenocarcinoma; ceruminous adenocarcinoma; mucoepidennoid carcinoma; cystadenocarcinoma; papillary cystadenocarcinoma; papillary serous cystadenocarcinoma; mucinous cystadenocarcinoma; mucinous adenocarcinoma; signet ring cell carcinoma, infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant: dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukcmia; lymphosarcoma cell leukemia; myeloid leukemia; basophilic leukemia; cosinophilic leukemia; monocytic leukemia; mast cell leukemia; megakaryoblastic leukemia; myeloid sarcoma; hairy cell leukemia; chronic lymphocytic leukemia (CLL); acute lymphoblastic leukemia (ALL); acute myeloid leukemia (AML); and chronic myeloblastic leukemia.

Particular embodiments concern methods of treatment of leukemia. Leukemia is a cancer of the blood or bone marrow and is characterized by an abnormal proliferation (production by multiplication) of blood cells, usually white blood cells (leukocytes). It is part of the broad group of diseases called hematological neoplasms. Leukemia is a broad term covering a spectrum of diseases. Leukemia is clinically and pathologically classified as acute and chronic disease.

In certain embodiments of the present disclosure, $T_{RM}$ cells are delivered to an individual in need thereof, such as an individual that has cancer or an infection, such as a bacterial or viral infection. The cells then enhance the individual's immune system to attack the respective cancer or pathogenic cells. In some cases, the individual is provided with one or more doses of the cells. In cases where the individual is provided with two or more doses of the immune cells, the duration between the administrations should be sufficient to allow time for propagation in the individual, and in specific embodiments the duration between doses is 1, 2, 3, 4, 5, 6, 7, or more days.

Certain embodiments of the present disclosure provide methods for treating or preventing an immune-mediated disorder. In one embodiment, the subject has an autoimmune disease. Non-limiting examples of autoimmune diseases include: alopecia aruata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac spate-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease. Crohn's disease, discoid lupus, essential mixed cryoglobulinemia, fibromyalgia-fibromyositis, glomerulonephritis, Graves' disease, Guillain-Barre. Hashimoto's thyroiditis, idiopathic pulmonary fibrosis, idiopathic thrombocytopenia purpura (ITP), IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, nephrotic syndrome (such as minimal change disease, focal glomerulosclerosis, or membranous nephropathy), pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomenon. Reiter's syndrome, Rheumatoid arthritis, sarcoidosis, scleroderma, Sjogren's syndrome, stiff-man syndrome, systemic lupus erythematosus, lupus erythematosus, ulcerative colitis, uveitis, vasculitides (such as polyarteritis nodosa, takayasu arteritis, temporal arteritis/giant cell arteritis, or dermatitis herpetiformis vasculitis), vitiligo, and Wegener's granulomatosis. Thus, some examples of an autoimmune disease that can be treated using the methods disclosed herein include, but are not limited to, multiple sclerosis, rheumatoid arthritis, systemic lupus erythematosis, type I diabetes mellitus, Crohn's disease; ulcerative colitis, myasthenia gravis, glomerulonephritis, ankylosing spondylitis, vasculitis, or psoriasis. The subject can also have an allergic disorder such as Asthma.

In yet another embodiment, the subject is the recipient of a transplanted organ or stem cells and $T_{RM}$ cells are used to prevent and/or treat rejection. In particular embodiments, the subject has or is at risk of developing graft versus host disease. GVHD is a possible complication of any transplant that uses or contains stem cells from either a related or an unrelated donor. There are two kinds of GVHD, acute and chronic. Acute GVHD appears within the first three months following transplantation. Signs of acute GVHD include a reddish skin rash on the hands and feet that may spread and become more severe, with peeling or blistering skin. Acute GVHD can also affect the stomach and intestines, in which case cramping, nausea, and diarrhea are present. Yellowing of the skin and eyes (jaundice) indicates that acute GVHD has affected the liver. Chronic GVHD is ranked based on its severity: stage/grade 1 is mild; stage/grade 4 is severe. Chronic GVHD develops three months or later following transplantation. The symptoms of chronic GVHD are similar to those of acute GVHD, but in addition, chronic GVHD may also affect the mucous glands in the eyes, salivary glands in the mouth, and glands that lubricate the stomach lining and intestines. Any of the populations of immune cells disclosed herein can be utilized. Examples of a transplanted organ include a solid organ transplant, such as kidney, liver, skin, pancreas, lung and/or heart, or a cellular transplant such as islets, hepatocytes, myoblasts, bone marrow, or hematopoietic or other stem cells. The transplant can be a composite transplant, such as tissues of the face. Immune cells can be administered prior to transplantation, concurrently with transplantation, or following transplantation. In some embodiments, the immune cells are administered prior to the transplant, such as at least 1 hour, at least 12 hours, at least 1 day, at least 2 days, at least 3 days, at least 4 days, at least 5 days, at least 6 days, at least 1 week, at least 2 weeks, at least 3 weeks, at least 4 weeks, or at least 1 month prior to the transplant. In one specific, non-limiting example, administration of the therapeutically effective amount of immune cells occurs 3-5 days prior to transplantation.

In some embodiments, the subject can be administered nonmycloablative lymphodepleting chemotherapy prior to the $T_{RM}$ cell population. The nonmyeloablative lymphodepleting chemotherapy can be any suitable such therapy, which can be administered by any suitable route. The nonmyeloablative lymphodepleting chemotherapy can comprise, for example, the administration of cyclophosphamide and fludarabine, particularly if the cancer is melanoma, which can be metastatic. An exemplary route of administering cyclophosphamide and fludarabine is intravenously. Likewise, any suitable dose of cyclophosphamide and fludarabine can be administered. In particular aspects, around 60 mg/kg of cyclophosphamide is administered for two days after which around 25 mg/M2 fludarabine is administered for five days.

In certain embodiments, a growth factor that promotes the growth and activation of the $T_{RM}$ cell population is administered to the subject either concomitantly with the $T_{RM}$ cell population or subsequently to the immune cells. The growth factor can be any suitable growth factor that promotes the growth and activation of the $T_{RM}$ cell population. Examples of suitable immune cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2.

Therapeutically effective amounts of $T_{RM}$ cells can be administered by a number of routes, including parenteral administration, for example, intravenous, intraperitoneal, intramuscular, intrasternal, or intraarticular injection, or infusion.

The therapeutically effective amount of $T_{RM}$ cells for use in adoptive cell therapy is that amount that achieves a desired effect in a subject being treated. For instance, this can be the amount of $T_{RM}$ cells necessary to inhibit advancement, or to cause regression of an autoimmune or alloimmune disease, or which is capable of relieving symptoms caused by an autoimmune disease, such as pain and inflammation. It can be the amount necessary to relieve symptoms associated with inflammation, such as pain, edema and elevated temperature. It can also be the amount necessary to diminish or prevent rejection of a transplanted organ.

The $T_{RM}$ cells can be administered in treatment regimens consistent with the standard of care for treating the disease, for example a single or a few doses over one to several days to ameliorate a disease state or periodic doses over an extended time to inhibit disease progression and prevent disease recurrence. The precise dose to be employed in the formulation will also depend on the route of administration, and the seriousness of the disease or disorder, and should be decided according to the judgment of the practitioner and each patient's circumstances. The therapeutically effective amount of immune cells will be dependent on the subject being treated, the severity and type of the affliction, and the manner of administration. In some embodiments, doses that could be used in the treatment of human subjects range from at least $3.8 \times 10^4$, at least $3.8 \times 10^5$, at least $3.8 \times 10^6$, at least $3.8 \times 10^8$, at least $3.8 \times 10^8$, at least $3.8 \times 10^9$, or at least $3.8 \times 10^{10}$ immune cells/m². In a certain embodiment, the dose used in the treatment of human subjects ranges from about $3.8 \times 10^9$ to about $3.8 \times 10^{10}$ immune cells/m². In additional embodiments, a therapeutically effective amount of immune cells can vary from about $5 \times 10^6$ cells per kg body weight to about $7.5 \times 10^8$ cells per kg body weight, such as about $2 \times 10^7$ cells to about $5 \times 10^8$ cells per kg body weight, or about $5 \times 10^7$ cells to about $2 \times 10^8$ cells per kg body weight. The exact amount of immune cells is readily determined by one of skill in the art based on the age, weight, sex, and physiological condition of the subject. Effective doses can be extrapolated from dose-response curves derived from in vitro or animal model test systems.

The $T_{RM}$ cells may be administered in combination with one or more other therapeutic agents for the treatment of the immune-mediated disorder. Combination therapies can include, but are not limited to, one or more anti-microbial agents (for example, antibiotics, anti-viral agents and anti-fungal agents), anti-tumor agents (for example, fluorouracil, methotrexate, paclitaxel, fludarabine, etoposide, doxorubicin, or vincristine), immune-depleting agents (for example, fludarabine, etoposide, doxorubicin, or vincristine), immunosuppressive agents (for example, azathioprine, or glucocorticoids, such as dexamethasone or prednisone), anti-inflammatory agents (for example, glucocorticoids such as hydrocortisone, dexamethasone or prednisone, or non-steroidal anti-inflammatory agents such as acetylsalicylic acid, ibuprofen or naproxen sodium), cytokines (for example, interleukin-10 or transforming growth factor-beta), hormones (for example, estrogen), or a vaccine. In addition, immunosuppressive or tolerogenic agents including but not limited to calcineurin inhibitors (e.g., cyclosporin and tacrolimus); mTOR inhibitors (e.g., Rapamycin); mycophenolate mofetil, antibodies (e.g., recognizing CD3, CD4, CD40, CD154, CD45, IVIG, or B cells); chemotherapeutic agents (e.g., Methotrexate. Treosulfan, Busulfan); irradiation; or chemokines, interleukins or their inhibitors (e.g., BAFF, IL-2, anti-IL-2R, IL-4, JAK kinase inhibitors) can be administered. Such additional pharmaceutical agents can be administered before, during, or after administration of the immune cells, depending on the desired effect. This administration of the cells and the agent can be by the same route or by different routes, and either at the same site or at a different site.

A. Combination Therapies

In certain embodiments, the methods provided herein further comprise a step of administering at least one additional therapeutic agent to the subject. All additional therapeutic agents disclosed herein will be administered to a subject according to good clinical practice for each specific composition or therapy, taking into account any potential toxicity, likely side effects, and any other relevant factors.

In certain embodiments, the additional therapy may be immunotherapy, radiation therapy, surgery (e.g., surgical resection of a tumor), chemotherapy, bone marrow transplantation, or a combination of the foregoing. The additional therapy may be targeted therapy. In certain embodiments, the additional therapy is administered before the primary treatment (i.e., as adjuvant therapy). In certain embodiments, the additional therapy is administered after the primary treatment (i.e., as neoadjuvant therapy).

In certain embodiments, the additional therapy comprises an immunotherapy. In certain embodiments, the immunotherapy comprises an immune checkpoint inhibitor. In certain embodiments, the immune checkpoint inhibitor inhibits an immune checkpoint protein selected from the group consisting of programmed cell death pathway 1 (PD-1/CD279) and its ligands (PD-L1/CD274 and PD-L2/CD273), cytotoxic T lymphocyte-associated antigen 4 (CTLA-4/CD152), lymphocyte-activation gene 3 (LAG-3/CD223), B and T lymphocyte attenuator (BTLA), T cell immunoreceptor with Ig and immunoreceptor tyrosine-based inhibitory motif (TM) domains (TIGIT), T cell immunoglobulin domain and mucin domain 3 (TIM-3/HAVcr2), killer immunoglobulin-like receptor (KIR/CD158), V-domain immunoglobulin suppressor of T cell activation (VISTA), and the adenosine A2a receptor (A2aR). In some aspects, the immunotherapy is a 4-1BB agonist. Exemplary 4-1BB agonists include but are not limited to 4-1BB agonist antibodies (e.g., Utomilumab), recombinant 4-1BB (including but not limited to soluble, matrix-bound, scaffold bound forms), and 4-1BB aptamers.

In certain embodiments, the immune checkpoint inhibitor is a PD-1 binding antagonist. In certain embodiments, the PD-1 binding antagonist is an anti-PD-1 antibody. In certain embodiments, the anti-PD-1 antibody is selected from the group consisting of nivolumab, pembrolizumab, and CT-011. In certain embodiments, the PD-1 binding antagonist is an immunoadhesin (e.g., an immunoadhesin comprising an extracellular or PD-1 binding portion of PDL1 or PDL2 fused to an immunoglobulin constant region (e.g., an Fc region of an immunoglobulin sequence).

In certain embodiments, the immune checkpoint inhibitor is a CTLA-4 binding antagonist. In certain embodiments, the CTLA-4 binding antagonist is an anti-CTLA-4 antibody. In certain embodiments, the anti-CTLA-4 antibody is selected from the group consisting of ipilimumab and tremelimumab.

In certain embodiments, the additional therapeutic agent comprises treatment with radiotherapy. In certain embodiments, the radiotherapy is selected from the group consisting of gamma rays (γ-rays), X-rays, microwaves, proton beam irradiation, ultraviolet irradiation, and the directed delivery of radioisotopes to the tumor. In certain embodiments, the radiotherapy comprises treatment with X-rays. In certain embodiments, the X-rays are administered in daily doses of 50 to 200 roentgens over a period of three to four weeks. In certain embodiments, the X-rays are administered in a single dose of 2000 to 6000 roentgens. In certain embodiments, the radiotherapy comprises directed delivery of radioisotopes to the tumor. Dosage ranges for radioisotopes vary widely depending on the half-life of the isotope, the strength and type of radiation emitted, and the degree of uptake by tumor cells, but determination of an appropriate therapeutically effective dose is within the level of ordinary skill in the art.

In certain embodiments, the additional therapeutic agent comprises administration of agents for the treatment of side-effects associated with the primary treatment (e.g., nausea, cachexia, and the like). In certain embodiments, the additional therapy comprises an immunotherapy. In certain embodiments, the additional therapy comprises radiation therapy. In some embodiments, the radiotherapy comprises gamma irradiation. In certain embodiments, the additional therapy comprises surgery. In certain embodiments, the additional therapy comprises a combination of radiation therapy and surgery. In certain embodiments, the additional therapy comprises treatment with a class of chemotherapeutic agent selected from the group consisting of alkylating agents, anthracyclines, cytoskeletal disruptors, epothilones, histone deacetylase inhibitors, topoisomerase I inhibitors, topoisomerase II inhibitors, kinase inhibitors, nucleotide analogs and nucleotide precursor analogs, peptide antibiotics, platinum-based compounds, retinoids, *vinca* alkaloids and derivatives thereof.

The additional therapies contemplated herein may be administered before, after, or concurrently with administration of the compositions provided herein. In certain embodiments, the additional therapy is administered before the compositions provided herein. In certain embodiments, the additional therapy is administered after the compositions provided herein. In certain embodiments, the additional therapy is administered at one or more intervals before or after administration of the compositions provided herein. Determination of an appropriate interval for administration of an additional therapy such that the subject being treated benefits from the combination therapy is within the level of ordinary skill in the art.

B. Pharmaceutical Compositions

In another aspect, provided herein are pharmaceutical compositions and formulations comprising $T_{RM}$ cells and a pharmaceutically acceptable carrier.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences $22^{nd}$ edition, 2012), in the form of aqueous solutions, such as normal saline (e.g., 0.9%) and human serum albumin (e.g., 10%). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin. gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zinc-protein complexes); and/or non-ionic surfactants such as polyethylene glycol (PEG).

III. KITS

In some embodiments, a kit that can include, for example, one or more media and components for the production of $T_{RM}$ cells is provided. Such formulations may comprise a cocktail of factors, in a form suitable for combining with Tam cells. The reagent system may be packaged either in aqueous media or in lyophilized form, where appropriate. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The components of the kit may be provided as dried powder(s). When reagents and/or components are provided as a dry powder, the powder can be reconstituted by the addition of a suitable solvent. It is envisioned that the solvent may also be provided in another container means. The kits also will typically include a means for containing the kit component(s) in close confinement for commercial sale. Such containers may include injection or blow molded plastic containers into which the desired vials are retained. The kit can also include instructions for use, such as in printed or electronic format, such as digital format.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Production of Tissue Resident Memory T Cells

Peripheral blood samples were obtained from healthy human subjects. The blood was sorted using FACS to isolate native (CD45RA+CCR7$^+$) CD8$^+$ T cells. The T cells were then polyclonally activated for 4 days in atmospheric oxygen (approximately 20%) or hypoxia (2% $O_2$) to generate "early effectors". The early effectors were then cultured for an additional 2 days in the presence of 1.25 ng/mL rhTGF-β1. The cells were then harvested and analyzed for expression of $T_{RM}$-associated genes and surface markers.

Figures 2A, 2B:
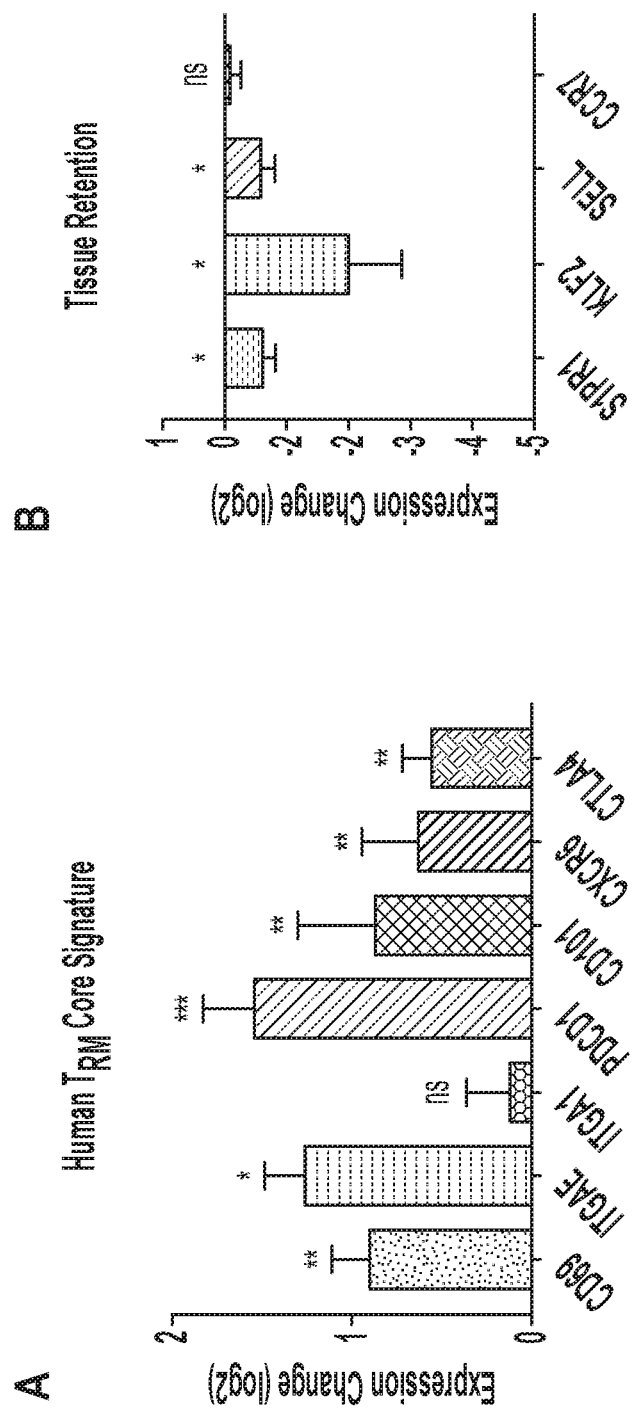
Figure 3A:
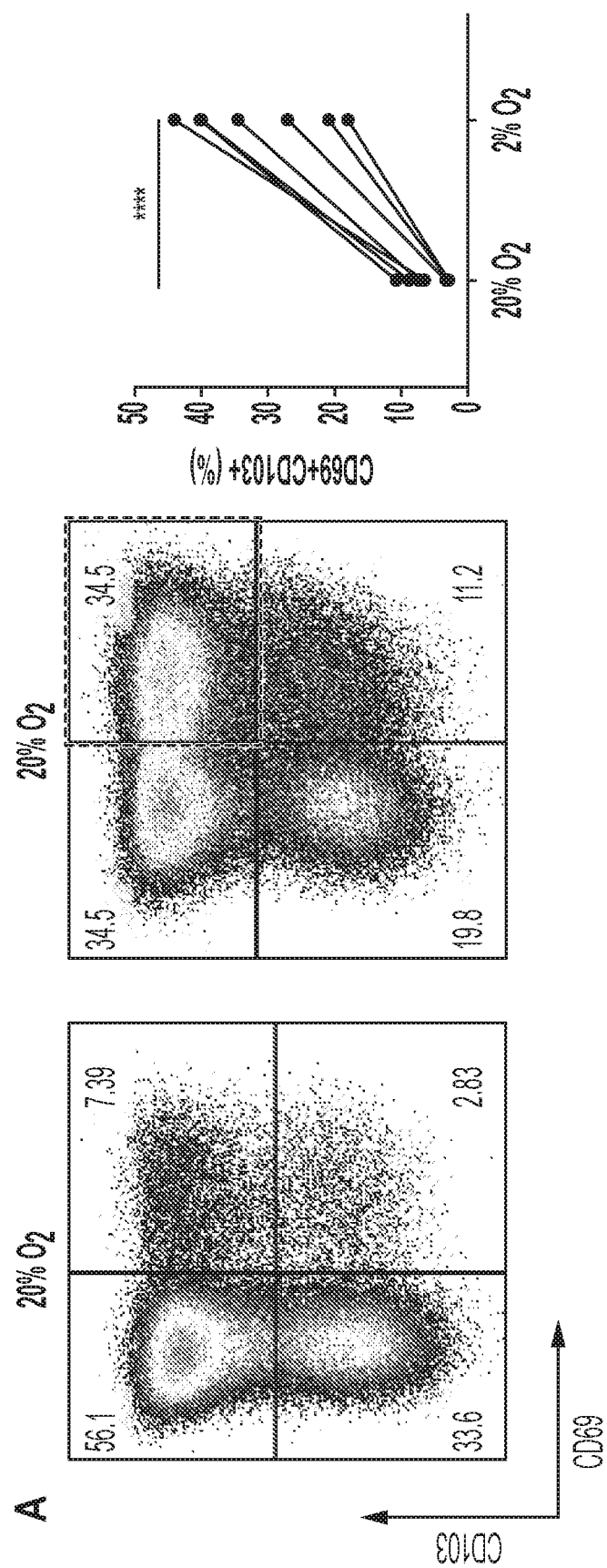
FIGS. 3A-3C: Hypoxia in combination with TGF-β1 induces a CD69$^+$CD103$^+$ population that expresses human Tαω-associated markers. Naïve CD8$^+$ T-cells isolated from peripheral blood of healthy human donors were activated in atmospheric oxygen (approximately 20%) or hypoxia (2% oxygen) for 4 days and then for an additional 2 days with the addition of rhTGF-β1. (A) The frequency of the CD69$^+$ CD103$^+$ $T_{RM}$-like population and (B and C) expression of $T_{RM}$-associated markers was then assessed by flow cytometry. Representative results from 1 donor are shown in (B), gray histograms represent fluorescence minus one (FMO) control. n=7, 3 independent experiments: ratio paired t-test (A) or ANOVA (C); *P<0.05, P<0.01. *P<0.001. ***P<0.0001.

It was found that hypoxia in combination with TGF-1 induced a CD69$^+$CD103$^+$ population that expressed human $T_{RM}$-associated markers, including CD69 and CD103 (FIG. 3). The $T_{RM}$-like T cells were further analyzed for changes in expression of additional genes. It was found that the cells cultured in hypoxia versus atmospheric oxygen conditions had changes in gene expression associated with the $T_{RM}$ phenotype (FIG. 2).

Naïve CD8$^+$ T-cells were activated by hypoxia with or without the addition of rhTGF-β1. The frequency of the CD69$^+$CD103$^+$ population was assessed by flow cytometry. It was observed that hypoxia and TGF-β1 synergize to induce CD69$^+$CD103$^+$ cells (FIG. 4).

Figure 9A:
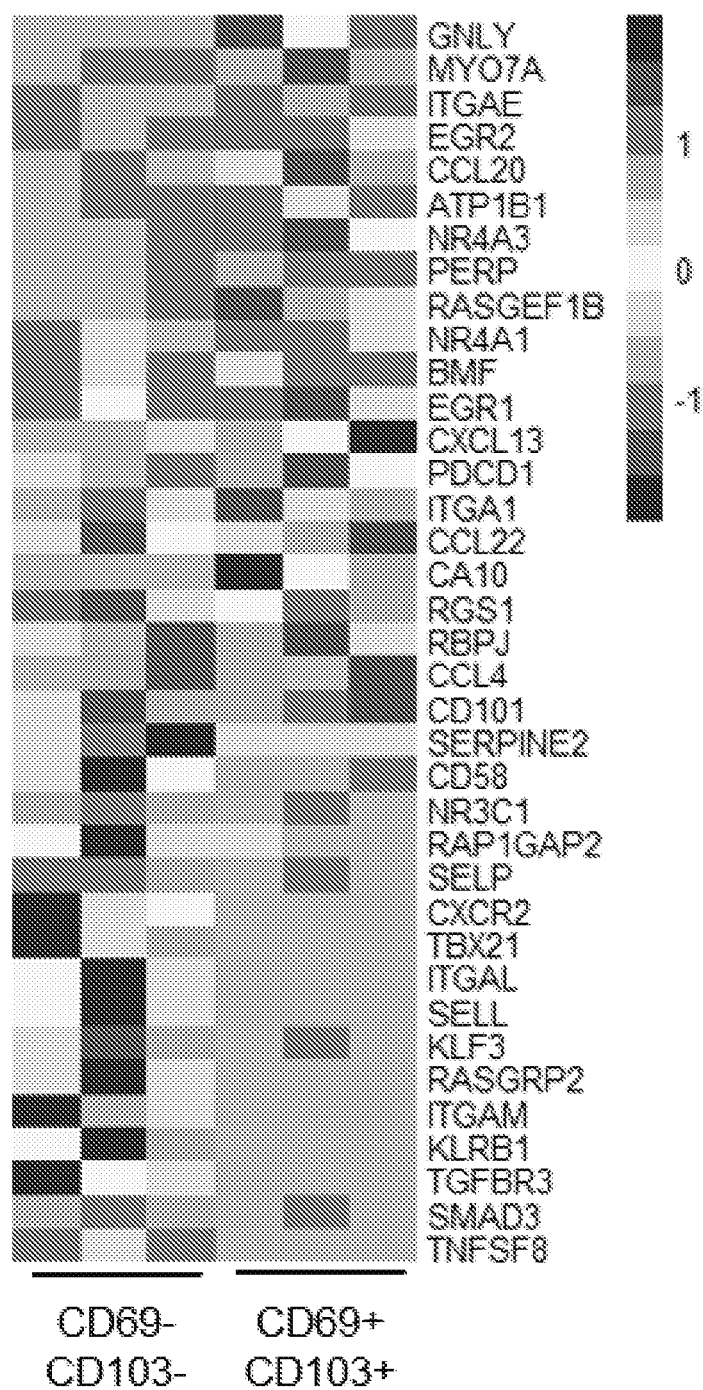
FIGS. 9A-9B: Hypoxia and TGF-β1 induced $T_{RM}$-phenotype cells show transcriptional differences similar to those reported for endogenous $T_{RM}$. CD69$^-$CD103$^-$, CD69$^+$ CD103$^-$, and CD69$^+$CD103$^+$ T-cells were generated as described in FIG. 4 and sorted before isolation of RNA for transcriptome analysis via RNA-sequencing (n=3). (A) Heatmap showing expression of selected genes commonly reported in transcriptome analyses of endogenous human TR. (B) Heatmap comparing transcriptional differences (log 2FC) in CD8$^+$CD69$^+$ versus CD8$^+$CD69$^-$ T cells from human lung (see Kumar et al., 2017, incorporated herein by reference) and CD69$^+$CD103$^+$ hypoxia and TGF-β1 in-vitro induced TRH (i-$T_{RM}$t) versus CD69$^-$CD103$^-$ cells from normal cell culture conditions (20% O$_2$ without TGF-β1). Differential expression determined by log 2FC≥|1| and FDR<0.05.
Figure 9B:
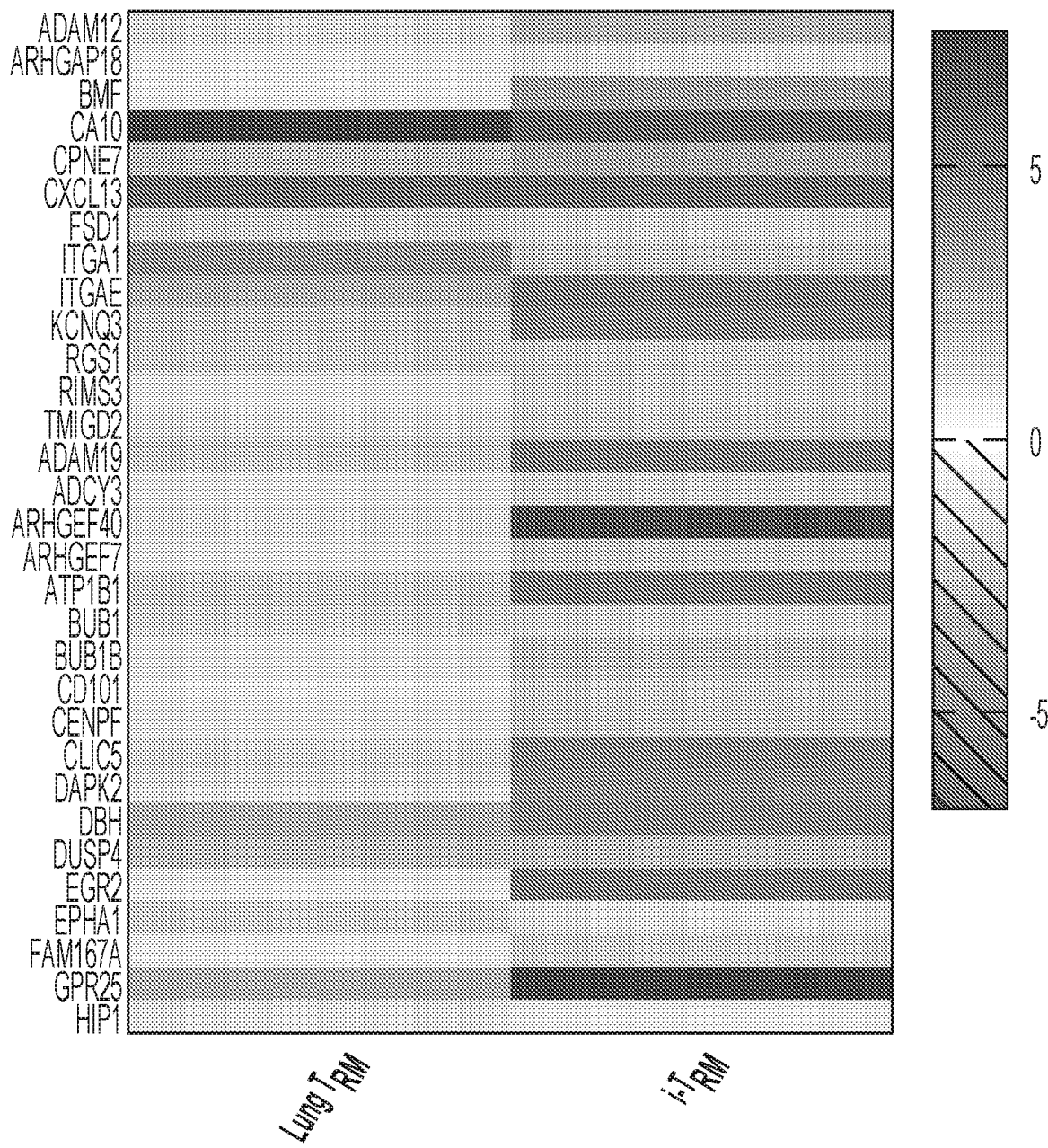
Figure 9B:
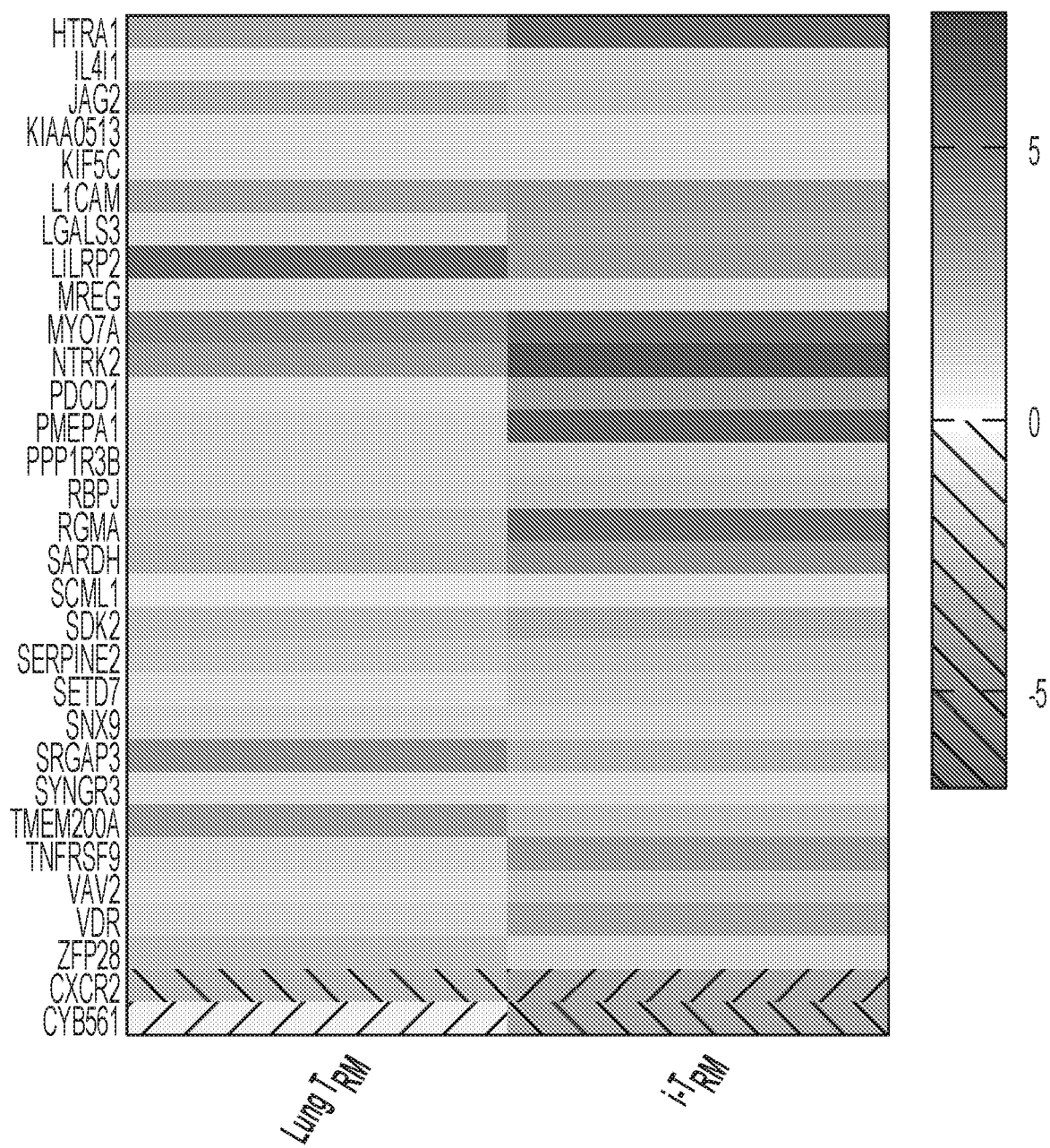
Figure 9B:
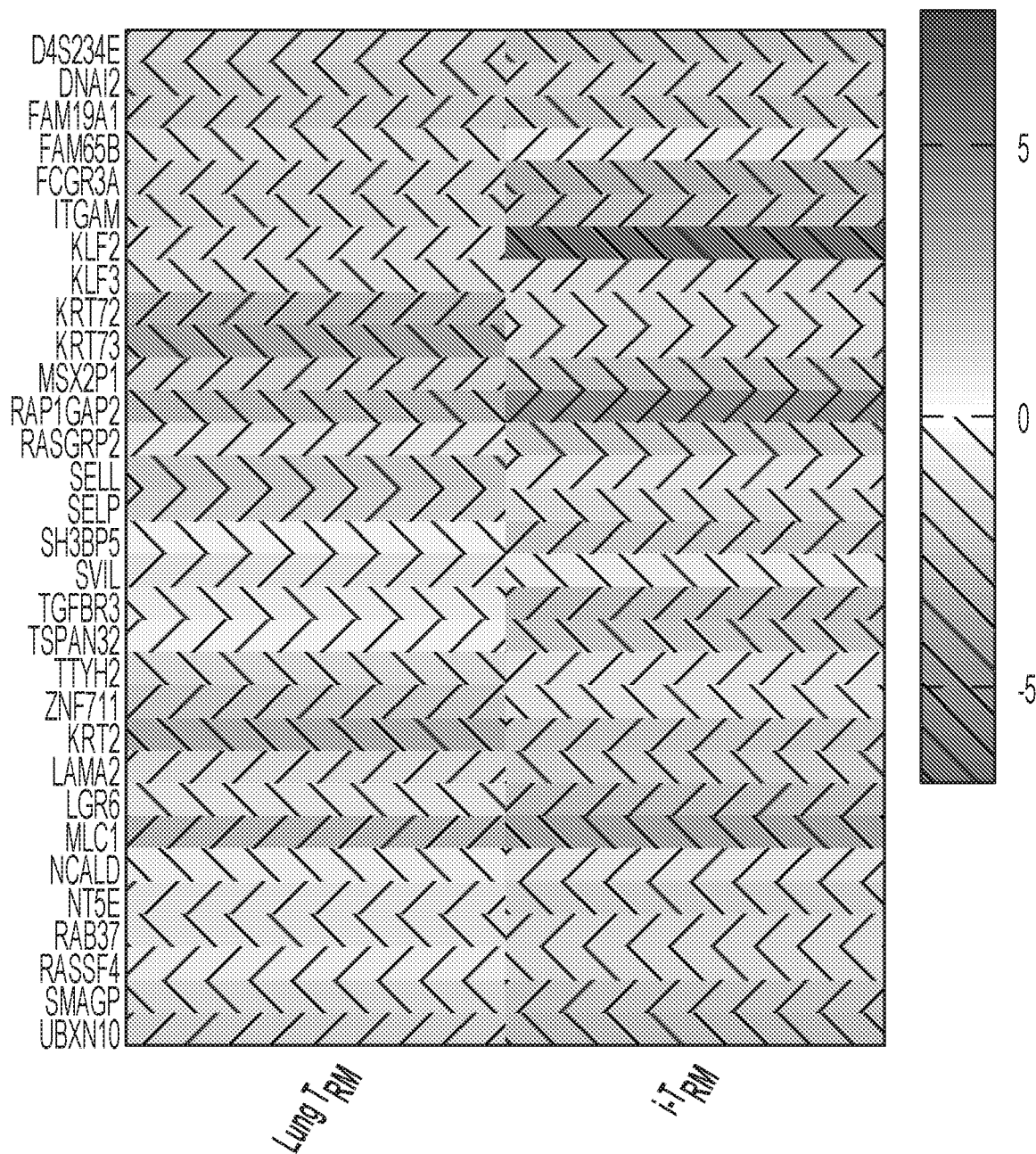

Further, it was found that hypoxia and TGF-β1 induced $T_{RM}$-phenotype cells show transcriptional differences similar to those reported for endogenous $T_{RM}$. CD69-CD103$^-$, CD69$^+$CD103$^-$, and CD69$^+$CD103$^+$ T-cells were generated and sorted before isolation of RNA for transcriptome analysis via RNA-sequencing (n=3). FIG. 9A shows a heatmap showing expression of selected genes commonly reported in transcriptome analyses of endogenous human $T_{RM}$. FIG. 9B shows a heatmap comparing transcriptional differences (log 2FC) in CD8$^+$ CD69$^+$ versus CD8$^+$ CD69$^-$ T-cells from human lung and CD69$^+$CD103$^+$ hypoxia and TGF-β1 in-vitro induced $T_{RM}$ (i-$T_{RM}$) versus CD69$^-$CD103$^-$ cells from normal cell culture conditions (20% $O_2$ without TGF-β1). Differential expression determined by |log 2FC|≥1 and FDR<0.05.

The present studies showed that hypoxia and TGF-β1 synergize to induce a CD8$^+$CD69$^+$CD103$^+$ cell population that expresses human Ta-associated markers and has a transcriptional profile similar to that of endogenous human TRH. This work reveals another possible cue for $T_{RM}$ differentiation in vivo, and provides the basis for an in vitro method to generate antigen-specific $T_{RM}$-like cells that would enable the development of adoptive cellular therapies utilizing this unique cell type. Thus, the present methods can be used to produce cells with a Tao phenotype.

Example 2—Materials and Methods

Cell isolation and in vitro cell culture: Healthy donor peripheral blood mononuclear cells (PBMCs) were collected by leukapheresis and stored in liquid nitrogen until use. All human sample collection was performed with informed consent and approved by the institutional review board (IRB) of UT MD Anderson Cancer Center. CD8$^+$ T cells were enriched from healthy donor PBMCs using StemCell EasySep™ kits. Cells were then stained with fluorochrome-conjugated antibodies against CD8, CD45RA, and CCR7. Naïve CD8+CD45RA+CCR7+ cells were sorted using a FACSAria™ III or Fusion cell sorter (BD Biosciences). Sorted naïve cells were resuspended in cell culture media (RPMI with 10% FBS, L-glutamine, and penicillin-streptomycin) with 10 IU/ml IL-2 (Prometheus) and equilibrated overnight to 2% oxygen in a hypoxic chamber (Coy Laboratory Products) or atmospheric oxygen (approx. 20%) in a standard cell culture incubator (Thermo Fisher). After equilibration cells were activated with anti-CD3/anti-CD28 beads (Dynabeads®, Gibco) for four days. On day four 1.25 ng/ml recombinant human TGF-51 (Biolegend) was added and cells were cultured for an additional two days. Antigen-specific CD8$^+$ T cells generated via stimulation with autologous peptide pulsed dendritic cells or TCR transduction followed by tetramer-based sorting were expanded using a conventional Rapid Expansion Protocol (REP) or a TRM modifying REP. Tetramer-positive cells were expanded for 10-14 days using 30 ng/mL anti-CD3 (OKT3) and 200× irradiated allogeneic PBMCs and LCLs as feeder cells in either i) 20% oxygen and supplemented with IL-2 (50 IU/ml) in the case of conventional REP or ii) in 2% oxygen and supplemented with IL-15 (10 ng/ml) and rhTGF-$0 (1.25 ng/ml, beginning on day 4) in the case of modified REP to induce TRM phenotype.

Flow cytometry: For analysis of human TRM-associated markers beads were removed from cells and cells were washed once in staining buffer and stained with Live/Dead Fixable Aqua (Life Technologies) and fluorochrome-conjugated antibodies against CD8, CD69. CD103, PD-1, CD101, CXCR6, and CD49a (all Biolegend). After staining cells were fixed in 4% paraformaldehyde Fixation Buffer (Biolegend), washed, and stored in staining buffer until analysis. Stained cells were analyzed using an ACEA Novocyte 3000 flow cytometer. Single fluorochrome-stained compensation beads (UltraComp™, eBioscience) and fluorescence minus one (FMO) samples were used as controls. Data were analyzed using FlowJo software (BD Biosciences).

Quantitative real-time PCR (qRT-PCR or qPCR): For analysis of human $T_{RM}$-associated gene expression beads were removed from cells and cells were washed once in PBS. RNA was isolated using the Qiagen RNeasy® Plus Mini Kit according to manufacturer's instructions. When necessary RNA was further purified and/or concentrated using the Qiagen RNeasy® MinElute Cleanup Kit according to manufacturer's instructions. First strand cDNA was synthesized using M-MLV Reverse Transcriptase (Thermo Fisher). Quantitative real-time PCR was performed using the QuantStudio® 5 Real-Time PCR System and PowerUp® SYBR® Green Master Mix (Applied Biosystems, ThermoFisher Scientific). Relative mRNA gene expression was normalized to the housekeeping gene RPL13A. Primers used are listed in the table below.

TABLE 2

Primer sequences.

| Gene | Primer | SEQ ID NO |
|---|---|---|
| CD69 F | ATTGTCCAGGCCAATACACATT | 1 |
| CD69 R | CCTCTCTACCTGCGTATCGTTTT | 2 |
| ITGAE R | AGCCATGCAACACGTCTTAGA | 3 |
| ITGAE F | TCCTCGAATATGCCACCATCG | 4 |
| ITGA1 R | CTGGACATAGTCATAGTGCTGGA | 5 |
| ITGA1 F | ACCTGTGTCTGTTTAGGACCA | 6 |
| CXCR6 F | CAAGAGCCTACTGGGCATCTACAC | 7 |
| CXCR6 R | TGGCCTTAACCACTACAATGAAAC | 8 |
| CX3CR1 F | TCACCGTCATCAGCATTGATAGG | 9 |
| CX3CR1 R | GTTTCCACATTGCGGAGCAC | 10 |
| PDCD1 F | ACGAGGGACAATAGGAGCCA | 11 |
| PDCD1 R | GGCATACTCCGTCTGCTCAG | 12 |
| CD101 F | CAGCCAGTGACGTACAGCTC | 13 |
| CD101 R | CCATTCCGTTGCCTCACAGAA | 14 |
| S1PR1 F | GCCTCTTCCTGCTAATCAGCG | 15 |
| S1PR1 R | GCAGTACAGAATGACGATGGAG | 16 |
| KLF2 F | CATCTGAAGGCGCATCTG | 17 |
| KLF2 R | CGTGTGCTTTCGGTAGTGG | 18 |
| EOMES F | GCCCACGTCTACCTGTGCAA | 19 |
| EOMES R | GGGCAGTGGGATTGAGTCCG | 20 |
| TBX21 F | CAACACAGGAGCGCACTGGA | 21 |
| TBX21 R | GTGTTGGAAGCGTTGCAGGC | 22 |
| TCF7 F | TGCAGCTATACCCAGGCTGG | 23 |
| TCF7 R | CCTCGACCGCCTCTTCTTC | 24 |
| IRF4 F | CCCGTACCAATGTCCCATGA | 25 |
| IRF4 R | CCTGTCACCTGGCAACCATTT | 26 |
| RUNX3 F | AGCACCACAAGCCACTTCAG | 27 |
| RUNX3 R | GGGAAGGAGCGGTCAAACTG | 28 |
| CCR7 F | CAAGCTGTCCTGTGTGGGCA | 29 |
| CCR7 R | CGCTCAAAGTTGCGTGCCTG | 30 |
| SELL F | ATGGAACGATGACGCCTGCC | 31 |

TABLE 2-continued

Primer sequences.

| Gene | Primer | SEQ ID NO |
|---|---|---|
| SELL R | GGCCTCCAAAGGCTCACACT | 32 |
| IFNG F | TGGAAAGAGGAGAGTGACAGAAA | 33 |
| IFNG R | TCCTTGATGGTCTCCACACTC | 34 |
| TNFA F | GGCGCTCCCCAAGAAGACAG | 25 |
| TNFA R | CAGGCTTGTCACTCGGGGTT | 36 |
| GZMB F | CAACCAATCCTGCTTCTGCT | 37 |
| GZMB R | CCGCACCTCTTCAGAGACTT | 38 |
| CTLA4 F | TGGACACGGGACTCTACATCT | 39 |
| CTLA4 R | GGCACGGTTCTGGATCAATTACA | 40 |
| SLC2A1 F | TCTGGCATCAACGCTGTCTTC | 41 |
| SLC2A1 R | CGATACCGGAGCCAATGGT | 42 |
| VEGF F | AAATGCTTTCTCCGCTCTGA | 43 |
| VEGF R | CCCACTGAGGAGTCCAACAT | 44 |
| RPL13A F | CCTCAAGGTCGTGCGTCTGA | 45 |
| RPL13A R | TCCACGTTCTTCTCGGCCTG | 46 |

RNA-sequencing transcriptome analysis: Cells were sorted using a FACSAriar™ IIIu cell sorter (BD Biosciences) before RNA isolation using the Qiagen RNeasy® Plus Mini Kit followed by the Qiagen RNeasy® MinElute Cleanup Kit. The library was constructed using the Illumina TruSeq Stranded mRNA kit. RNA sequencing was carried out using the Illumina NextSeq®500 platform. The raw reads were mapped to the *Homo sapiens* reference genome and transcriptome (GRCh38, GENCODEV23) by HISAT2 (version: 2.1.0). Htseq-count (version: 2.1.0) was used to get the counts for genes. R and Bioconductor packages DESeq2 (version 1.14.1) was used to identify the differentially expressed genes. The genes (mRNA only, taking the protein-coding genes for p-value adjustment) with FDR<0.05 and |fold-change|>2 were considered differentially expressed. R and Bioconductor package fgsea (version 1.10.0) was used to determine whether an a priori defined set of genes shows statistically significant, concordant differences between two biological states (e.g. phenotypes). Gene sets were derived from several previously published T cell signatures. The $T_{RM}$ signature was constructed from several studies. Lung Two and Breast Cancer TIL signatures were downloaded from the Gene Expression Omnibus (GEO), GSE61397 and GSE110938, respectively. False-discovery rate (FDR) adjusted p-values less than 0.05 were considered significant or "true".

Functional analysis of significantly differentially expressed genes (FDR 20<0.05 and |fold-change|>2) was done with Ingenuity® Pathway Analysis (IPA) software (version 48207413, Qiagen) using all genes in the Ingenuity Knowledge Base as the reference set and right-tailed Fisher's exact test in a core analysis to determine if pathways are significantly altered between conditions (−log 10[p value] >1.3).

Statistical analysis: Graphical presentation and statistical analysis of the data was performed using GraphPad Prism (Version 7, GraphPad software, San Diego, CA). Data are displayed as mean±SEM. Results between experimental groups were compared using statistical tests described in the figure legends (ANOVA always followed by Tukey's multiple comparisons test). $p<0.05$ was considered statistically significant.

Example 3—Hypoxia Acts as an Environmental Cue for Human Tissue Resident Memory T-Cell Differentiation Human $CD8^+$ T-cells differentiated in hypoxia and TGF-1 acquire a $T_{RM}$-like phenotype: Given the relative hypoxia in inflamed tissues, it was postulated that low oxygen tension could provide additional cues to $T_{RM}$ differentiation. To determine whether hypoxia can contribute to induction of a $T_{RM}$ phenotype naïve ($CD45RA^+$ $CCR7^+$) CD8+ T-cells were sorted from human peripheral blood, activated them for 4 days in hypoxia (2% $O_2$) or normal cell culture conditions (atmospheric oxygen, approximately 20% $O_2$) to generate "early effectors" and then cultured an additional 2 days in the presence of rhTGF-β1.

Quantitative real-time PCR (qPCR) was used to assess the bulk populations for expression of a panel of genes associated with $T_{RM}$ transcriptional profile. Cells differentiated in 2% $O_2$+TGF-β1 showed upregulation of most of the genes identified by Kumar el al. 2017 (which is incorporated herein by reference) as the core transcriptional signature of human $T_{RM}$, namely CD69, ITGAE (CD103), PDCD1 (PD-1), CD101, and CXCR6 (FIG. 2A). Notably, no difference was observed in transcript levels of ITGA1 (CD49a). In addition, transcripts of genes important in T-cell recirculation (S1PR1, KLF2, SELL (CD62L)) were downregulated, further suggesting a resident memory phenotype (FIG. 2B). Previous reports in mouse models have demonstrated that downregulation of S1PR1 and KLF2 are critical to $T_{RM}$ differentiation, and decreased levels of these genes have also been observed in endogenous human $T_{RM}$. Transcripts for the transcription factor Eomes were dramatically decreased (FIG. 2C). Studies in mice have demonstrated that extinguishment of Eomes is necessary for TGF-β1 responsiveness and establishment of $T_{RM}$ IRF4 and RUNX3 were upregulated. The specific role of IRF4 in $T_{RM}$ remains undefined but its upregulation has been reported in human $T_{RM}$. The transcription factor RUNX3 has recently been identified as a key regulator of $T_{RM}$ differentiation. Finally, elevated levels of transcripts encoding effector molecules TNF-α and granzyme b were observed, similar to findings reported in human lung $T_{RM}$ (FIG. 2D). Elevated expression of the canonical hypoxia responsive genes SLC2A1 (Glut-1) and VEGF confirmed the cells were responding to hypoxic conditions (FIG. 1E). In totality, these results indicate that when human $CD8^+$ T-cells are differentiated in hypoxia in combination with TGF-β1 they acquire a tissue resident memory-like transcriptional profile.

Figure 3B:
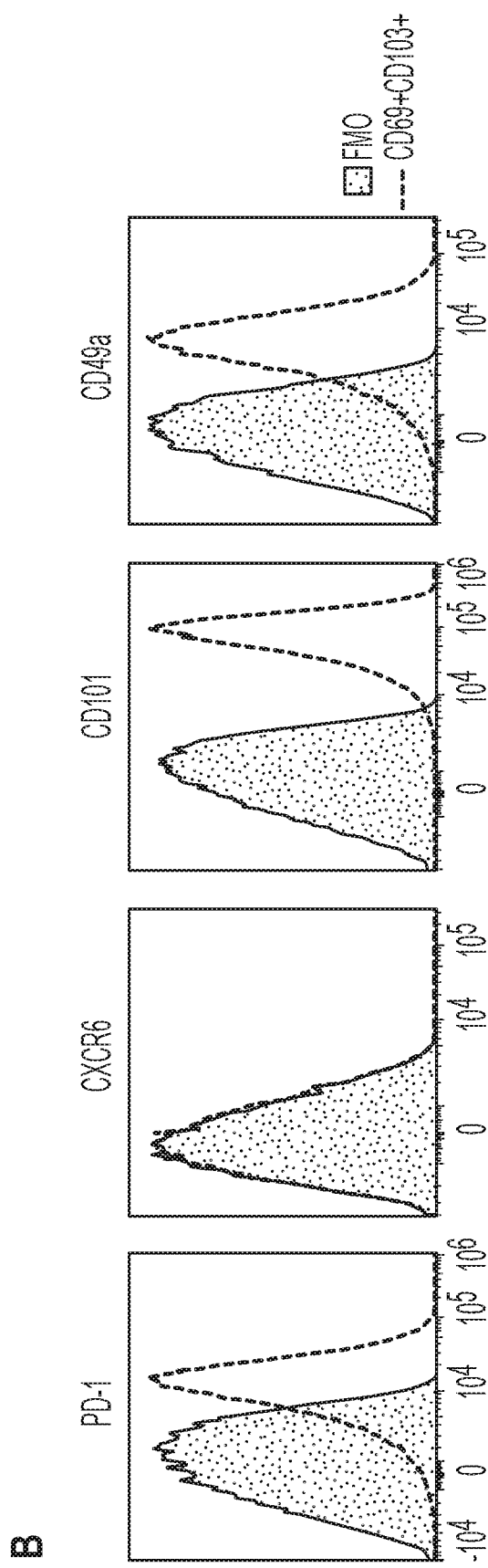
Figure 3C:
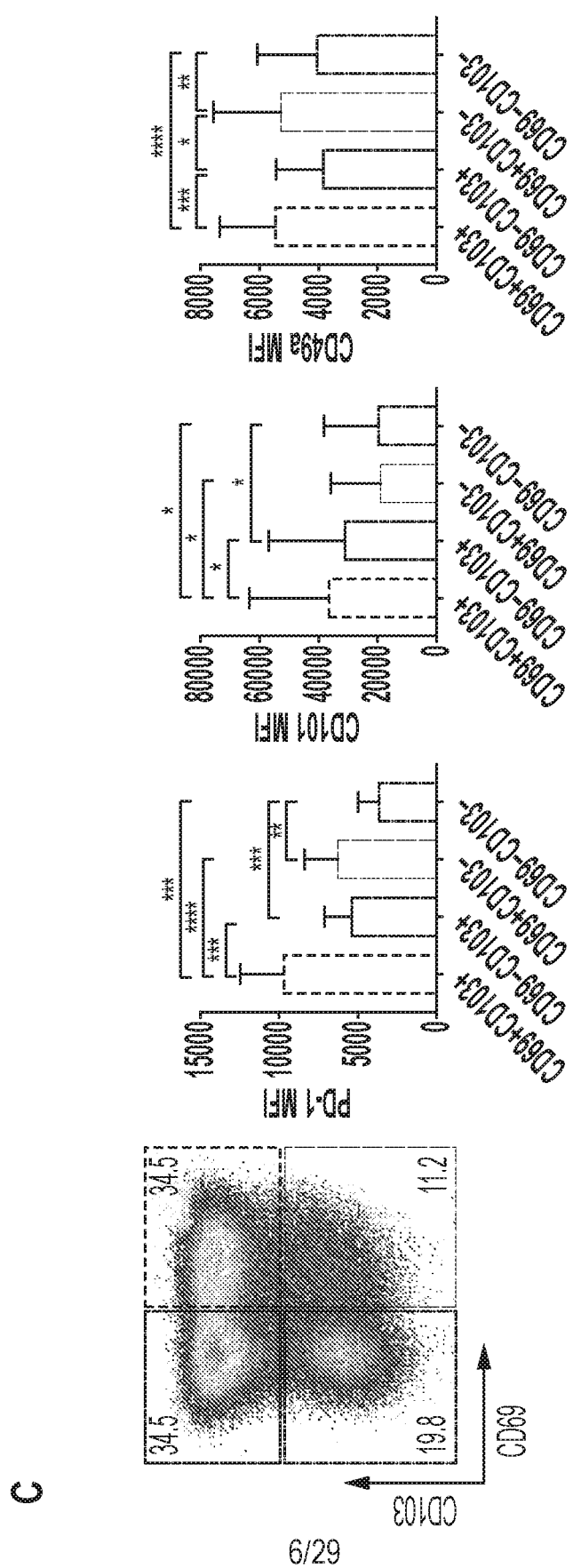

Flow cytometric analysis to evaluate protein-level expression of markers considered to be the core signature of human $T_{RM}$. In all healthy donors tested there was an increase in $CD69^+CD103^+$ cells in the 2% $O_2$+TGF-β1 condition compared to 20% $O_2$+TGF-β1 (FIG. 2A). Cell viability was comparable or better in the 2% $O_2$+TGF-β1 cells versus the 20% $O_2$+TGF-β1 cells (FIG. 7B). These $CD69^-CD103^+$ cells expressed PD-1, CD101, and CD49a (FIG. 3B). Notably, CXCR6 surface protein expression was not observed despite transcriptional upregulation. Although expression of both CD69 and CD103 is now commonly used to define $T_{RM}$ there is still debate regarding which of these surface markers is best to use to identify $T_{RM}$, in part due to heterogeneous expression of CD69 and CD103 in endogenous resident memory cells. Thus, the expression levels of the $T_{RM}$-associated markers PD-1, CD101, and CD49a were compared among the $CD69^-CD103^+$, $CD69^+CD103^+$, and $CD69^+CD103^-$ populations from the 2% $O_2$+TGF-β1 condition. As expected, the CD69+CD103+ population had the highest levels of PD-1 and CD101 surface expression (FIG. 3C). Expression of CD49a was also high but equivalent to expression levels observed in the $CD69^+CD103^-$ population. In comparing different oxygen conditions, the most dramatic increase in population fold change was found to be in the $CD69^+CD103^+$ population (FIG. 7C, 7D). On the basis of these results, it was chosen to focus further analysis on the $CD69^+CD103^+$ population as the in vitro induced $T_{RM}$ cells.

Figure 8F:
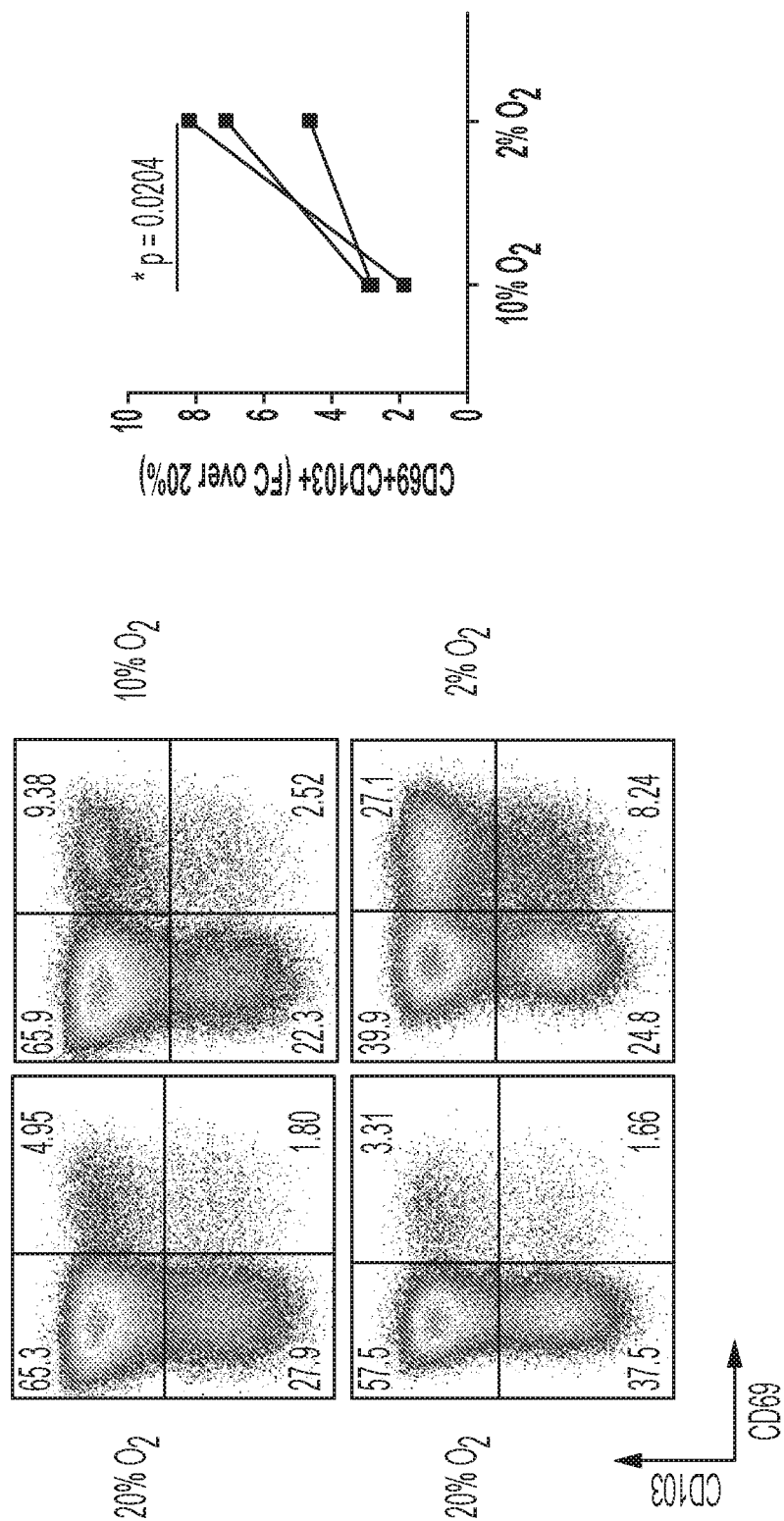

Hypoxia and TGF-β1 exposure are synergistic cues for $T_{RM}$ phenotype acquisition: Since the atmospheric oxygen levels in normal tissue culture conditions are higher than that experienced by T cells in vivo the effect of 10% Oz was evaluated, which is a physiologically relevant, non-hypoxic oxygen level T-cells are exposed to in circulation. Although there was a slight increase in $CD69^+CD103^+$ T-cells in 10% $O_2$+TGF-β1 compared to 20% $O_2$+TGF-β1, correcting for multiple comparisons uncovered no significant differences between the two conditions in expression of $T_{RM}$ signature genes (FIG. 8A-E). In addition, the fold-increase of the $CD69^+CD103^+$ population (over 20% $O_2$+TGF-β1) was significantly greater in the 2% $O_2$+TGF-β1 condition versus 10% $O_2$+TGF-β1 (FIG. 8F).

Figure 4A:
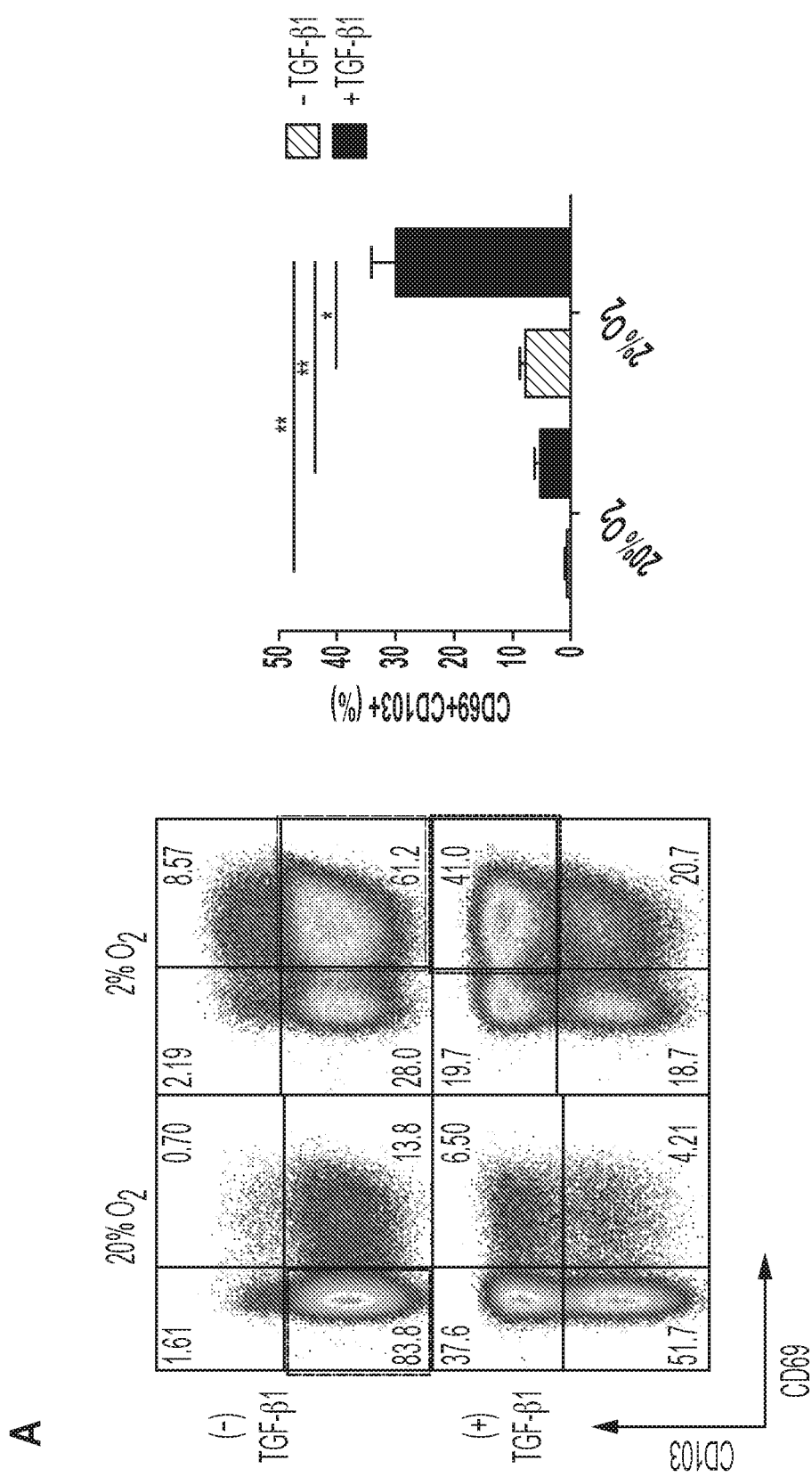
FIGS. 4A-4B: Hypoxia and TGF-β1 synergize to induce CD69$^+$CD103$^+$ cells. Naïve CD8$^+$ T cells were activated as described in FIG. 2 with or without the addition of rhTGF-β1. (A) Frequency of the CD69$^+$CD103$^+$ population and (B) expression of Tαo-associated markers was assessed by flow cytometry, representative results shown for (A) 1 donor. n=4, two-way ANOVA (A) or one-way ANOVA (B), *P<0.05, **P<0.01
Figure 4B:
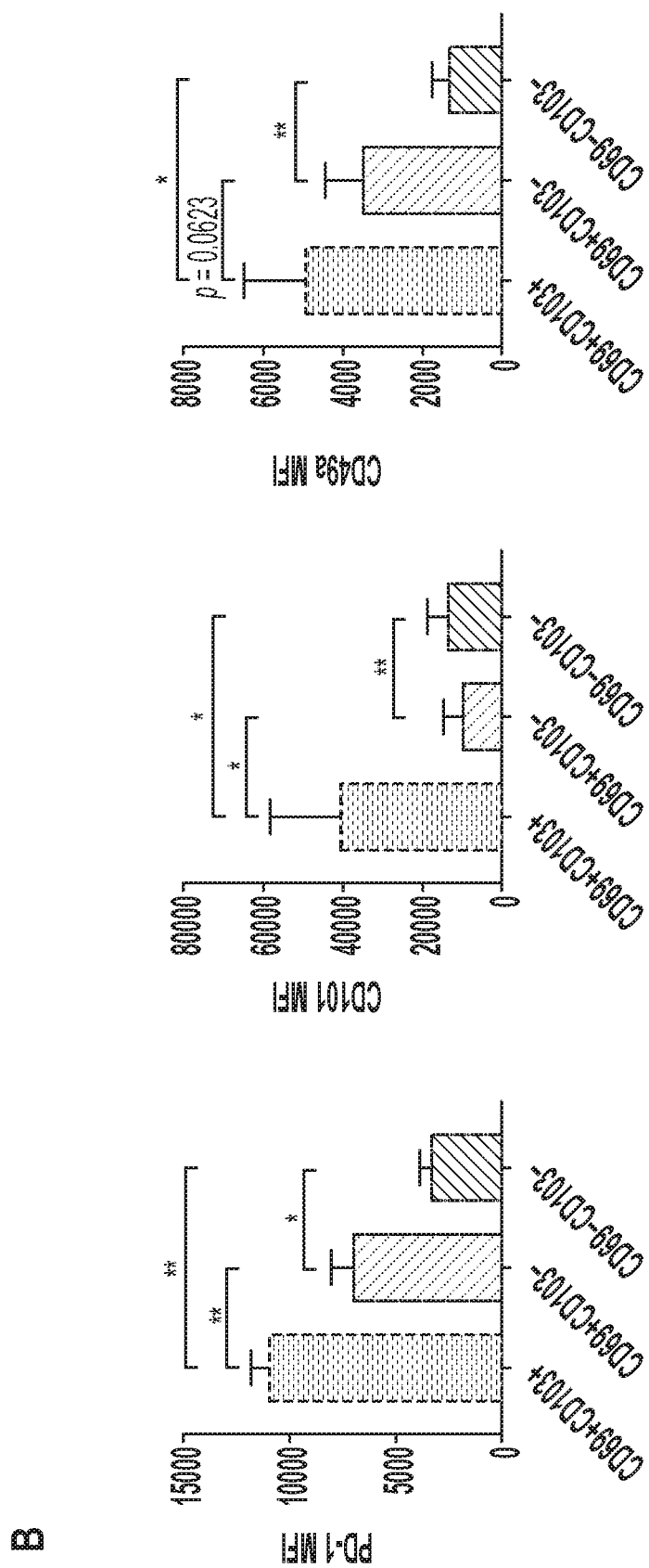

To assess the individual contributions of hypoxia and TGF-β1 to induction of $T_{RM}$ phenotype cells in vitro differentiation experiments were performed in 2% or 20% $O_2$ with or without the addition of rhTGF-1. Hypoxia primarily induced $CD69^+$ cells whereas TGF-β1 induced $CD103^+$ cells, in congruence with published reports that hypoxia and TGF-β can drive expression of these markers, respectively. Although hypoxia or TGF-β1 alone does induce a modest population of $CD69^+CD103^+$ cells, the combination of hypoxia and TGF-β1 appears to synergize induction of the resident phenotype as the combination effect was markedly greater than the additive effects of either condition alone (FIG. 4A). The $CD69^+CD103^+$ cells induced by hypoxia and TGF-β1 expressed high levels of the $T_{RM}$ markers PD-1, CD101, and CD49a, compared to the majority populations in the 20% $O_2$ and 2% $O_2$ conditions ($CD69^+CD103^-$ and $CD69^+CD103^-$, respectively) (FIG. 4B).

Figure 5A:
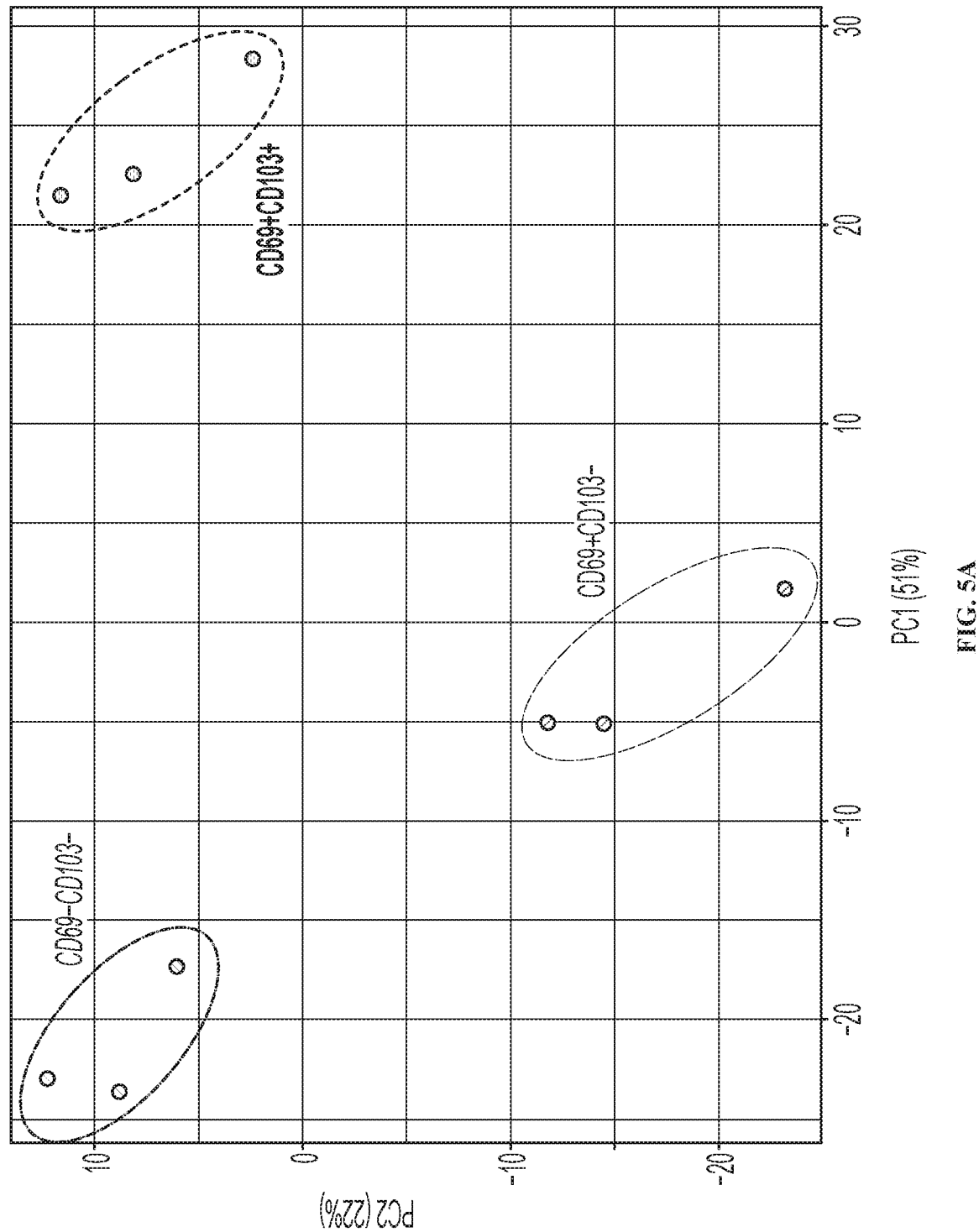
Figure 5B:
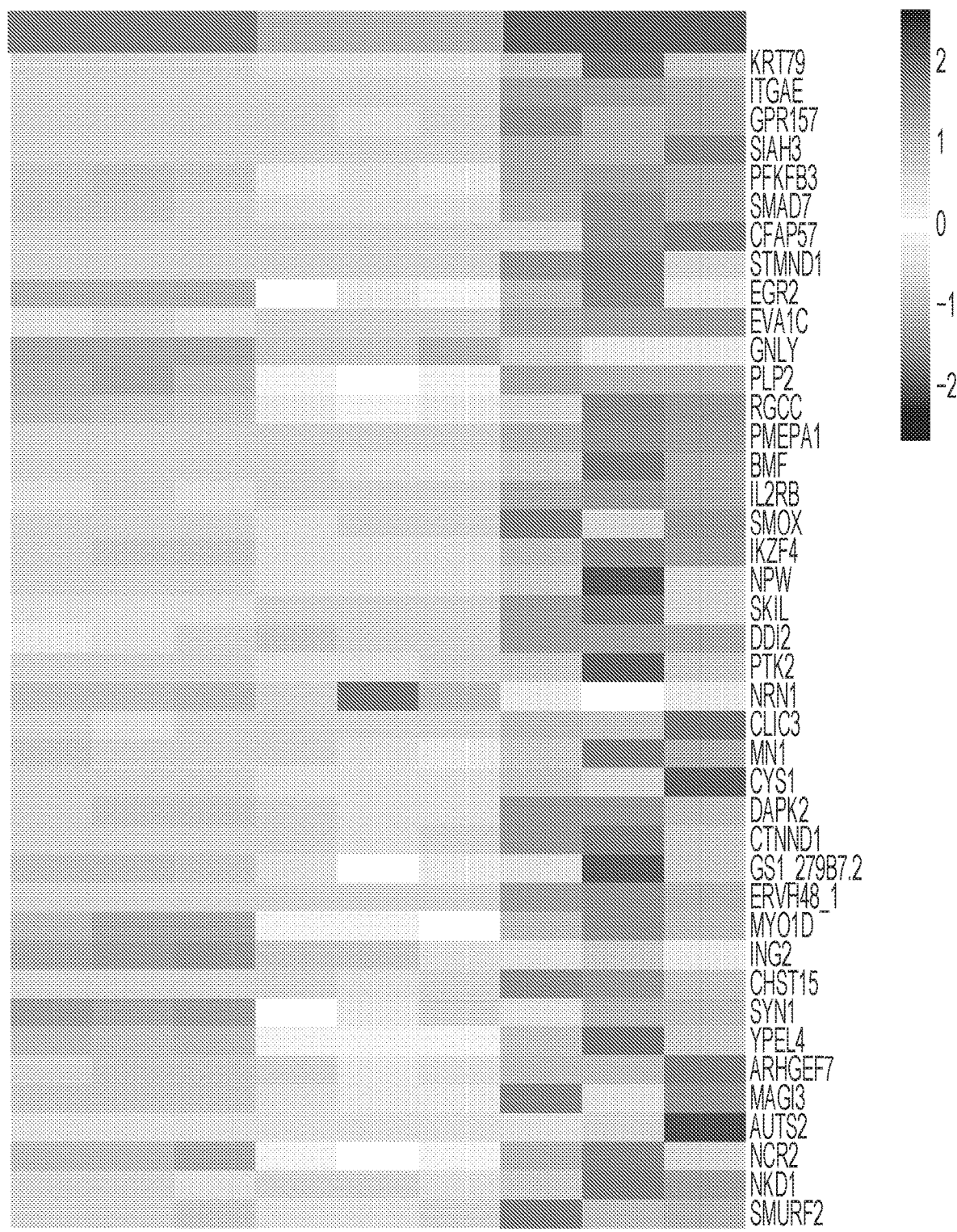
Figure 5B:
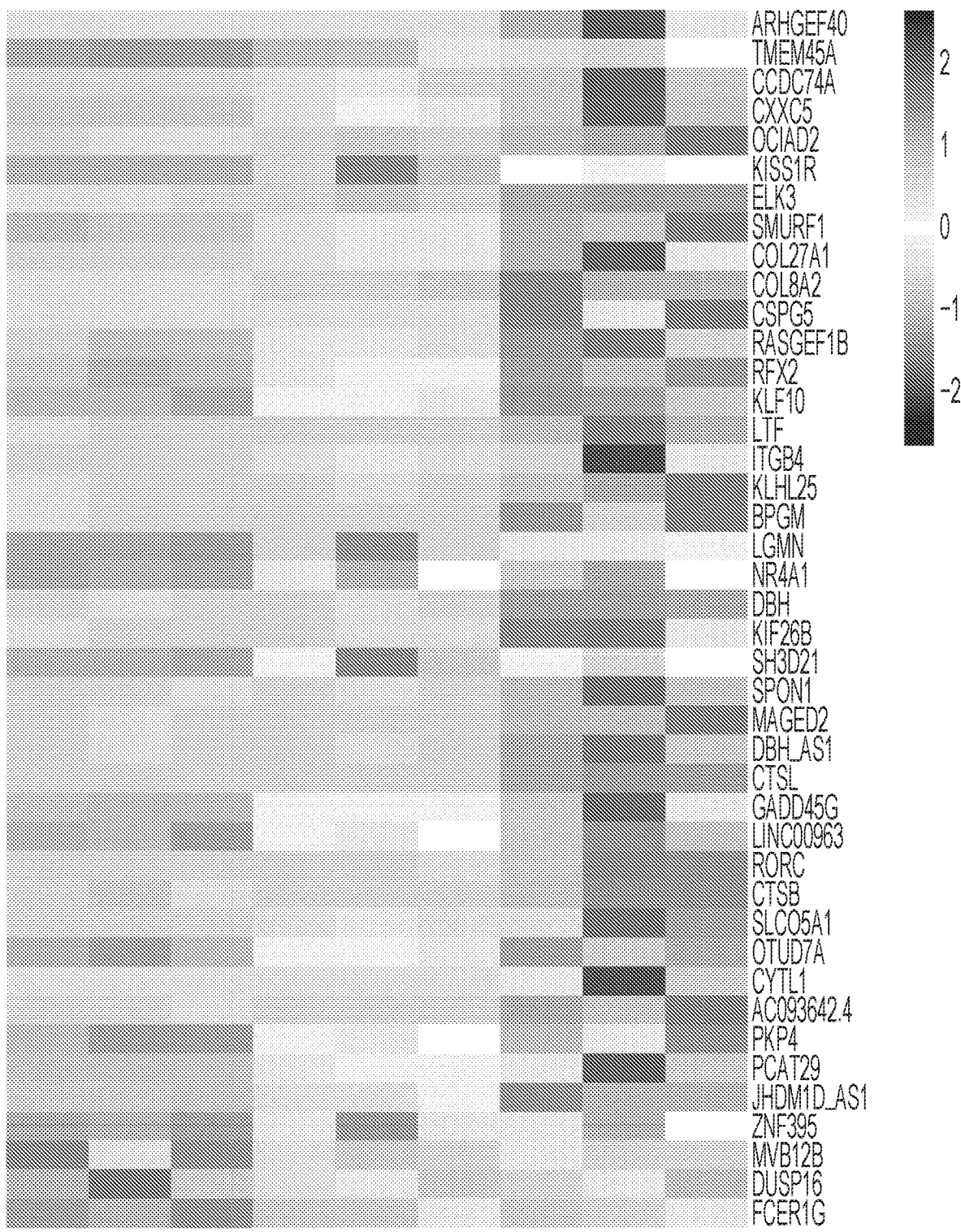
Figure 5B:
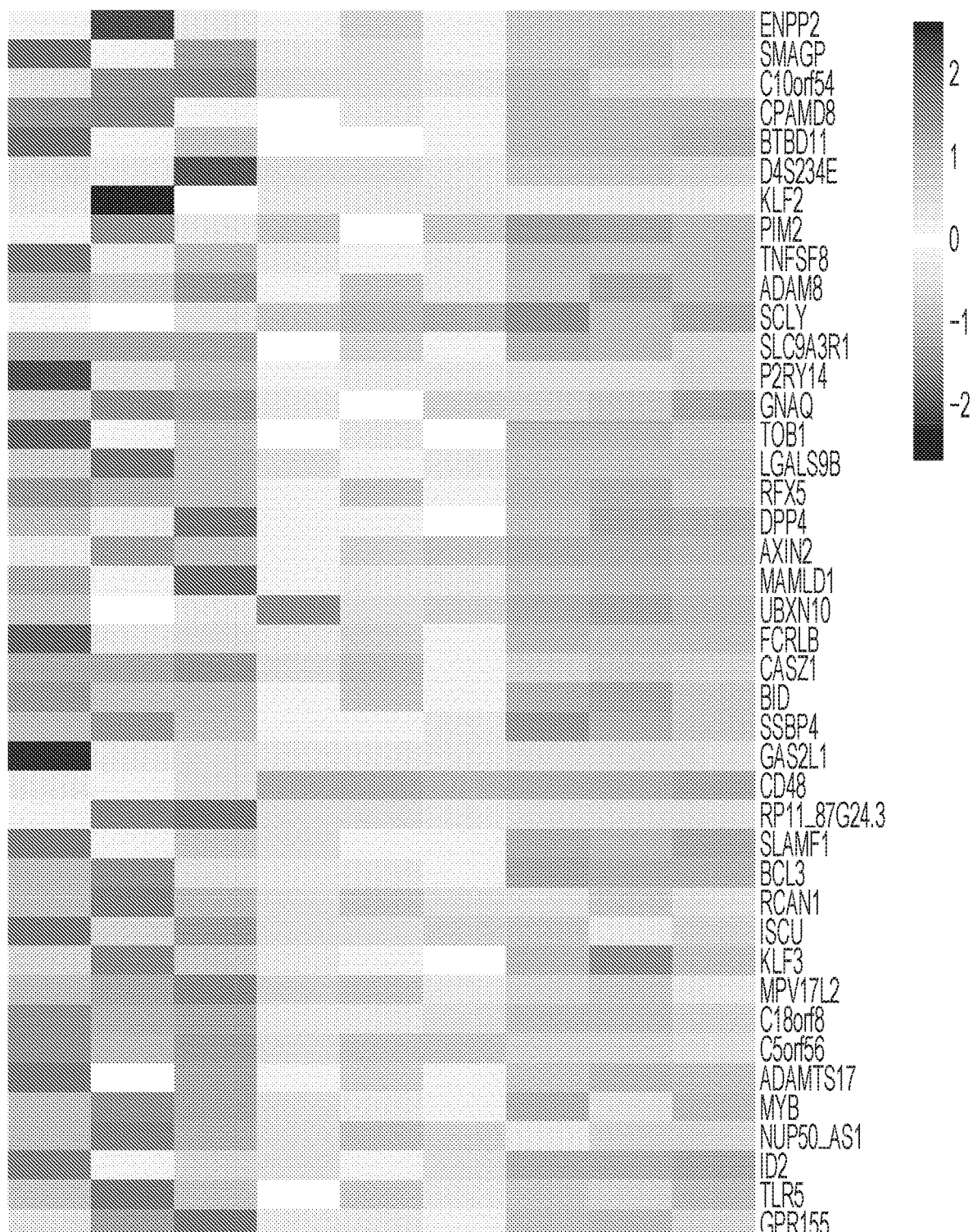
Figure 5B:
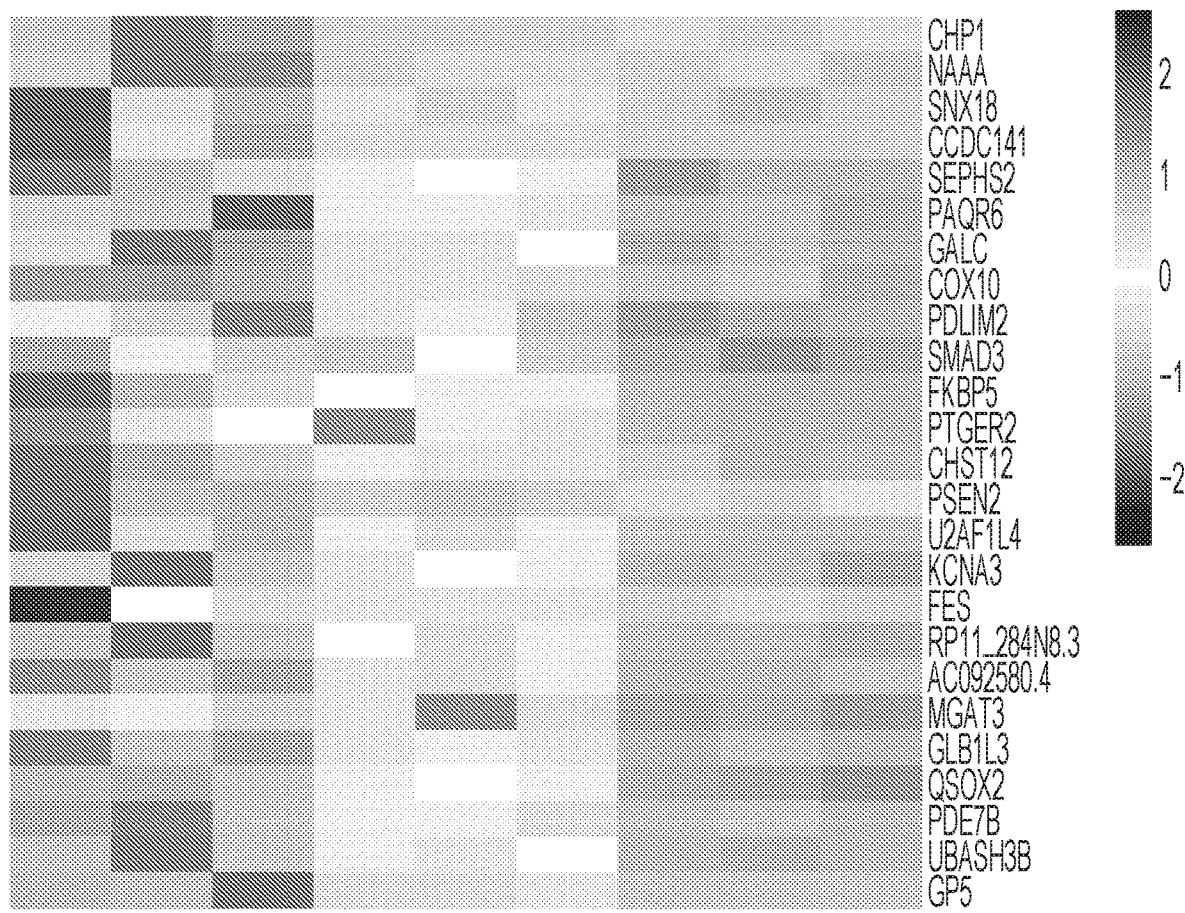
Figure 5C:
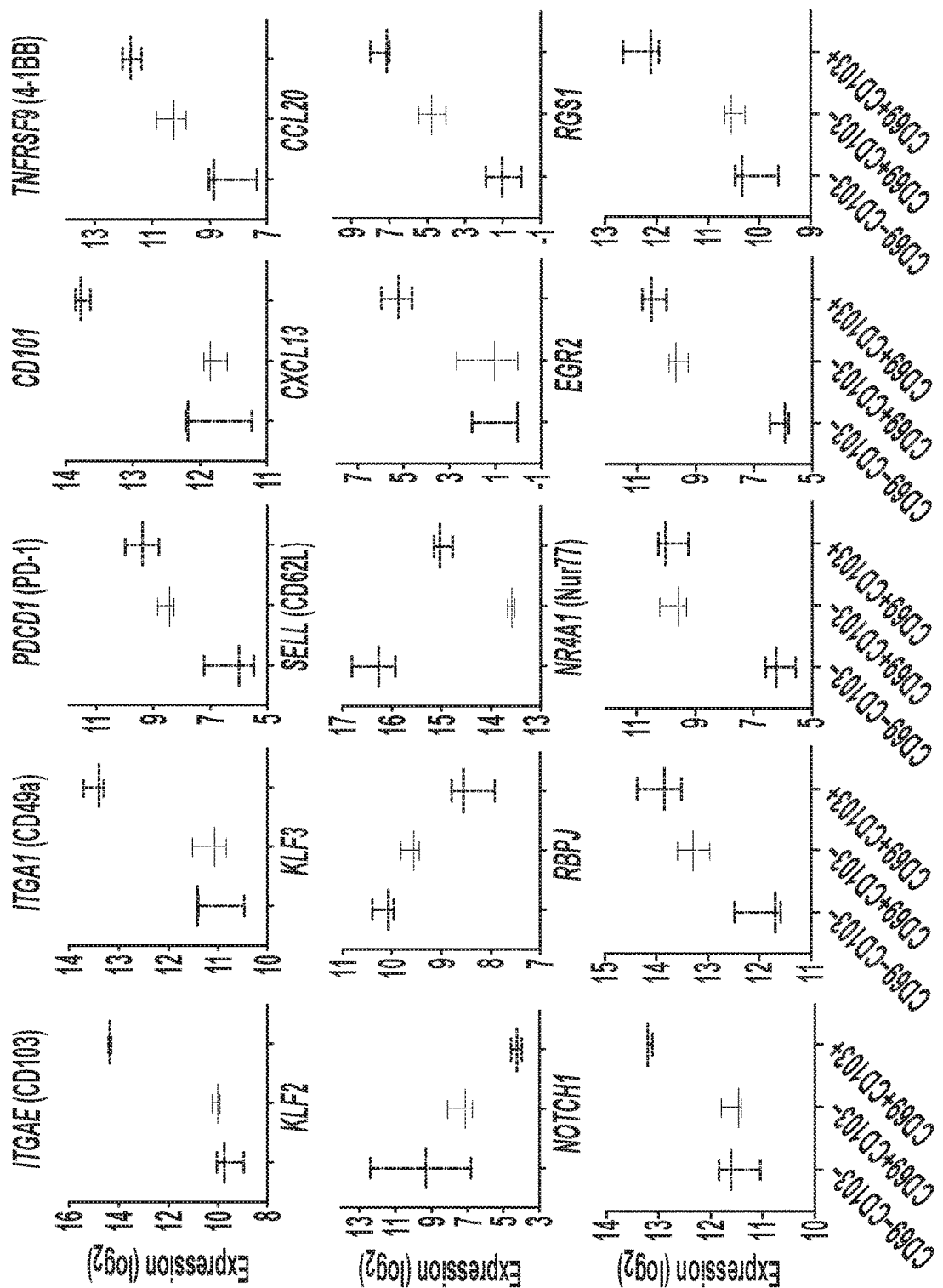

In vitro induced $T_{RM}$ show enrichment for endogenous human $T_{RM}$ gene signatures: Since differences in Tam marker expression among the $CD69^-CD103^-$ (20% $O_2$), $CD69^+CD103^-$ (2% $O_2$) and $CD69^+CD103^+$ (2% $O_2$+TGF-β1) cells suggested that these represent distinct populations, each phenotype was sorted and their transcriptional profile analyzed via RNA sequencing. Principal component analysis (PCA) confirmed that these three populations are distinct from one another (FIG. 5A). Unsupervised hierarchical clustering showed distinct gene signatures for $CD69^-CD103^-$ and $CD69^+CD103^+$ cells, whereas $CD69^+CD103^-$ cells had a somewhat intermediate transcriptional profile (FIG. 5B, 5C). Comparison of the top differentially expressed genes between $CD69^+CD103^+$ and $CD69^-CD103^-$ cells revealed gene expression patterns consistent with those reported for endogenous human $T_{RM}$, including increased expression of ITGAE, EGR2, GNLY, BMF, RASGEF1B, and NR4A1, and decreased expression of SELL, KLF2, and KLF3, indicating a non-recirculating transcriptional program (FIG. 5B, 5C). S1PR1, a KLF2- target gene, was also downregulated but did not meet the threshold for fold change. CD69$^+$CD103$^+$ cells demonstrated increased expression of ITGA1, PTCD1, CID101, and TNFRSF9, all of which are consistently reported as upregulated in endogenous human $T_{RM}$. Elevated levels of the transcription factor NOTCH1 were observed, which is known to contribute to maintenance of endogenous lung $T_{RM}$ in vivo, as well as RBPJ, which plays a central role in Notch signaling (FIG. 5C).

Endogenous $T_{RM}$ often express various chemokines, likely as part of their 'alarm function' in recruiting other immune cells to local tissues. Consistent with the chemokine profile of endogenous $T_{RM}$, in vitro induced CD69$^+$CD103$^+$ cells in the study upregulated CXCL13 and CCL20, as well as CCL4, CCL5, and CCL22 (FIG. 5C). Changes in expression of genes that have undefined roles but are consistently reported in endogenous human $T_{RM}$ were also observed, such as upregulation of MYO7A and RGS1 and downregulation of SERPINE2, RAP1GAP2, RASGRP2, and PAM65B.

Figure 5F:
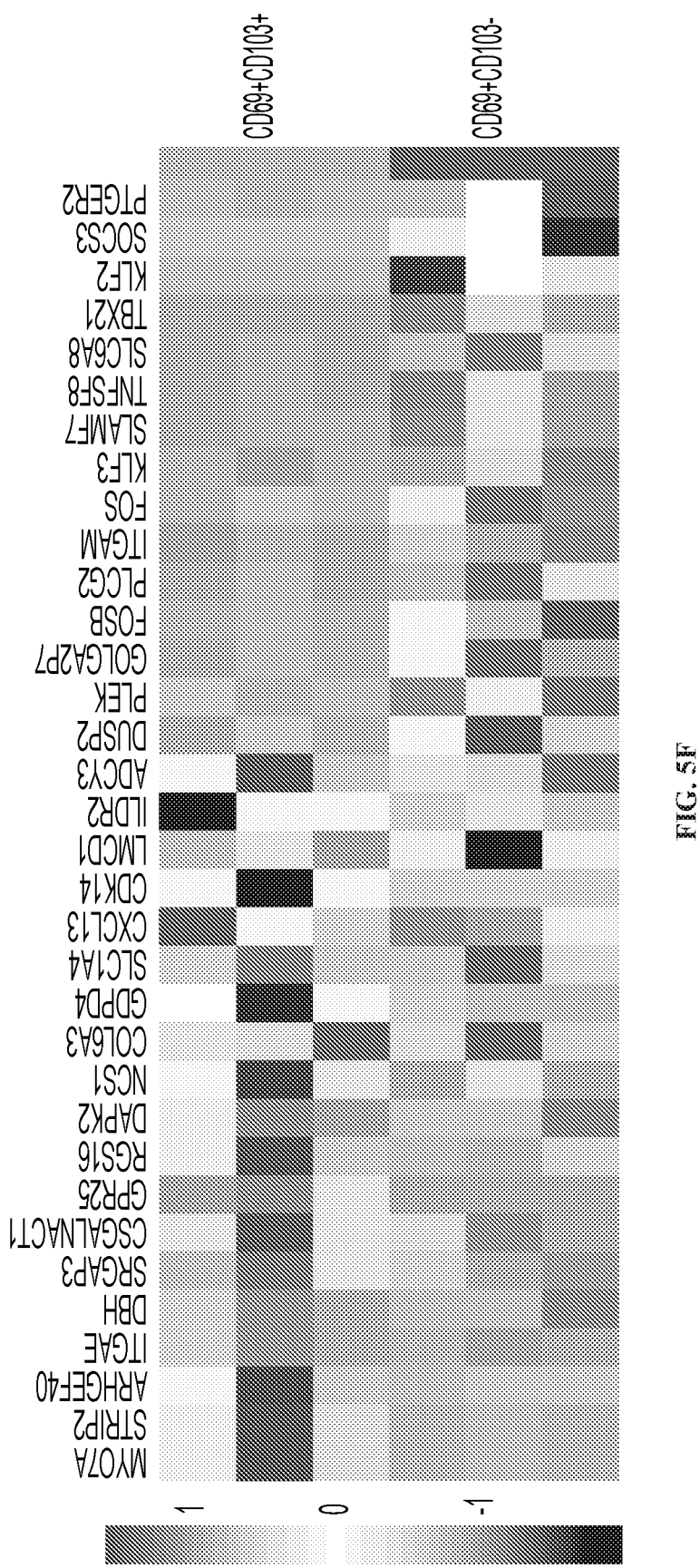

To gain insight on the physiological relevance of the findings Gene Set Enrichment Analysis (GSEA) was performed using gene signatures from published analyses on endogenous human CD103$^+$ $T_{RM}$ compared with CD103$^-$ effector memory cells from peripheral blood or CD103$^-$ T-cells within the same tissue site. The results revealed that the transcriptional profile of CD69$^+$CD103$^+$ cells compared to CD69$^-$CD103$^-$ cells is similar to the signature of $T_{RM}$ compared to blood $T_{EM}$ and local CD103$^-$ T-cells, whereas CD69$^+$CD103$^+$ cells compared to CD69$^+$CD103$^-$ is only similar to the signature of $T_{RM}$ versus CD103$^-$ T-cells within the same tissue (FIG. 5D). These results reflect the degree of difference in oxygen tension in circulation versus local tissue. TIL within the same tumor would also experience more similar oxygen levels than T cells in tissues versus those in circulation, and multiple recent profiles of TIL in various solid tumor types have reported the presence of CD103$^+$ resident memory-like TIL (TIL$_{RM}$). Thus, CD69$^+$CD103$^+$ cells induced in hypoxia+TGF-β1 were compared with CD69$^+$CD103$^+$ cells induced in hypoxia alone and observed enrichment of the gene signature reported for CD8$^+$CD69$^+$CD103$^+$ versus CD8$^+$CD69$^+$CD103$^-$ breast cancer TIL (FIG. 5E, 5F). As hypoxia and TGF-β are common features of the tumor microenvironment, the results indicate that these conditions may contribute to generation of CD103$^+$ TIL in vivo.

Figure 6A:
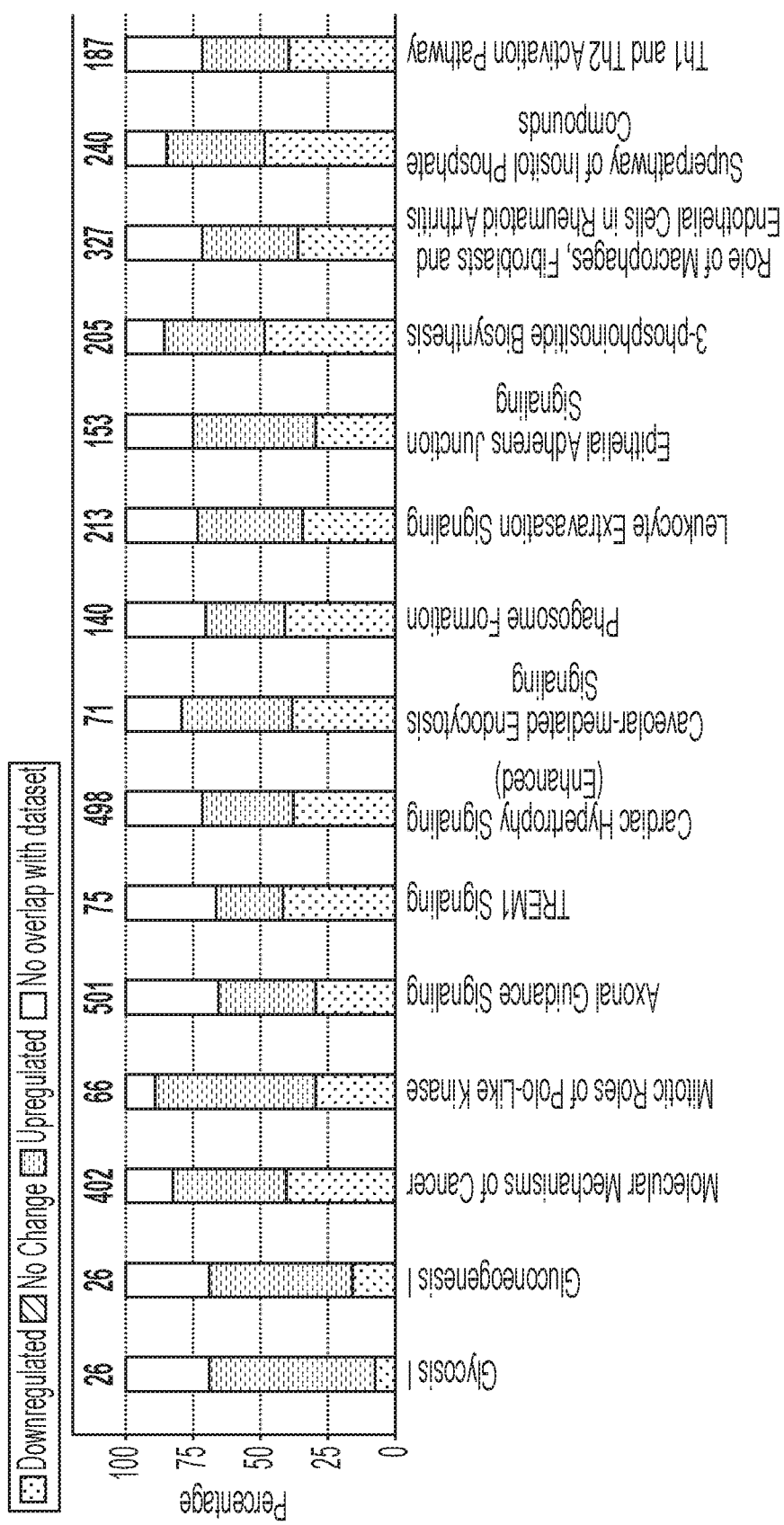
Figure 6A:
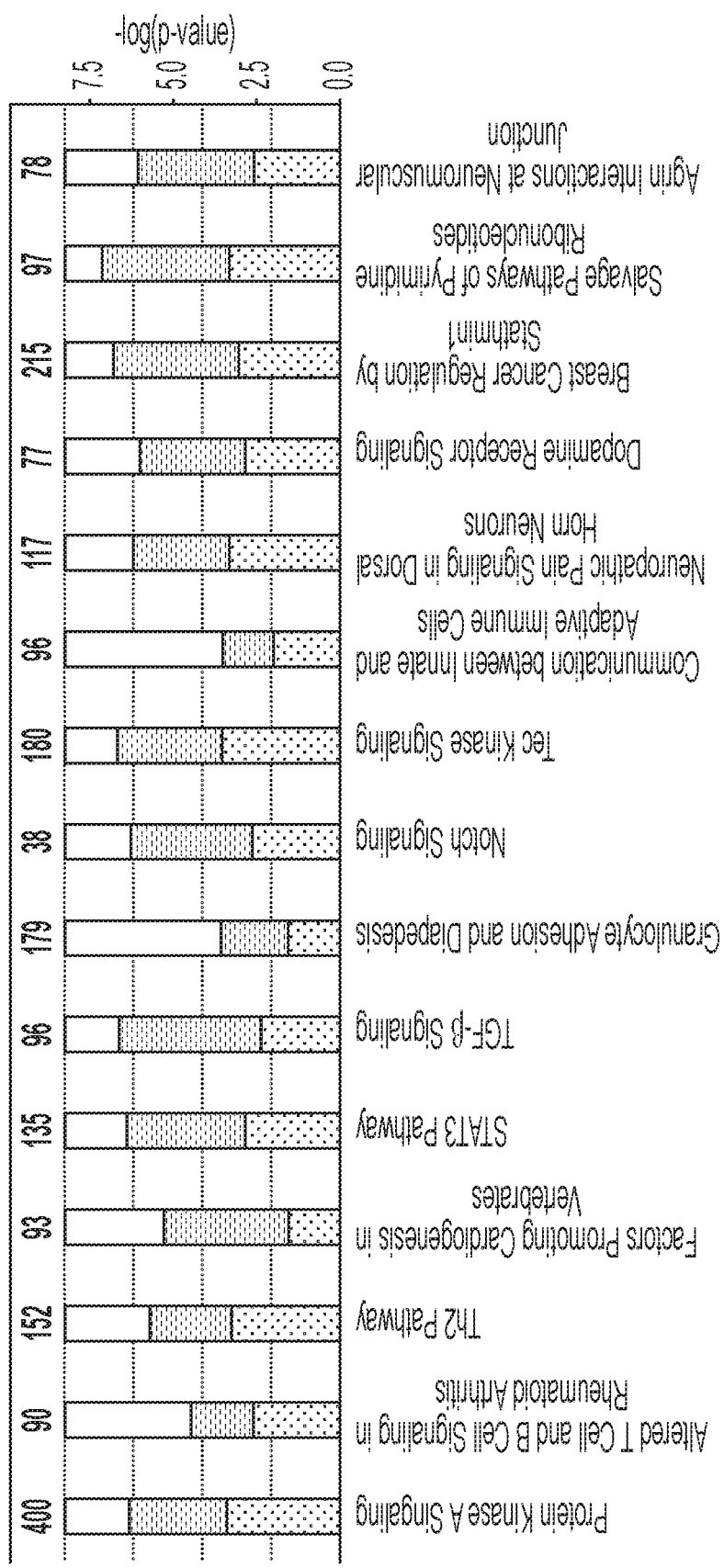

Ingenuity Pathway Analysis (IPA) comparing CD69$^+$CD103$^+$ cells with CD69$^-$CD103$^-$ cells revealed that many of the differentially expressed genes are components of glycolysis, gluconeogenesis, and TGF-β signaling pathways (FIG. 6A). Given that the cells were exposed to hypoxia and TGF-β and that hypoxia is a major regulator of cellular metabolism, these results were expected. There was also an enrichment of genes in the Notch Signaling pathway, which has been reported in endogenous human lung $T_{RM}$ (FIG. 6A). These findings raise questions regarding the role of metabolism in $T_{RM}$ differentiation. Hombrink el al. suggested that a major role of Notch signaling in lung $T_{RM}$ is regulation of metabolic programs, as chemical inhibition of Notch signaling affected genes involved in glycolysis, oxidative phosphorylation, and fatty acid metabolism pathways. It has also been suggested that deletion of the purinergic receptor P2RX7, which, like hypoxia, is a known modulator of aerobic glycolysis, impairs Tam formation via dysregulation of metabolism, as P2RX7 deficient cells displayed decreased mitochondrial mass and function, defective aerobic glycolysis, and impaired glucose uptake.

Enrichment of differentially expressed genes involved in Leukocyte Extravasation Signaling, Epithelial Adherens Junction Signaling, Integrin Signaling, and Paxilin Signaling was observed, all involved in focal adhesion signaling and suggesting changes in migratory programming (FIG. 6B). Multiple pathways involved in inositol phosphate signaling were also enriched, namely 3-phosphoinositide Biosynthesis. Superpathway of Inositol Phosphate Compounds, D-myo-inositol (1,4,5,6)-Tetrakisphosphate Biosynthesis, and D-myo-inositol (3,4,5,6)-tetrakisphosphate Biosynthesis; consistent with a previous report that PI(3)K (phosphatidylinositol-3-OH kinase) signaling is implicated in cytokine-induced downregulation of KLF2 and may play a role in generation of $T_{RM}$ in vivo.

To better understand the functional relevance of the hypoxia+TGF-β induced $T_{RM}$ transcriptional profile pathway analysis was also run on transcriptional data published by Kumar et al, and it was found that changes in the Th1 and Th2 activation and Granulocyte Adhesion and Diapedesis pathways were common to their endogenous lung $T_{RM}$ and the in vitro induced $T_{RM}$. Remarkably, the Axonal Guidance pathway was also highly significantly differentially regulated in all of the datasets. Axonal guidance, while at first seemingly unrelated to resident memory T-cells and unreported in current $T_{RM}$ literature, is a process whereby environmental cues influence migratory patterns of cells. Many of the same factors governing axon guidance are also known to regulate immune cell trafficking and can be regulated by hypoxia and/or TGF-β.

Figure 10A:
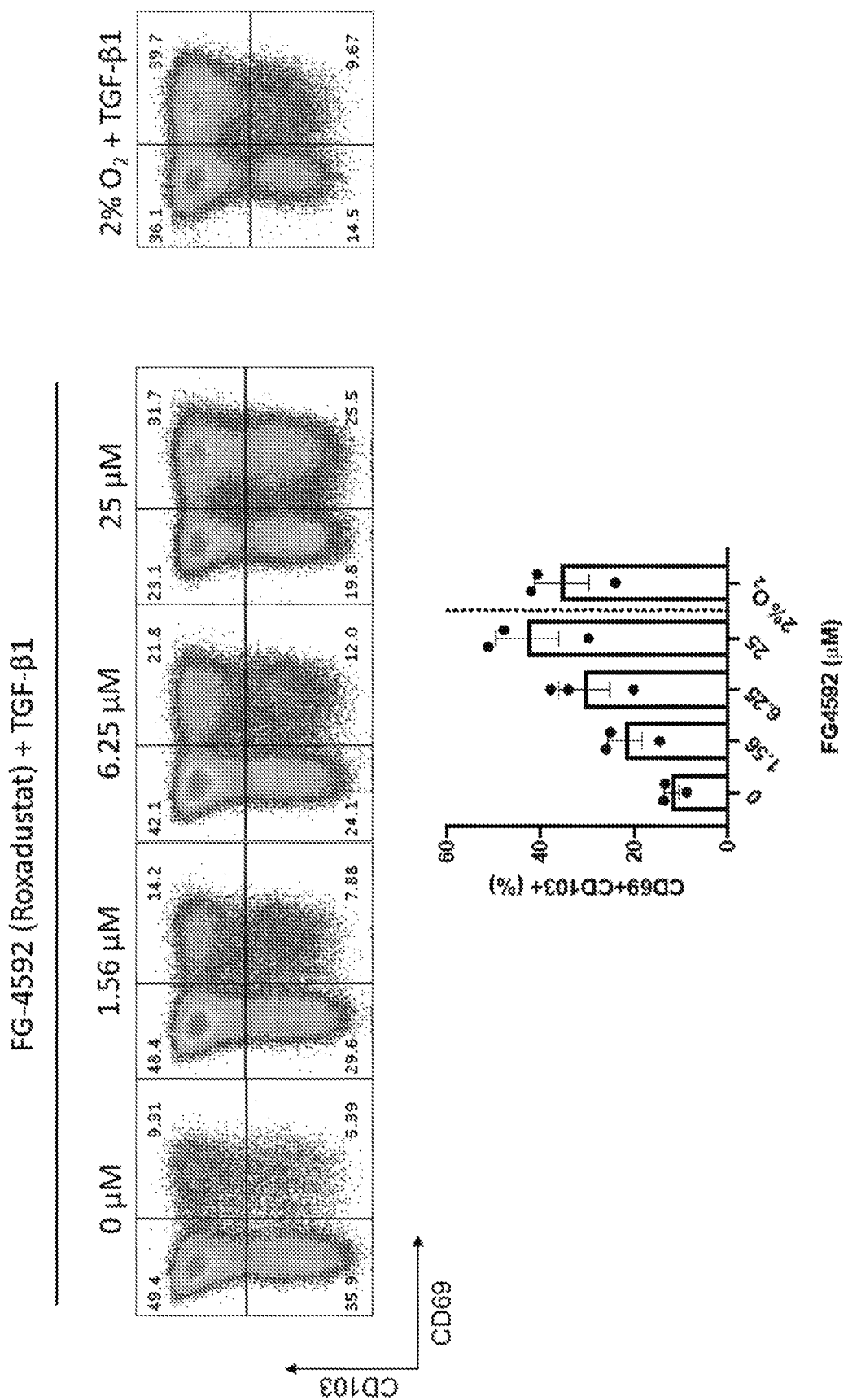
FIGS. 10A-10C: (A) Naïve CD8⁺ T-cells isolated from peripheral blood were activated in 20% $O_2$ (AtmosO₂) in the presence of the HIF prolyl hydroxylase inhibitor FG-4592 (Roxadustat) for 4 days and then for an additional 2 days with rhTGF-β1. Cells activated in 2% $O_2$ (hypoxia) with addition of rhTGF-β1 on day 4 are shown for comparison. Frequency of the CD69⁺CD103⁺ population was assessed by flow cytometry, representative results shown in FACS plots for 1 donor. n=3 (B) Stimulation with MART-1 peptide-pulsed autologous dendritic cells. Naïve CD8⁺ T-cells were stimulated with autologous monocyte-derived dendritic cells pulsed with MART-1 (M27) peptide for 7 days in 20% $O_2$ (AtmosO₂) or 2% $O_2$ with the addition of rhTGF-β1 on day 4 to generate CD69⁺CD103⁺ antigen-specific (Tetramer-) T-cells detected by flow cytometry. Representative results shown in FACS plots for 1 donor. n=4, unpaired t-test, $P<0.01$. Data are mean+/−SEM. (C) Modified rapid expansion protocol induces $T_{RM}$ phenotype in antigen-specific T cells. Hypoxia and rhTGF-β1 were used in a modified rapid expansion protocol to induce $T_{RM}$ phenotype in antigen-specific T cells. Antigen-specific T-cells were generated via stimulation with autologous MART-1 peptide-pulsed dendritic cells (ETC) or transduction of gp100-specific TCR (TCRT), labeled with fluorochrome-conjugated tetramer, and sorted. The sorted antigen-specific T cells were then stimulated with anti-CD3 (OKT3) and irradiated feeder cells in 20% $O_2$ and supplemented with IL-2 (conventional REP) or 2% $O_2$ supplemented with IL-15 and the addition of rhTGF-β1 from day 4 onwards. Bar graph shows results for MART-1 ETC, data are mean+/−SEM, n=3, unpaired t-test, $P<0.01$

A further study was conducted to assess the effect of the HIF prolyl hydroxylase inhibitor FG-4592 (Roxadustat) in combination with TGFB1. Naïve CD8$^+$ T-cells isolated from peripheral blood were activated in 20% $O_2$ (AtmosO$_2$) in the presence of the HIF prolyl hydroxylase inhibitor FG-4592 (Roxadustat) for 4 days and then for an additional 2 days with rhTGF-β1. Cells activated in 2% $O_2$ (hypoxia) with addition of rhTGF-β1 on day 4 are shown for comparison in FIG. 10A. The combination was observed to induce CD69$^+$CD103$^+$ cells (FIG. 10A).

Figure 10B:
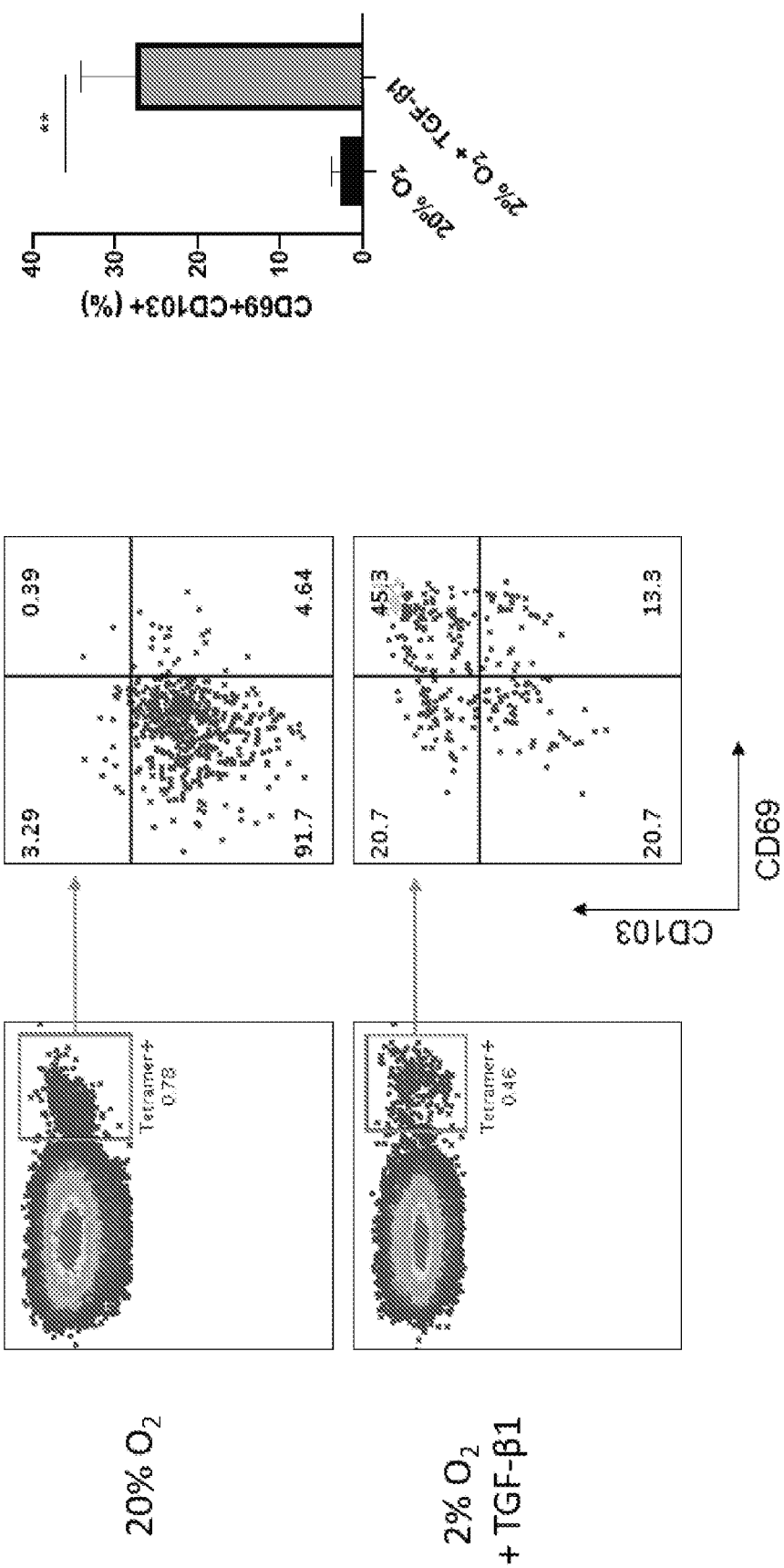
Figure 10C:
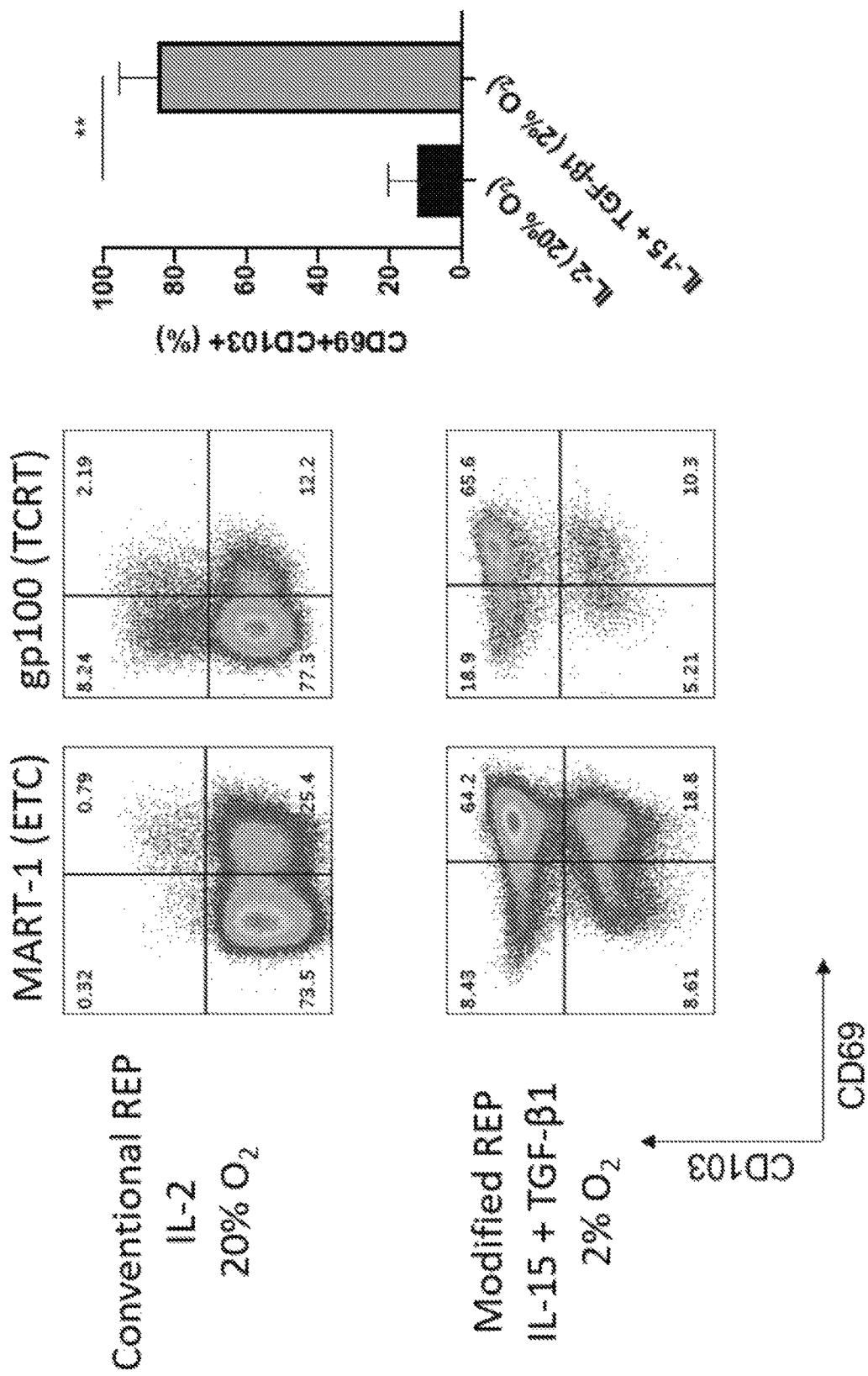

Next, naïve CD8$^+$ T-cells were stimulated with autologous monocyte-derived dendritic cells pulsed with MART-1 (M27) peptide for 7 days in 20% $O_2$ (AtmosO$_2$) or 2% $O_2$ with the addition of rhTGF-β1 on day 4 to generate CD69$^+$CD103$^+$ antigen-specific (Tetramer) T-cells detected by flow cytometry (FIG. 10B). Hypoxia and rhTGF-β1 were used in a modified rapid expansion protocol to induce $T_{RM}$ phenotype in antigen-specific T cells. Antigen-specific T-cells were generated via stimulation with autologous MART-1 peptide-pulsed dendritic cells (ETC) or transduction of gp100-specific TCR (TCRT), labeled with fluorochrome-conjugated tetramer, and sorted. The sorted antigen-specific T cells were then stimulated with anti-CD3 (OKT3) and irradiated feeder cells in 20% 02 and supplemented with IL-2 (conventional REP) or 2% 02 supplemented with IL-15 and the addition of rhTGF-β1 from day 4 onwards. Thus, it was also shown that the modified rapid expansion protocol induces $T_{RM}$ phenotype in antigen-specific T cells (FIG. 10C).

Thus, the present studies recapitulated the $T_{RM}$ phenotype in vitro from human peripheral blood derived T cells, as well as identified hypoxia as a potential cue for $T_{RM}$ differentiation. While there are obvious limitations to experiments that can be conducted in humans, the studies described provide compelling evidence that hypoxia is an environmental cue that can contribute to acquisition of a $T_{RM}$ phenotype, supported by the observation that hypoxia+TGF-β induced Tam recapitulate the transcriptional and proteomic landscape of endogenous $T_{RM}$ as well as pathways associated with migration and metabolism.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.
1) Atkuri, K. R., et al. (2005). Culturing at atmospheric oxygen levels impacts lymphocyte function. Proc National Acad Sci 102, 3756-3759.
2) Caldwell, C. C., et al. (2001). Differential effects of physiologically relevant hypoxic conditions on T lymphocyte development and effector functions. Journal of immunology (Baltimore, Md.: 1950) 167, 6140-6149.
3) Kumar, B. V., et al. (2017). Human Tissue-Resident Memory T Cells Are Defined by Core Transcriptional and Functional Signatures in Lymphoid and Mucosal Sites. Cell Rep 20, 2921-2934.
4) Mackay. L. K., et al. (2013). The developmental pathway for CD103(+)CD8+ tissue-resident memory T cells of skin. Nat Immunol 14, 1294-1301.
5) Hombrink, P., et al. (2016). Programs for the persistence, vigilance and control of human CD8(+) lung-resident memory T cells. Nat Immunol 17, 1467-1478.
6) Skon, C. N., et al. (2013). Transcriptional downregulation of S1pr1 is required for the establishment of resident memory CD8+ T cells. Nat Immunol 14, 1285-1293.
7) Mackay, L. K., and Kallies, A. (2017). Transcriptional Regulation of Tissue-Resident Lymphocytes. Trends immunol 38, 94-103.
8) Mackay, L. K., et al. (2015). T-box Transcription Factors Combine with the Cytokines TGF-beta and IL-15 to Control Tissue-Resident Memory T Cell Fate. Immunity 43, 1101-1111.
9) Mackay, L. K., et al. (2016). Hobit and Blimp1 instruct a universal transcriptional program of tissue residency in lymphocytes. Science 352, 459-463.
10) Mami0Chouaib and Tartour. (2019) Editorial: Tissue Resident Memory T Cells. Front. Immunol 10, 1-3.
11) Milner. J. J., et al. (2017). Runx3 programs CD8(+) T cell residency in non-lymphoid tissues and tumours. Nature 552, 253-257.

What is claimed is:

1. An in vitro method for producing tissue resident memory-like T cells ($T_{RM}$-like T cells) comprising:
    (a) obtaining a starting population of T cells;
    (b) culturing the starting population of T cells in hypoxic conditions or in the presence of a hypoxia-inducing agent to generate early effector cells, wherein the culturing is in media essentially free of transforming growth factor beta 1 (TGF-β1); and
    (c) further culturing the early effector cells in the presence of TGF-β1 to produce $T_{RM}$-like T cells.

2. The method of claim 1, wherein the T cells are human CD8$^+$ peripheral blood T cells.

3. The method of claim 2, wherein obtaining the human CD8$^+$ peripheral blood T cells comprises selecting for CD45RA$^+$CCR7$^+$CD8$^+$ naïve T cells from a peripheral blood sample.

4. The method of claim 3, wherein the peripheral blood sample is obtained from a healthy subject or a subject diagnosed with cancer or suspected of having cancer.

5. The method of claim 1, wherein the T cells of the starting population are stimulated by antigen presenting cells pulsed with peptide, full length antigen or cell lysate prior to culturing.

6. The method of claim 1, wherein hypoxic conditions are further defined as less than 5% oxygen.

7. The method of claim 1, wherein the hypoxia-inducing agent is a hypoxia mimetic.

8. The method of claim 7, wherein the hypoxia-inducing agent or hypoxia mimetic is cobalt chloride ($CoCl_2$), deferoxamine mesylate (DFOM), dimethyloxalylglycine (DMOG), or a prolyl hydroxylase inhibitor.

9. The method of claim 8, wherein the prolyl hydroxylase inhibitor is a 2-OG analog or Roxadustat (FG-4592).

10. The method of claim 1, wherein the culturing of step (c) is in the presence of IL-15.

11. The method of claim 1, wherein TGF-B1 is further defined as recombinant human TGF-β1 (rhTGF-β1) and is present at a concentration of 0.1 to 5 ng/mL.

12. The method of claim 1, wherein the culturing of step (c) is in hypoxic conditions or in the presence of a hypoxia-inducing agent.

13. The method of claim 12, wherein the culturing of step (c) is in the presence of IL-15.

14. The method of claim 1, wherein the $T_{RM}$-like T cells are CD69$^+$CD103$^+$.

15. The method of claim 14, wherein at least 30% of the cells produced in step (c) are CD69$^+$CD103$^+$ cells.

16. The method of claim 1, wherein the $T_{RM}$-like T cells have essentially no expression of CXCR6 protein.

17. The method of claim 1, further comprising producing antigen-specific $T_{RM}$-like T cells by transducing the $T_{RM}$-like T cells with a T cell receptor (TCR) specific for the antigen of interest or by culturing the starting population of T cells with peptide-pulsed antigen presenting cells (APCs).

18. The method of claim 1, wherein antigen-specific $T_{RM}$-like T cells are produced by culturing the cells in the presence of a histone deacetylase (HDAC) inhibitor during step (b) and/or step (c) to differentiate antigen-specific T cells to the $T_{RM}$ phenotype.

* * * * *

SEQUENCE LISTING

```
<160> NUMBER OF SEQ ID NOS: 46

<210> SEQ ID NO 1
<211> LENGTH: 22
<212> TYPE: DNA
<213> ORGANISM: Artificial sequence
<220> FEATURE:
<223> OTHER INFORMATION: Synthetic primer

<400> SEQUENCE: 1
attgtccagg ccaatacaca tt                                              22

<210> SEQ ID NO 2
<211> LENGTH: 23
<212> TYPE: DNA
<213> ORGANISM: Artificial sequence
<220> FEATURE:
<223> OTHER INFORMATION: Synthetic primer

<400> SEQUENCE: 2
cctctctacc tgcgtatcgt ttt                                             23

<210> SEQ ID NO 3
<211> LENGTH: 21
<212> TYPE: DNA
<213> ORGANISM: Artificial sequence
<220> FEATURE:
<223> OTHER INFORMATION: Synthetic primer

<400> SEQUENCE: 3
agccatgcaa cacgtcttag a                                               21

<210> SEQ ID NO 4
<211> LENGTH: 21
```

```
<212> TYPE: DNA
<213> ORGANISM: Artificial sequence
<220> FEATURE:
<223> OTHER INFORMATION: Synthetic primer

<400> SEQUENCE: 4
tcctcgaata tgccaccatc g                                              21

<210> SEQ ID NO 5
<211> LENGTH: 23
<212> TYPE: DNA
<213> ORGANISM: Artificial sequence
<220> FEATURE:
<223> OTHER INFORMATION: Synthetic primer

<400> SEQUENCE: 5
ctggacatag tcatagtgct gga                                            23

<210> SEQ ID NO 6
<211> LENGTH: 21
<212> TYPE: DNA
<213> ORGANISM: Artificial sequence
<220> FEATURE:
<223> OTHER INFORMATION: Synthetic primer

<400> SEQUENCE: 6
acctgtgtct gtttaggacc a                                              21

<210> SEQ ID NO 7
<211> LENGTH: 24
<212> TYPE: DNA
<213> ORGANISM: Artificial sequence
<220> FEATURE:
<223> OTHER INFORMATION: Synthetic primer

<400> SEQUENCE: 7
caagagccta ctgggcatct acac                                           24

<210> SEQ ID NO 8
<211> LENGTH: 24
<212> TYPE: DNA
<213> ORGANISM: Artificial sequence
<220> FEATURE:
<223> OTHER INFORMATION: Synthetic primer

<400> SEQUENCE: 8
tggccttaac cactacaatg aaac                                           24

<210> SEQ ID NO 9
<211> LENGTH: 23
<212> TYPE: DNA
<213> ORGANISM: Artificial sequence
<220> FEATURE:
<223> OTHER INFORMATION: Synthetic primer

<400> SEQUENCE: 9
tcaccgtcat cagcattgat agg                                            23

<210> SEQ ID NO 10
<211> LENGTH: 20
<212> TYPE: DNA
<213> ORGANISM: Artificial sequence
<220> FEATURE:
<223> OTHER INFORMATION: Synthetic primer

<400> SEQUENCE: 10
```

-continued

```
gtttccacat tgcggagcac                                              20

<210> SEQ ID NO 11
<211> LENGTH: 20
<212> TYPE: DNA
<213> ORGANISM: Artificial sequence
<220> FEATURE:
<223> OTHER INFORMATION: Synthetic primer

<400> SEQUENCE: 11
acgagggaca ataggagcca                                              20

<210> SEQ ID NO 12
<211> LENGTH: 20
<212> TYPE: DNA
<213> ORGANISM: Artificial sequence
<220> FEATURE:
<223> OTHER INFORMATION: Synthetic primer

<400> SEQUENCE: 12
ggcatactcc gtctgctcag                                              20

<210> SEQ ID NO 13
<211> LENGTH: 20
<212> TYPE: DNA
<213> ORGANISM: Artificial sequence
<220> FEATURE:
<223> OTHER INFORMATION: Synthetic primer

<400> SEQUENCE: 13
cagccagtga cgtacagctc                                              20

<210> SEQ ID NO 14
<211> LENGTH: 21
<212> TYPE: DNA
<213> ORGANISM: Artificial sequence
<220> FEATURE:
<223> OTHER INFORMATION: Synthetic primer

<400> SEQUENCE: 14
ccattccgtt gcctcacaga a                                            21

<210> SEQ ID NO 15
<211> LENGTH: 21
<212> TYPE: DNA
<213> ORGANISM: Artificial sequence
<220> FEATURE:
<223> OTHER INFORMATION: Synthetic primer

<400> SEQUENCE: 15
gcctcttcct gctaatcagc g                                            21

<210> SEQ ID NO 16
<211> LENGTH: 22
<212> TYPE: DNA
<213> ORGANISM: Artificial sequence
<220> FEATURE:
<223> OTHER INFORMATION: Synthetic primer

<400> SEQUENCE: 16
gcagtacaga atgacgatgg ag                                           22

<210> SEQ ID NO 17
<211> LENGTH: 18
<212> TYPE: DNA
<213> ORGANISM: Artificial sequence
```

```
<220> FEATURE:
<223> OTHER INFORMATION: Synthetic primer

<400> SEQUENCE: 17
catctgaagg cgcatctg                                                   18

<210> SEQ ID NO 18
<211> LENGTH: 19
<212> TYPE: DNA
<213> ORGANISM: Artificial sequence
<220> FEATURE:
<223> OTHER INFORMATION: Synthetic primer

<400> SEQUENCE: 18
cgtgtgcttt cggtagtgg                                                  19

<210> SEQ ID NO 19
<211> LENGTH: 20
<212> TYPE: DNA
<213> ORGANISM: Artificial sequence
<220> FEATURE:
<223> OTHER INFORMATION: Synthetic primer

<400> SEQUENCE: 19
gcccacgtct acctgtgcaa                                                 20

<210> SEQ ID NO 20
<211> LENGTH: 20
<212> TYPE: DNA
<213> ORGANISM: Artificial sequence
<220> FEATURE:
<223> OTHER INFORMATION: Synthetic primer

<400> SEQUENCE: 20
gggcagtggg attgagtccg                                                 20

<210> SEQ ID NO 21
<211> LENGTH: 20
<212> TYPE: DNA
<213> ORGANISM: Artificial sequence
<220> FEATURE:
<223> OTHER INFORMATION: Synthetic primer

<400> SEQUENCE: 21
caacacagga gcgcactgga                                                 20

<210> SEQ ID NO 22
<211> LENGTH: 20
<212> TYPE: DNA
<213> ORGANISM: Artificial sequence
<220> FEATURE:
<223> OTHER INFORMATION: Synthetic primer

<400> SEQUENCE: 22
gtgttggaag cgttgcaggc                                                 20

<210> SEQ ID NO 23
<211> LENGTH: 20
<212> TYPE: DNA
<213> ORGANISM: Artificial sequence
<220> FEATURE:
<223> OTHER INFORMATION: Synthetic primer

<400> SEQUENCE: 23
tgcagctata cccaggctgg                                                 20
```

<210> SEQ ID NO 24
<211> LENGTH: 19
<212> TYPE: DNA
<213> ORGANISM: Artificial sequence
<220> FEATURE:
<223> OTHER INFORMATION: Synthetic primer

<400> SEQUENCE: 24
cctcgaccgc ctcttcttc                                                   19

<210> SEQ ID NO 25
<211> LENGTH: 20
<212> TYPE: DNA
<213> ORGANISM: Artificial sequence
<220> FEATURE:
<223> OTHER INFORMATION: Synthetic primer

<400> SEQUENCE: 25
cccgtaccaa tgtcccatga                                                  20

<210> SEQ ID NO 26
<211> LENGTH: 21
<212> TYPE: DNA
<213> ORGANISM: Artificial sequence
<220> FEATURE:
<223> OTHER INFORMATION: Synthetic primer

<400> SEQUENCE: 26
cctgtcacct ggcaaccatt t                                                21

<210> SEQ ID NO 27
<211> LENGTH: 20
<212> TYPE: DNA
<213> ORGANISM: Artificial sequence
<220> FEATURE:
<223> OTHER INFORMATION: Synthetic primer

<400> SEQUENCE: 27
agcaccacaa gccacttcag                                                  20

<210> SEQ ID NO 28
<211> LENGTH: 20
<212> TYPE: DNA
<213> ORGANISM: Artificial sequence
<220> FEATURE:
<223> OTHER INFORMATION: Synthetic primer

<400> SEQUENCE: 28
gggaaggagc ggtcaaactg                                                  20

<210> SEQ ID NO 29
<211> LENGTH: 20
<212> TYPE: DNA
<213> ORGANISM: Artificial sequence
<220> FEATURE:
<223> OTHER INFORMATION: Synthetic primer

<400> SEQUENCE: 29
caagctgtcc tgtgtgggca                                                  20

<210> SEQ ID NO 30
<211> LENGTH: 20
<212> TYPE: DNA
<213> ORGANISM: Artificial sequence
<220> FEATURE:
<223> OTHER INFORMATION: Synthetic primer -continued

<400> SEQUENCE: 30
cgctcaaagt tgcgtgcctg                                               20

<210> SEQ ID NO 31
<211> LENGTH: 20
<212> TYPE: DNA
<213> ORGANISM: Artificial sequence
<220> FEATURE:
<223> OTHER INFORMATION: Synthetic primer

<400> SEQUENCE: 31
atggaacgat gacgcctgcc                                               20

<210> SEQ ID NO 32
<211> LENGTH: 20
<212> TYPE: DNA
<213> ORGANISM: Artificial sequence
<220> FEATURE:
<223> OTHER INFORMATION: Synthetic primer

<400> SEQUENCE: 32
ggcctccaaa ggctcacact                                               20

<210> SEQ ID NO 33
<211> LENGTH: 23
<212> TYPE: DNA
<213> ORGANISM: Artificial sequence
<220> FEATURE:
<223> OTHER INFORMATION: Synthetic primer

<400> SEQUENCE: 33
tggaaagagg agagtgacag aaa                                           23

<210> SEQ ID NO 34
<211> LENGTH: 21
<212> TYPE: DNA
<213> ORGANISM: Artificial sequence
<220> FEATURE:
<223> OTHER INFORMATION: Synthetic primer

<400> SEQUENCE: 34
tccttgatgg tctccacact c                                             21

<210> SEQ ID NO 35
<211> LENGTH: 20
<212> TYPE: DNA
<213> ORGANISM: Artificial sequence
<220> FEATURE:
<223> OTHER INFORMATION: Synthetic primer

<400> SEQUENCE: 35
ggcgctcccc aagaagacag                                               20

<210> SEQ ID NO 36
<211> LENGTH: 20
<212> TYPE: DNA
<213> ORGANISM: Artificial sequence
<220> FEATURE:
<223> OTHER INFORMATION: Synthetic primer

<400> SEQUENCE: 36
caggcttgtc actcggggtt                                               20

<210> SEQ ID NO 37

-continued

<210> SEQ ID NO 37
<211> LENGTH: 20
<212> TYPE: DNA
<213> ORGANISM: Artificial sequence
<220> FEATURE:
<223> OTHER INFORMATION: Synthetic primer

<400> SEQUENCE: 37
caaccaatcc tgcttctgct                                       20

<210> SEQ ID NO 38
<211> LENGTH: 20
<212> TYPE: DNA
<213> ORGANISM: Artificial sequence
<220> FEATURE:
<223> OTHER INFORMATION: Synthetic primer

<400> SEQUENCE: 38
ccgcacctct tcagagactt                                       20

<210> SEQ ID NO 39
<211> LENGTH: 21
<212> TYPE: DNA
<213> ORGANISM: Artificial sequence
<220> FEATURE:
<223> OTHER INFORMATION: Synthetic primer

<400> SEQUENCE: 39
tggacacggg actctacatc t                                     21

<210> SEQ ID NO 40
<211> LENGTH: 23
<212> TYPE: DNA
<213> ORGANISM: Artificial sequence
<220> FEATURE:
<223> OTHER INFORMATION: Synthetic primer

<400> SEQUENCE: 40
ggcacggttc tggatcaatt aca                                   23

<210> SEQ ID NO 41
<211> LENGTH: 21
<212> TYPE: DNA
<213> ORGANISM: Artificial sequence
<220> FEATURE:
<223> OTHER INFORMATION: Synthetic primer

<400> SEQUENCE: 41
tctggcatca acgctgtctt c                                     21

<210> SEQ ID NO 42
<211> LENGTH: 19
<212> TYPE: DNA
<213> ORGANISM: Artificial sequence
<220> FEATURE:
<223> OTHER INFORMATION: Synthetic primer

<400> SEQUENCE: 42
cgataccgga gccaatggt                                        19

<210> SEQ ID NO 43
<211> LENGTH: 20
<212> TYPE: DNA
<213> ORGANISM: Artificial sequence
<220> FEATURE:
<223> OTHER INFORMATION: Synthetic primer

<400> SEQUENCE: 43

```
aaatgctttc tccgctctga                                                20

<210> SEQ ID NO 44
<211> LENGTH: 20
<212> TYPE: DNA
<213> ORGANISM: Artificial sequence
<220> FEATURE:
<223> OTHER INFORMATION: Synthetic primer

<400> SEQUENCE: 44
cccactgagg agtccaacat                                                20

<210> SEQ ID NO 45
<211> LENGTH: 20
<212> TYPE: DNA
<213> ORGANISM: Artificial sequence
<220> FEATURE:
<223> OTHER INFORMATION: Synthetic primer

<400> SEQUENCE: 45
cctcaaggtc gtgcgtctga                                                20

<210> SEQ ID NO 46
<211> LENGTH: 20
<212> TYPE: DNA
<213> ORGANISM: Artificial sequence
<220> FEATURE:
<223> OTHER INFORMATION: Synthetic primer

<400> SEQUENCE: 46
tccacgttct tctcggcctg                                                20
```